US008859559B2

(12) United States Patent
Heckel et al.

(10) Patent No.: US 8,859,559 B2
(45) Date of Patent: Oct. 14, 2014

(54) SUBSTITUTED PYRAZINES AND THEIR USE IN THE TREATMENT OF DISEASE

(71) Applicant: Boehringer Ingelheim International GmbH, Ingelheim am Rhein (DE)

(72) Inventors: Armin Heckel, Biberach an der Riss (DE); Andreas Blum, Warthausen (DE); Dieter Hamprecht, Pozzolengo (IT); Joerg Kley, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/717,848

(22) Filed: Dec. 18, 2012

(65) Prior Publication Data

US 2013/0157981 A1  Jun. 20, 2013

(30) Foreign Application Priority Data

Dec. 20, 2011 (EP) .................................. 11194687

(51) Int. Cl.
| | | |
|---|---|---|
| A61K 31/4192 | (2006.01) | |
| A61K 31/4468 | (2006.01) | |
| A61K 31/4965 | (2006.01) | |
| C07D 213/74 | (2006.01) | |
| C07D 241/16 | (2006.01) | |
| C07D 403/02 | (2006.01) | |
| A61K 31/501 | (2006.01) | |
| C07F 9/6558 | (2006.01) | |
| C07D 401/12 | (2006.01) | |
| C07D 403/12 | (2006.01) | |
| C07D 401/14 | (2006.01) | |
| A61K 45/06 | (2006.01) | |
| A61K 31/683 | (2006.01) | |
| A61K 31/497 | (2006.01) | |
| A61K 31/55 | (2006.01) | |
| A61K 31/675 | (2006.01) | |
| C07D 451/04 | (2006.01) | |

(52) U.S. Cl.
CPC ............ *C07D 401/12* (2013.01); *A61K 31/501* (2013.01); *C07F 9/65583* (2013.01); *C07D 403/12* (2013.01); *C07D 401/14* (2013.01); *A61K 45/06* (2013.01); *A61K 31/683* (2013.01); *A61K 31/497* (2013.01); *A61K 31/55* (2013.01); *A61K 31/675* (2013.01); *C07D 451/04* (2013.01)
USPC ...... 514/255.06; 514/326; 514/359; 546/304; 548/255

(58) Field of Classification Search
CPC .......... A61K 31/4192; A61K 31/4468; A61K 31/4965; C07D 213/74; C07D 241/16; C07D 403/02
USPC ................... 514/255.06, 326, 359; 546/304; 548/255
See application file for complete search history.

(56) References Cited

U.S. PATENT DOCUMENTS 3,953,476 A  4/1976 Cragoe, Jr. et al.

FOREIGN PATENT DOCUMENTS

| | | |
|---|---|---|
| GB | 1214408 A | 12/1970 |
| GB | 1214409 A | 12/1970 |
| WO | 2008135557 A1 | 11/2008 |
| WO | 2009138378 A1 | 11/2009 |
| WO | 2013003386 A1 | 1/2013 |
| WO | 2013003444 A1 | 1/2013 |

OTHER PUBLICATIONS

Berge, Stephen, M., et al; Review Article: Pharmaceutical Salts; Journal of Pharmaceutical Sciences (1977) vol. 66, No. 1 pp. 1-19.
European Search Report for EP 11187553 Date of Completion of the Search Feb. 10, 2012.
European Search Report for EP 11187566 Date of Completion of the Search May 10, 2012.
European Search Report for EP 11194687 Date of Completion of the Search Mar. 7, 2012.
Hirsch, Andrew, J., et al; Design, Synthesis, and Structure-Activity relationships of Novel 2-Substituted Pyrazinoylguanidine Epithlial Sodium Channel Blockers: Drugs for Cystic Fibrosis and Chronic Brochitis; Journal of Medicinal Chemistry (2006) vol. 49, No. 14 pp. 4098-4115.
Li, Jack, H., et al; Stereoselective Blockade of Amphibian Epithelial Sodium Channels by Amiloride Analogs; The Journal of Pharmacology and Experimental Therapeutics (1993) vol. 267, No. 3 pp. 1081-1084.

(Continued)

*Primary Examiner* — Douglas M Willis
(74) *Attorney, Agent, or Firm* — Michael P. Morris; Edward S. Lazer

(57) ABSTRACT

The present invention relates to compounds of general formula (I)

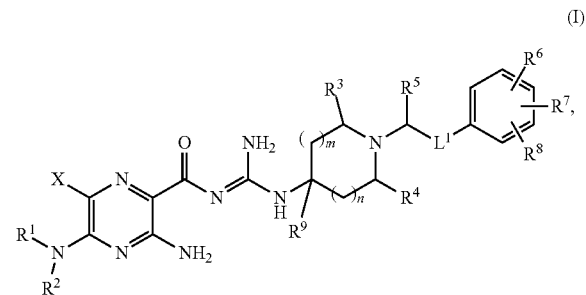

and the tautomers and the salts thereof, particularly the pharmaceutically acceptable salts thereof with inorganic or organic acids and bases, which have valuable pharmacological properties, particularly an inhibitory effect on epithelial sodium channels, the use thereof for the treatment of diseases, particularly diseases of the lungs and airways.

11 Claims, No Drawings

(56) References Cited

OTHER PUBLICATIONS

Rogister, Francoise, et al; Novel Inhibitors of the Sodium-Calcium Exchanger: Benzene Ring Analogues of N-Guanidino Substituted Amiloride Derivatives; European Journal of Medicinal Chemistry (2001) vol. 36, No. 7-8 pp. 597-614.

Shepard, Kenneth, L. et al; 3,5-Diamino-6-Chloropyrazinecarboxylic Acid "Active Esters" and Their Reactions (1); Tetrahedron Letters (1969) vol. 54 pp. 4757-4760.

Short, James, H. et al., Sympathetic Nervous System Blocking Agents. Derivates of Guanidine and Related Compounds; Journal of Medicinal Chemistry (1963) vol. 6 pp. 275-283.

U.S. Appl. No. 13/662,791, filed Oct. 29, 2012, InventorArmin Heckel.

U.S. Appl. No. 13/662,792, filed Oct. 29, 2012, Inventor Joerg Kley.

Laeckmann, D. et al., "Synthesis and Biological Evaluation of Aroylguanidines Related to Amilorade as Inhibitors of the Human Platelet Na+/H+Exchanger". Bioorganic Medical Chemistry 2002, 1793-1804.

Shepard, K.L., et al., Activated Esters of Substituted Pyrazinecarboxylic Acids (1). Journal of Heterocyclic Chemistry, 1976, 1219-1224.

Woodman, D.J., "N-t-Butyl -acyloxycrotonamides". Journal of Organic Chemistry, 1970, p. 83-87.

Alberola, A., et al., "The Reactions of 3-Unsubstituted Isoxazolium Salts with 1,2-Dinucleophiles, Synthesis of 4-Funtionalized 3-Aminoisoxazoles and 3-Aminopyrazoles". Synthesis 1988, 203-207.

International Search Report, Form PCT/ISR/210, for corresponding application PCT/EP2012/076101 date of mailing Jan. 22, 2013.

SUBSTITUTED PYRAZINES AND THEIR USE IN THE TREATMENT OF DISEASE

1. FIELD OF THE INVENTION

The present invention relates to compounds of general formula (I)

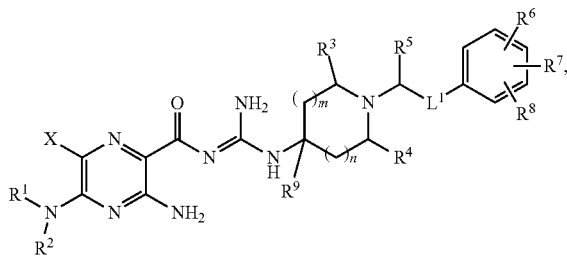

and the tautomers and the salts thereof, particularly the pharmaceutically acceptable salts thereof with inorganic or organic acids and bases, which have valuable pharmacological properties, particularly an inhibitory effect on epithelial sodium channels, the use thereof for the treatment of diseases, particularly diseases of the lungs and airways.

2. BACKGROUND TO THE INVENTION

Amiloride type compounds are known from the prior art as active substances for example for the treatment of diseases of the lungs and airways (*J. Med. Chem.* 49 (2006) 4098-4115). WO 08135557 discloses compounds of similar structure showing ENaC (Epithelial Sodium Channel) inhibitor activity.

The problem of the present invention is to prepare new compounds which may be used therapeutically for the treatment of pathophysiological processes treatable by the blockade of an epithelial sodium channel, particularly for the treatment of the lungs and airways.

3. DETAILED DESCRIPTION OF THE INVENTION

It has surprisingly been found that the problem mentioned above is solved by compounds of formula (I) of the present invention.

The present invention therefore relates to a compound of formula (I),

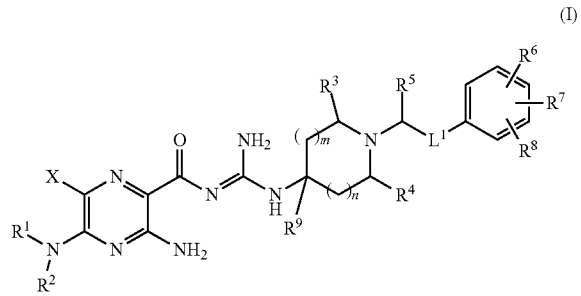

wherein
$R^1$ denotes H or $C_{1-4}$-alkyl,
$R^2$ denotes H or $C_{1-4}$-alkyl,
$R^3$ denotes H or methyl,
$R^4$ denotes H or methyl, or
$R^3$ and $R^4$ together form an ethylene bridge,
$R^5$ is selected from the group consisting of
  H, $C_{1-4}$-alkyl-O—CO—, $C_{1-4}$-alkyl-O—CO—$C_{1-4}$-alkyl-,
  $C_{1-4}$-alkyl-O—$C_{1-4}$-alkyl-, HO—CO— and HO—CO—$C_{1-4}$-alkyl-,
$R^6$ is selected from the group consisting of
  H, halogen, CN, $N_3$, $C_{1-4}$-alkyl-, which is optionally substituted by one or more F atoms,
  HC≡C—, OH, $C_{1-4}$-alkyl-O—, HO—$CH_2$—,
  $H_2C$=CH—$CH_2$—O—, HC≡C—$CH_2$—O— and —$NR^{6.1}R^{6.2}$,
  wherein,
  $R^{6.1}$ denotes H, $C_{1-4}$-alkyl-, $C_{1-4}$-alkyl-CO— or $C_{1-4}$-alkyl-$SO_2$—,
  $R^{6.2}$ denotes H or $C_{1-4}$-alkyl-,
$R^7$ is selected from the group consisting of
  H, halogen, CN, $N_3$, $C_{1-4}$-alkyl-, which is optionally substituted by one or more F atoms,
  HC≡C—, OH, $C_{1-4}$-alkyl-O—, HO—$CH_2$—,
  $H_2C$=CH—$CH_2$—O—, HC≡C—$CH_2$—O—,
  —$NR^{7.1}R^{7.2}$, $H_2N$—C(NH)—, $H_2N$—C(NH)NH—,
  $H_2N$—C(NH)NH—$CH_2$—, —COOH, $C_{1-4}$-alkyl-OCO—, —$C_{1-4}$-alkyl-COOH, alkyl, —$OCH_2$—COOH, —$OCH_2$—COO—$C_{1-4}$-alkyl, —P(O)($OR^{7.3}$)($OR^{7.4}$), —$CH_2$—P(O)($OR^{7.3}$)($OR^{7.4}$) and —B(OH)$_2$,
  wherein,
  $R^{7.1}$ denotes H, $C_{1-4}$-alkyl-, $C_{1-4}$-alkyl-CO— or $C_{1-4}$-alkyl-$SO_2$—,
  $R^{7.2}$ denotes H or $C_{1-4}$-alkyl-, or
  $R^{7.3}$, $R^{7.4}$ independently from each other denote H or $C_{1-4}$-alkyl,
$R^8$ is selected from the group consisting of
  H, halogen, CN, $N_3$, $C_{1-4}$-alkyl- which is optionally substituted by one or more F atoms,
  HC≡C—, OH, $C_{1-4}$-alkyl-O—, HO—$CH_2$—,
  $H_2C$=CH—$CH_2$—O—, HC≡C—$CH_2$—O—,
  —$NR^{8.1}R^{8.2}$,
  $H_2N$—C(NH)—, $H_2N$—C(NH)NH—, $H_2N$—C(NH)NH—$CH_2$—, —COOH, $C_{1-4}$-alkyl-OCO—, $C_{1-4}$-alkyl-COOH, —$C_{1-4}$-alkyl-COO—$C_{1-4}$-alkyl, —$OCH_2$—COOH, —$OCH_2$—COO—$C_{1-4}$-alkyl, —P(O)($OR^{8.3}$)($OR^{8.4}$), —$CH_2$—P(O)($OR^{8.3}$)($OR^{8.4}$) and —B(OH)$_2$, or
$R^8$ denotes -$L^2$-$Y^1$-$L^3$-$Y^2$-$L^4$-$R^{8.5}$
  wherein,
  $R^{8.1}$ denotes H, $C_{1-4}$-alkyl, $C_{1-4}$-alkyl-CO— or $C_{1-4}$-alkyl-$SO_2$—,
  $R^{8.2}$ denotes H or $C_{1-4}$-alkyl, or
  $R^{8.1}$ and $R^{8.2}$ together with the nitrogen atom they are attached to form a heterocycle $Y^3$,
  $R^{8.3}$, $R^{8.4}$ independently from each other denote H or $C_{1-4}$-alkyl,
  $R^{10}$, $R^{8.5}$ independently from each other are selected from the group consisting of H, halogen, CN, $N_3$, $C_{1-4}$-alkyl, HC≡C—, OH, $C_{1-4}$-alkyl-O—, HO—$CH_2$—, $H_2C$=CH—$CH_2$—O—, HC≡C—$CH_2$—O—, —$NR^{8.5.1}R^{8.5.2}$ B(OH)$_2$, $BF_3^-$, —S(O)$_2$OH, —O—C($C_6H_6$)$_3$, —C($CH_2OH$)$_3$, —CH($CH_2OH$)$_2$, —CH(OH)$CH_2OH$ and —$N^+(R^{8.5.3})_3$
  With the proviso that
    If at least one out of $Y^{1.1}$ and $Y^{2.1}$ is imidazole or pyridine then $R^{10}$, $R^{8.5}$ are not selected from the group consisting of B(OH)$_2$, $BF_3$ and —S(O)$_2$OH $R^{8.5.1}$ denotes H, $C_{1-4}$-alkyl, $C_{1-4}$-alkyl-CO— or $C_{1-4}$-alkyl-SO$_2$—, $R^{8.5.2}$ denotes H or $C_{1-4}$-alkyl, or $R^{8.5.1}$ and $R^{8.5.2}$ together with the nitrogen atom they are attached to form a heterocycle $Y^3$, $R^{8.5.3}$ denotes methyl or ethyl, $R^9$ denotes H or methyl, m, n independently from each other with the proviso that (m+n)<4, denote 0, 1 or 2, X denotes halogen, $L^1$ denotes a bond or is selected from the group consisting of —CH$_2$—, —CH$_2$—CH$_2$—, —CH$_2$O—, —CO—, —S—, —SO—, —SO$_2$—, —SO—CH$_2$— and —SO$_2$—CH$_2$, $L^2$ denotes a bond or is selected from the group consisting of —O—, —CH$_2$—, —CH$_2$—CH$_2$—, —CH$_2$—O—, —O—CH$_2$—, —CO—, —CH$_2$—CO, —CO—CH$_2$—, —S—, —SO—, —SO$_2$— and —O—CO—, $L^3$, $L^4$, $L^5$ independently from each other denote a bond or a linear chain of formula (m)

$$-(CH_2)_i-[O-(CH_2)_{g1}]_{p1}-[NH-(CH_2)_{g2}]_{p2}-[O-(CH_2)_{g3}]_{p3}- \quad (m),$$

wherein i denotes 0, 1, 2, 3 or 4, g1, g2, g3 independently from each other denote 2, 3 or 4, p1, p3 independently from each other denote 0, 1, 2, 3 or 4, p2 denotes 0 or 1, with the provisio that the linear chain is consisting of 1 to 15 moieties selected from the group consisting of —CH$_2$—, —O— and —NH— and with the proviso that the nitrogen atom of formula (m) is not directly linked to another nitrogen atom, $Y^1$ denotes a bond, $Y^{1.1}$ or —NR$^{Y1.1}$—, wherein, $R^{Y1.1}$ denotes $L^3$-H or $L^3$-NR$^{Y1.1.1}$R$^{Y1.1.1}$, wherein $R^{Y1.1.1}$ is selected from among H, $C_{1-4}$-alkyl-, $C_{1-4}$-alkyl-CO— and $C_{1-4}$-alkyl-SO$_2$—, $R^{Y1.1.2}$ denotes H or $C_{1-4}$-alkyl-, or $R^{Y1.1.1}$ and $R^{Y1.1.2}$ together with the nitrogen atom they are attached to form a heterocycle, $Y^3$, $Y^2$ denotes a bond or is selected from a group consisting of $Y^{2.1}$, —CO—, —NR$^{Y2.1}$—CO—, —CO—NR$^{Y2.1}$—, —Y$^{2.1}$—CONR$^{Y2.1}$—, —Y$^{2.1}$—CO— and —NR$^{Y2.1}$—CO—Y$^{2.1}$—, with the proviso that carbonyl moieties are not directly attached to nitrogen atoms of aromatic heterocycles, wherein $R^{Y2.1}$ denotes -$L^3$-H or -$L^3$-NR$^{Y2.1.1}$R$^{Y2.1.2}$, $R^{Y2.1.1}$ is selected from among H, $C_{1-4}$-alkyl-, $C_{1-4}$-alkyl-CO— and $C_{1-4}$-alkyl-SO$_2$—, $R^{Y2.1.2}$ denotes H or $C_{1-4}$-alkyl-, or $R^{Y2.1.1}$ and $R^{Y2.1.2}$ together with the nitrogen atom they are attached to form a heterocycle $Y^3$, $Y^{1.1}$, $Y^{2.1}$ independently from each other denote a linker in form of a phenylene group optionally substituted by -$L^5R^{10}$, or an optionally substituted heteroaromatic or heterocyclic moiety each containing at least one nitrogen atom, $Y^3$ denotes an optionally substituted 4-7-membered heterocycle containing at least one N-atom, and optionally in the form of the tautomers, the racemates, the enantiomers, the diastereomers and the mixtures thereof, optionally in form of the hydrates, solvates or prodrugs thereof and optionally the pharmacologically acceptable acid addition salts thereof, preferably, the pharmacologically acceptable acid addition salts thereof.

Preferred compounds of formula (I) are those wherein

X denotes Cl or Br, $Y^{1.1}$ $Y^{2.1}$ independently from each other denote a bond or are selected from a group consisting of a linker of formula (a) to (k)

(a)

(b)

(c)

(d)

(e)

(f)

(g)

(h)

(i)

(j)

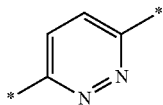
(k)

$Y^3$ denotes pyrrolidine or piperidine, each optionally substituted by up to two substituents independently selected from hydroxy or $C_{1-3}$-alkoxy, or $Y^3$ denotes morpholine, piperazine, 4-methyl-piperazine, 4-ethyl-piperazine, 4-acetylpiperazine or 4-propionyl-piperazine.

Particularly preferred are compounds of formula (I), wherein
$R^1, R^2, R^3, R^4, R^5$ denote H,
$R^9$ denotes H,
X denotes Cl,
$L^1$ denotes a bond, —$CH_2$—, —$CH_2O$— or —CO—, and
m, n independently from each other with the proviso that $0<(m+n)<4$, denote 0, 1 or 2,
$Y^3$ denotes morpholine, 4-acetyl-piperazine or 4-propionyl-piperazine.

Also particularly preferred are compounds of formula (I), wherein
$R^7$ is selected from the group consisting of
—COOH, —$CH_2$COOH, —$(CH_2)_2$COOH, —$OCH_2$—COOH, —$P(O)(R^{7.3})(OR^{7.4})$, —$CH_2$—$P(O)(OR^{7.3})(OR^{7.4})$ and —$B(OH)_2$,
wherein
$R^{7.3}$ denotes H,
$R^8$ is selected from the group consisting of
H, halogen, CN, HC≡C—, OH, $C_{1-4}$-alkyl-O—, HC≡C—, OH, $C_{1-4}$-alkyl-O—, HO—$CH_2$—, $H_2C$=CH—$CH_2$—O—, HC≡C—$CH_2$—O— and —$NR^{8.1}R^{8.2}$,
wherein
$R^{8.1}$ denotes H, $C_{1-4}$-alkyl-CO— or $C_{1-4}$-alkyl-$SO_2$—,
$R^{8.2}$ denotes H or $C_{1-4}$-alkyl-, or
$R^{8.1}$ and $R^{8.2}$ together with the nitrogen atom they are attached to form a heterocycle $Y^3$.

Also particularly preferred are compounds of formula (I), wherein
$R^7$ is selected from the group consisting of
$C_{1-4}$-alkyl-OCO—, —$C_{1-2}$-alkyl-COO—$C_{1-4}$-alkyl, —$OCH_2$—COO—$C_{1-4}$-alkyl, —$P(O)(OR^{7.3})(OR^{7.4})$, and —$CH_2$—$P(O)(OR^{7.3})(OR^{7.4})$,
wherein
$R^{7.3}, R^{7.4}$ independently from each other denote methyl, ethyl or 2-propyl,
$R^8$ is selected from the group consisting of
H, halogen, CN, $C_{1-4}$-alkyl-, HC≡C—, OH, $C_{1-4}$-alkyl-O—, HO—$CH_2$—, $H_2C$=CH—$CH_2$—O—, HC≡C—$CH_2$—O— and —$NR^{8.1}R^{8.2}$,
wherein
$R^{8.1}$ denotes H, $C_{1-4}$-alkyl-CO— or $C_{1-4}$-alkyl-$SO_2$—,
$R^{8.2}$ denotes H or $C_{1-4}$-alkyl-, or
$R^{8.1}$ and $R^{8.2}$ together with the nitrogen atom they are attached to form a heterocycle $Y^3$.

Also particularly preferred are compounds of formula (I), wherein
$L^3, L^4$ independently from each other denote a bond, —$CH_2$— or —$CH_2$—$CH_2$—,
$R^8$ denotes -$L^2$-$Y^1$-$L^3$-$Y^2$-$L^4$-$R^{8.5}$,
wherein
$R^{8.5}$ denotes —$NH_2$ or —$N^+(R^{8.5.3})_3$, $R^{8.5.3}$ denotes methyl or ethyl,
$R^{10}$ denotes a hydrogen atom,
With the proviso that if $Y^2$ denotes a bond, then $L^2$ denotes —CO— and $Y^1$ denotes —$NR^{Y1.1}$—.

Also particularly preferred are compounds of formula (I), wherein
$L^2$ denotes —$CH_2$—$CH_2$—,
$Y^1$ denotes $Y^{1.1}$,
wherein
$Y^{1.1}$ is selected from a group consisting of linkers of formula (c), (d), (e), (f) and (k)

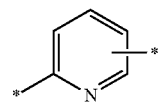
(c)

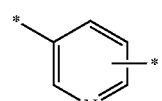
(d)

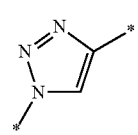
(e)

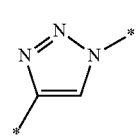
(f)

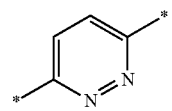
(k)

with the proviso that $L^3$ is not a bond.

Especially preferred are compounds of formula (I), wherein
$R^7$ is selected from the group consisting of
H, halogen, CN, $C_{1-4}$-alkyl-, OH, $C_{1-4}$-alkyl-O— and HO—$CH_2$—,
$R^{8.5}$ is selected from the group consisting of H, OH, $C_{1-4}$-alkyl-O—, —$C(CH_2OH)_3$, —$CH(CH_2OH)_2$ and —$CH(OH)CH_2OH$,
$L^2$ denotes a bond, —$CH_2$—$CH_2$— or —O—$CH_2$—,
$L^3$ denotes a bond,
$L^4$ denotes a linear chain of formula (m.1):

$$—(CH_2)_i—[O—(CH_2)_{g1}]_{p1}— \quad (m.1),$$

wherein
i denotes 0, 1, 2, or 3,
g1 denotes 2, or 3,
p1 denotes 0, 1 or 2,
With the proviso that if $R^{8.5}$ denotes OH or $C_{1-4}$-alkyl-O—, then $(i+p1)>0$, and with the proviso that if $R^{8.5}$ denotes H, then $p1>0$,
and with the proviso that the linear chain or formula (m.1) is consisting of no more than 8 moieties selected from the group consisting of —$CH_2$— and —O—.
$Y^1$ denotes a bond,
$Y^2$ denotes —CO—NH— or $Y^{2.1}$,
wherein $Y^{2.1}$ is selected from a group consisting of linkers of formula (c), (d), (e), (f) and (k)

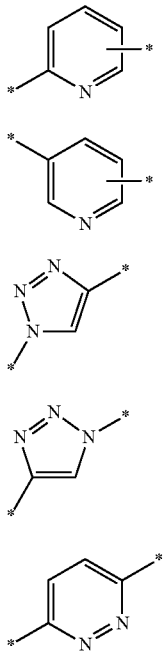

(c)

(d)

(e)

(f)

(k)

Also especially preferred are compounds of formula (I), wherein
$L^2$ denotes a bond,
$L^3$, $L^4$ independently from each other denote a bond or a linear chain of formula (m)

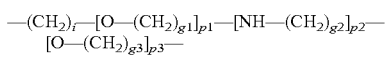

(m), wherein
i denotes 0, 1, 2 or 3,
g1 denotes 2, 3 or 4,
g2 denotes 0,
g3 denotes 2, or 3,
p1 denotes 0 or 1,
p3 denotes 2, 3 or 4,
p2 denotes 0,
with the proviso that the linear chain is consisting of 5 to 12 moieties selected from the group consisting of —$CH_2$— and —O—, and
with the proviso that $L^3$ and $L^4$ together consist of at least eight —$CH_2$— moieties and of at least four —O— moieties,
$Y^1$ denotes $Y^{1.1}$,
wherein
$Y^{1.1}$ denotes a linker of formula (e) or (f)

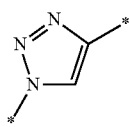

(e)

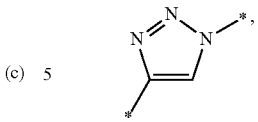

(f)

$Y^2$ denotes a bond or
is selected from a group consisting of $Y^{2.1}$, —$Y^{2.1}$—$CONR^{Y2.1}$— and —$NR^{Y2.1}$—CO—$Y^{2.1}$—,
$R^{8.5}$ denotes H, OH or —$OCH_3$,
Also preferred are compounds of formula (I), wherein
$R^1$, $R^2$, $R^3$, $R^4$, $R^5$ denote H,
$R^7$ denotes H or halogen,
$R^9$ denotes H,
X denotes Cl,
is $L^1$ denotes a bond,
m, n denote 1,
$L^2$ denotes —CO— or —$SO_2$—,
$Y^1$—$NR^{Y1.1}$,
wherein,
$R^{Y1.1}$ denotes hydrogen,
Also preferred are compounds of formula (I), wherein
$R^1$, $R^2$, $R^3$, $R^4$, $R^5$ denote H,
$R^7$ denotes H or halogen,
$R^9$ denotes H,
X denotes Cl,
$L^1$ denotes a bond,
m, n denote 1,
$L^2$ denotes a bond,
$Y^1$ denotes $Y^{1.1}$,
wherein
$Y^{1.1}$ is selected from a group consisting of linkers of formula (e) and (f)

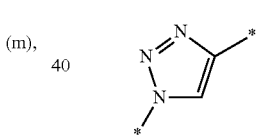

(e)

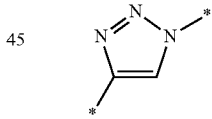

(f)

A further embodiment of the current invention are compounds of formula (I), or a pharmaceutically acceptable salt thereof for use as a medicament.

A further embodiment of the current invention are compounds of formula (I), or a pharmaceutically acceptable salt thereof for use in the treatment of a disease selected from among respiratory diseases or complaints and allergic diseases of the airways.

Preferred are compounds of formula (I) or a pharmaceutically acceptable salt thereof for use in the treatment of a disease selected from among chronic bronchitis, acute bronchitis, bronchitis caused by bacterial or viral infection or fungi or helminths, allergic bronchitis, toxic bronchitis, chronic obstructive pulmonary disease (COPD), asthma (intrinsic or allergic), paediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema and pneumonitis of different origins, preferably chronic bronchitis, acute bronchitis, bronchitis, chronic obstructive bronchitis (COPD), asthma (intrinsic or allergic), cystic fibrosis and paediatric asthma, preferably chronic bronchitis, COPD and cystic fibrosis.

A further embodiment of the current invention is a pharmaceutical composition comprising at least one compound according to the invention or a pharmaceutically acceptable salt thereof and a pharmaceutically acceptable carrier.

A further embodiment of the current invention are medicament combinations which contain, besides one or more compounds of a compound according to the invention, as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators or double or triple combinations thereof, preferably VX-770 and VX-809, or double or triple combinations thereof.

4. USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, OS, $O_2S$, NC (cyano), HOOC, $F_3C$ or the like, the skilled artisan can see the radical attachment point(s) to the molecule from the free valences of the group itself. For combined groups comprising two or more subgroups, the terminal bond indicates the radical attachment point, for example, the substituent "aryl-$C_{1-3}$-alkyl-" means an aryl is group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk is may be used in sub-formulas to indicate the bond which is connected to the core molecule as defined.

For example, the term "3-carboxypropyl-group" represents the following substituent:

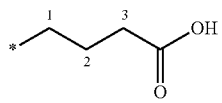

wherein the carboxy group is attached to the third carbon atom of the propyl group. The terms "1-methylpropyl-", "2,2-dimethylpropyl-" or "cyclopropylmethyl-" group represent the following groups:

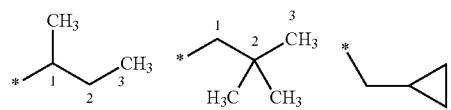

The asterisk may be used in sub-formulas to indicate the bond which is connected to the core molecule as defined.

Many of the following terms may be used repeatedly in the definition of a formula or group and in each case have one of the meanings given above, independently of one another.

Unless specifically indicated, according to the invention a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2''-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxyethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent is like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring systems including aromatic ring system containing one or more heteroatoms selected from N, O or S(O) wherein r=0, 1 or 2, consisting of 3 to 14 ring atoms wherein none of the heteroatoms is part of the aromatic ring. The term "heterocycle" is intended to include all the possible isomeric forms.

Thus, the term "heterocyclyl" includes the following exemplary structures which are not depicted as radicals as each form may be attached through a covalent bond to any atom so long as appropriate valences are maintained:

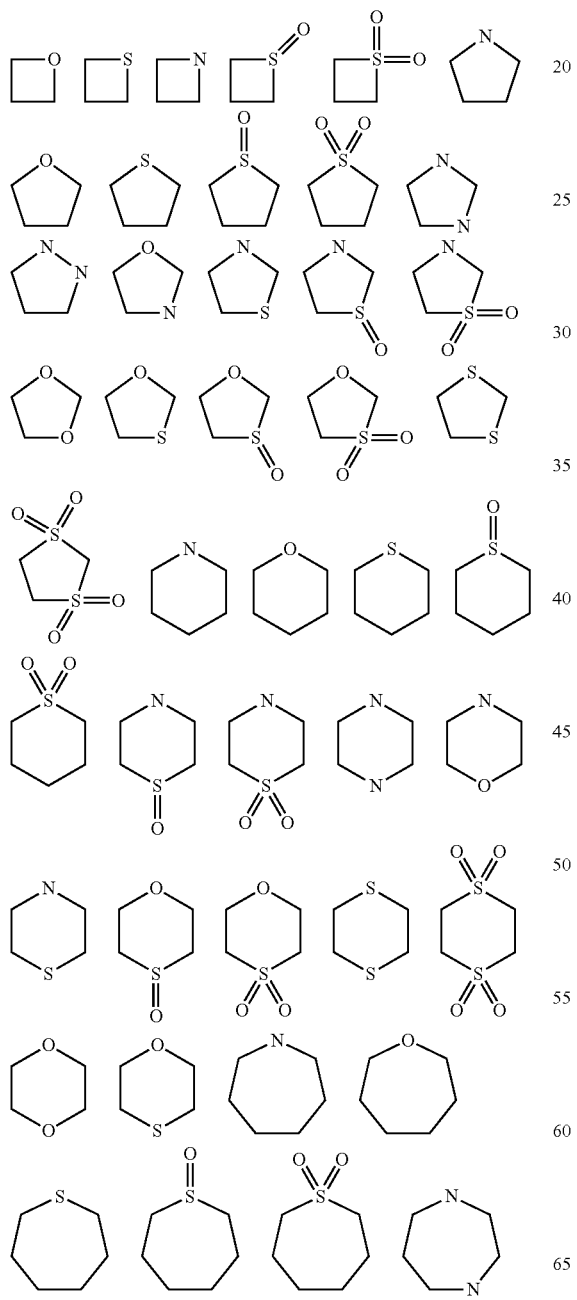

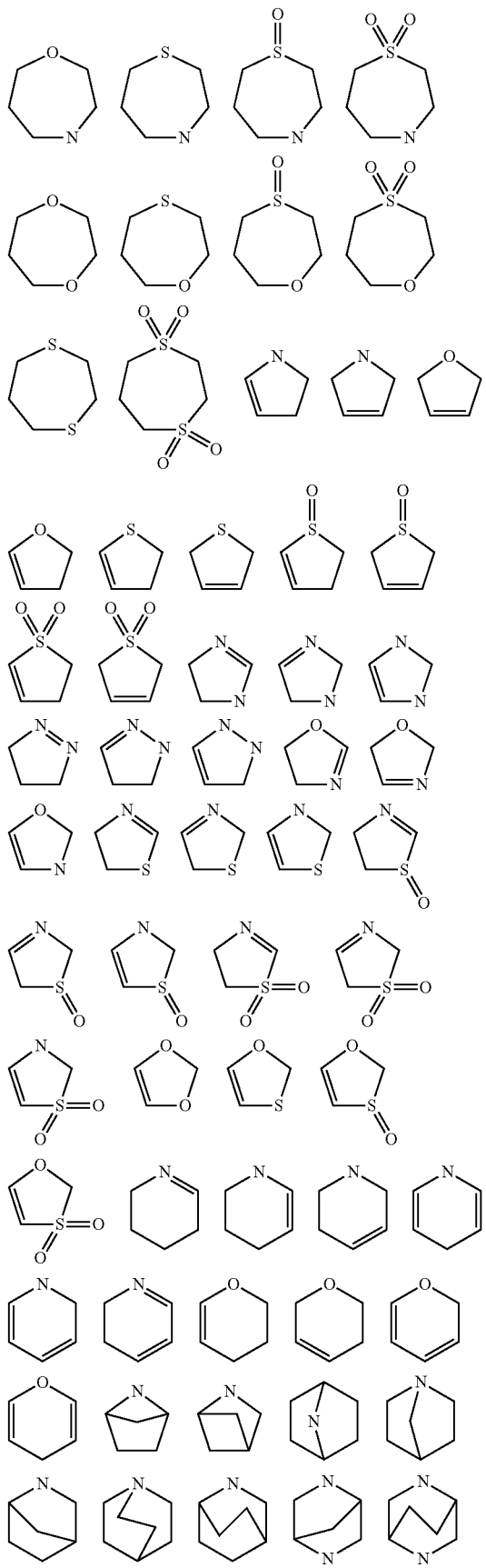

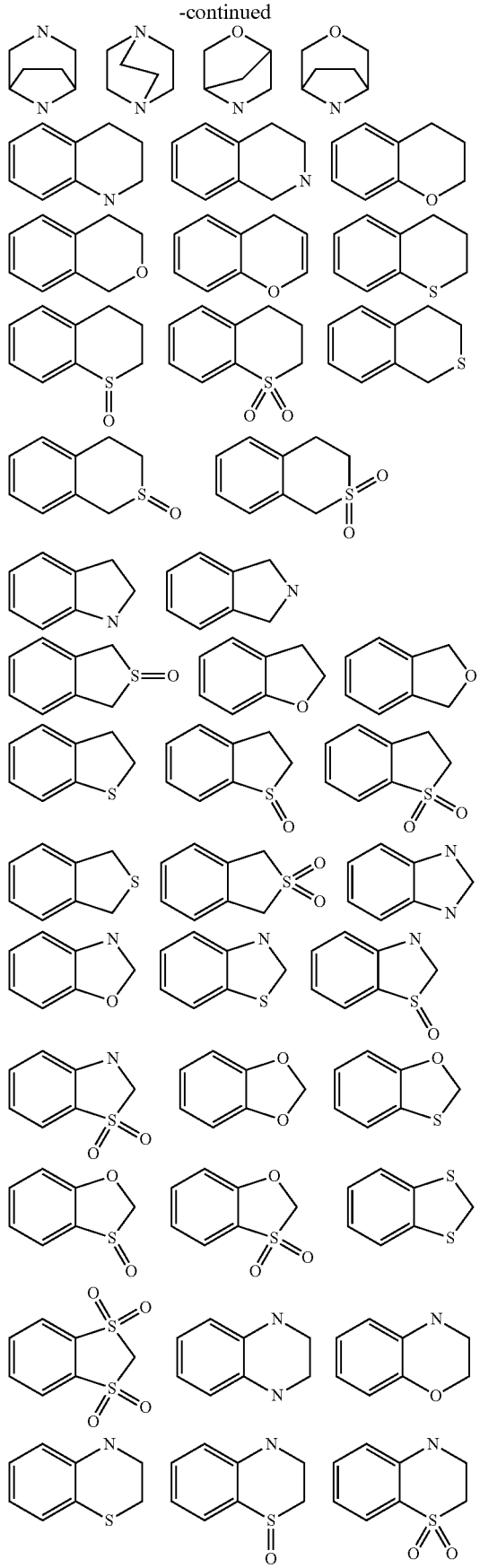
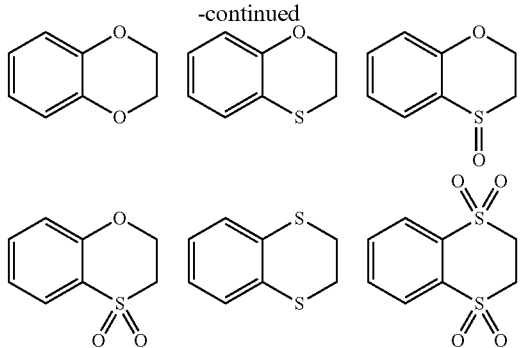

The term heteroaromatic means heteroaryl, monocyclic $C_{5-6}$-heteroaryl, or monocyclic $C_{5-6}$-heteroaryl.

The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

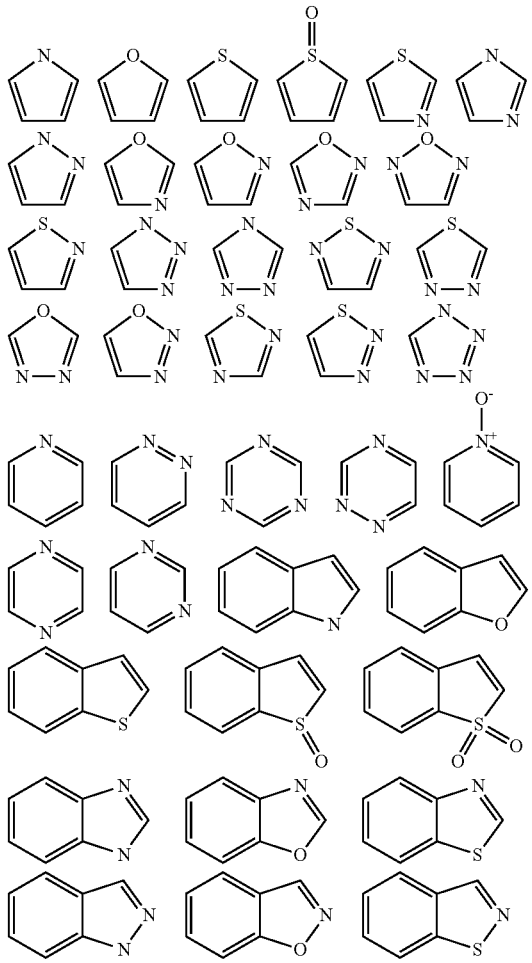

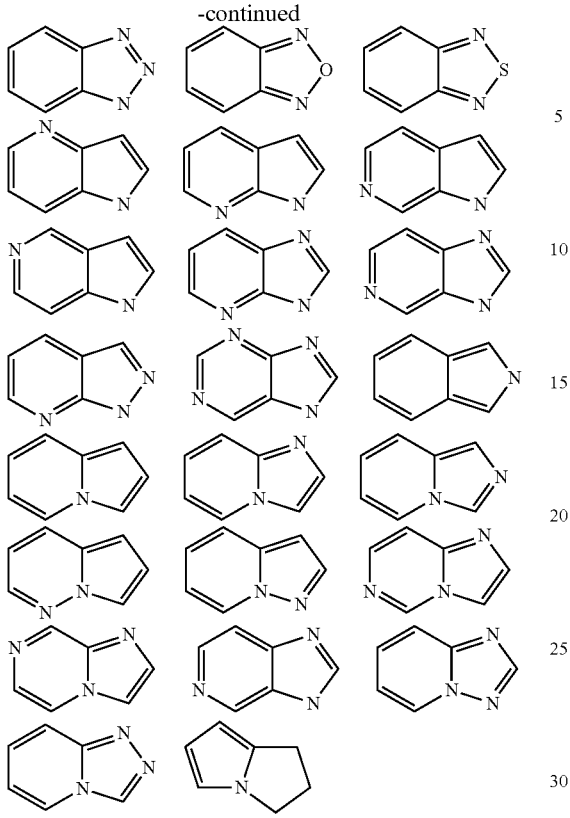

The term "monocyclic $C_{5-7}$-heterocyclyl" means a saturated or unsaturated non-aromatic monocyclic-ring systems containing one or more heteroatoms selected from N, O or $S(O)_r$, wherein r=0, 1 or 2, consisting of 5 to 7 ring atoms. The term "monocyclic $C_{5-7}$-heterocyclyl" is intended to include all the possible isomeric forms.

Thus, the term "monocyclic $C_{5-7}$-heterocyclyl" includes the following exemplary structures which are not depicted as radicals as each form may be attached through a covalent bond to any atom so long as appropriate valences are maintained:

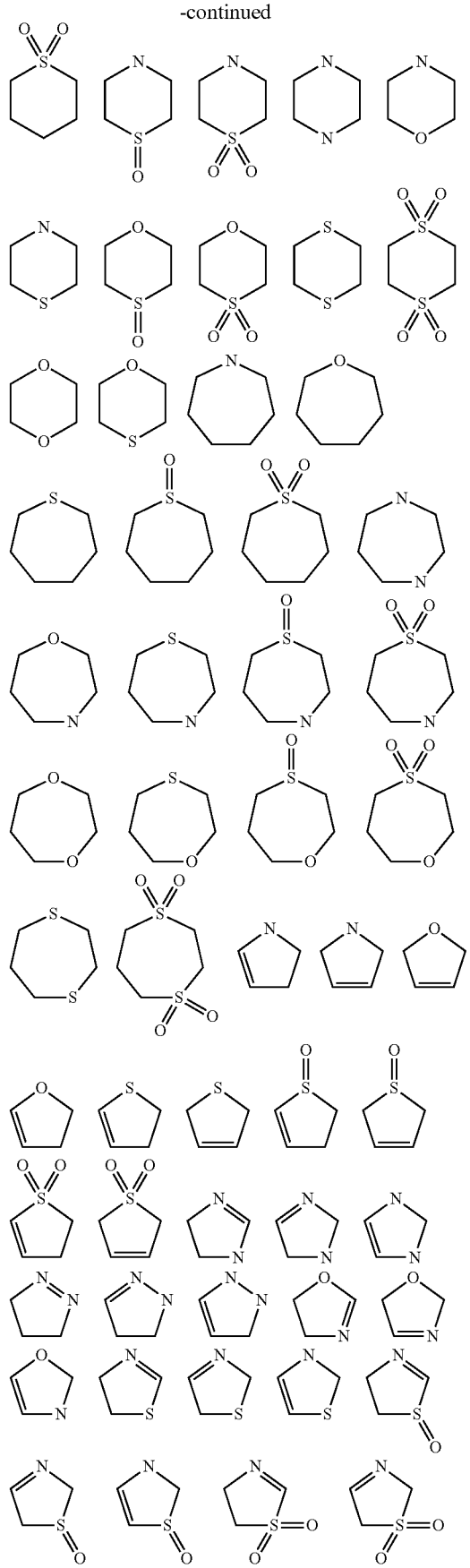

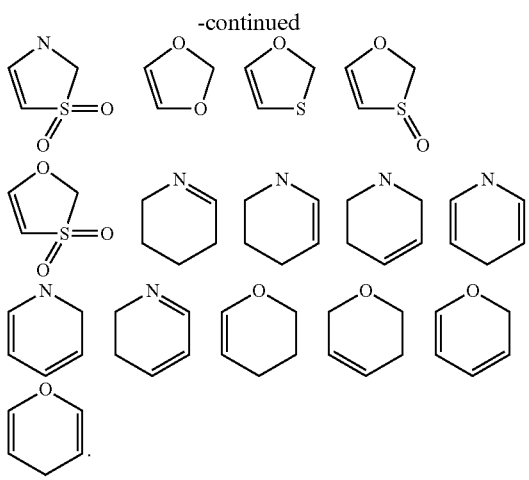

The term "monocyclic $C_{5-6}$-heteroaryl" means a monocyclic-ring systems containing one or more heteroatoms selected from N, O or $S(O)_r$, wherein r=0, 1 or 2, consisting of 5 or 6 ring atoms wherein at least one of the heteroatoms is part of aromatic ring. The term "monocyclic $C_{5-6}$-heteroaryl" is intended to include all the possible isomeric forms.

Thus, the term "monocyclic $C_{5-6}$-heteroaryl" includes the following exemplary structures which are not depicted as radicals as each form may be attached through a covalent bond to any atom so long as appropriate valences are maintained:

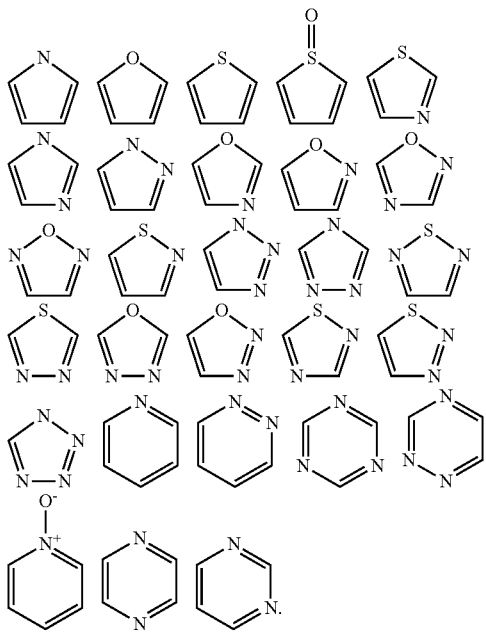

The term "bicyclic $C_{8-10}$-heterocyclyl" means a saturated or unsaturated bicyclic-ring systems including aromatic ring systems containing one or more heteroatoms selected from N, O or $S(O)_r$, wherein r=0, 1 or 2, consisting of 8 to 10 ring atoms wherein the heteroatoms is optionally part of the aromatic ring. The term "bicyclic $C_{8-10}$-heterocyclyl" is intended to include all the possible isomeric forms.

Thus, the term "bicyclic $C_{8-10}$-heterocyclyl" includes the following exemplary structures which are not depicted as radicals as each form may be attached through a covalent bond to any atom so long as appropriate valences are maintained:

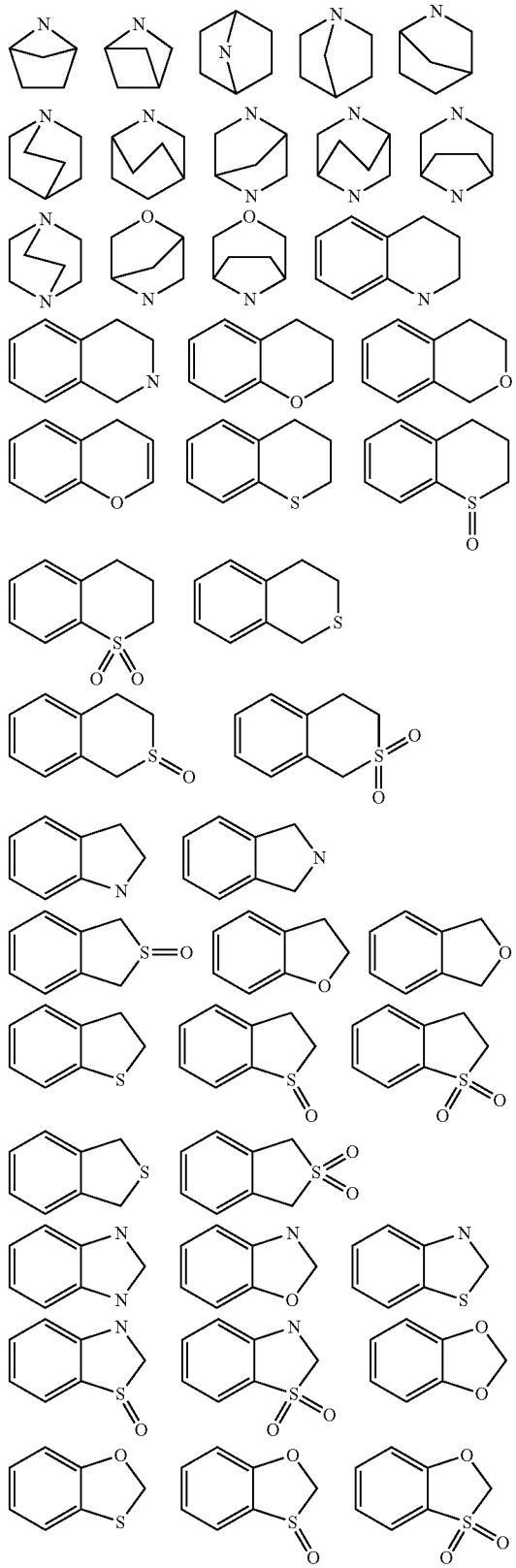

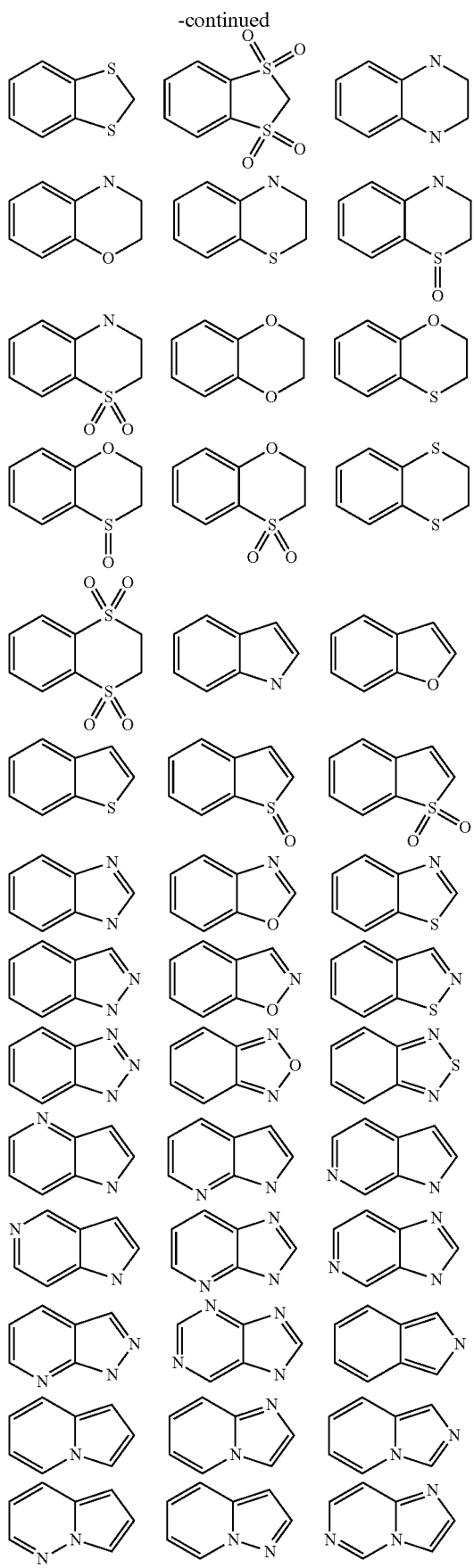

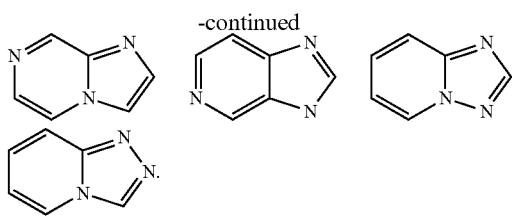

The term "annelated species of aryl or heterocyclyl" as used herein, either alone or in combination with another substituent wherein the annelated species presents as an aryl-het (a), a het-aryl (b) or a het-het (c) annelation means a monovalent substituent derived by removal of one hydrogen from an aromatic monocyclic system or aromatic multicyclic systems containing carbon atoms, which is annelated to a five-, six- or seven-membered saturated or unsaturated (including aromatic) heterocycle containing carbon atoms and one, two, three or four ring heteroatoms selected from is nitrogen, oxygen and sulfur or a five-, six-, or seven-membered saturated or unsaturated (including aromatic) heterocycle containing carbon atoms and one, two, three or four ring heteroatoms selected from nitrogen, oxygen and sulfur, which is annelated to an aromatic monocyclic system or aromatic multicyclic systems containing carbon atoms or a five-, six-, or seven-membered saturated or unsaturated (including aromatic) heterocycle containing carbon atoms and one, two, three or four ring heteroatoms selected from nitrogen, oxygen and sulfur, which is annelated to a five-, six-, or seven-membered saturated or unsaturated (including aromatic) heterocycle containing carbon atoms and one, two, three or four ring heteroatoms selected from nitrogen, oxygen and sulfur.

Suitable examples of a annelated species of aryl or het include: quinolinyl, 1-indoyl, 3-indoyl, 5-indoyl, 6-indoyl, indolizinyl, benzimidazyl or purinyl.

The term "halogen" as used herein means a halogen substituent selected from fluoro, chloro, bromo or iodo.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H₃C—, H₃C—CH₂—, H₃C—CH₂—CH₂—, H₃C—CH(CH₃)—, H₃C—CH₂—CH₂—CH₂—, H₃C—CH₂—CH(CH₃)—, H₃C—CH(CH₃)—CH₂—, H₃C—C(CH₃)₂—, H₃C—CH₂—CH₂—CH₂—CH₂—, H₃C—CH₂—CH₂—CH(CH₃)—, H₃C—CH₂—CH(CH₃)—CH₂—, H₃C—CH(CH₃)—CH₂—CH₂—, H₃C—CH₂—C(CH₃)₂—, H₃C—C(CH₃)₂—CH₂—, H₃C—CH(CH₃)—CH(CH₃)— and H₃C—CH₂—CH(CH₂CH₃)—.

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes —CH₂—, —CH₂—CH₂—, —CH(CH₃)—, —CH₂—CH₂—CH₂—, —C(CH₃)₂—, —CH(CH₂CH₃)—, —CH(CH₃)—CH₂—, —CH₂—CH(CH₃)—, —CH₂—CH₂—CH₂—CH₂—, —CH₂—CH₂—CH(CH₃)—, —CH(CH₃)—CH₂—CH₂—, —CH₂—CH(CH₃)—CH₂—, —CH₂—C(CH₃)₂—, —C(CH₃)₂—CH₂—, —CH(CH₃)—CH(CH₃)—, —CH₂—CH(CH₂CH₃)—, —CH(CH₂CH₃)—CH₂—, —CH(CH₂CH₂CH₃)—, —CH(CH(CH₃)₂)— and —C(CH₃)(CH₂CH₃)—.

The term "$C_{2-n}$-alkenyl", is used for a group as defined in the definition for "$C_{1-n}$-alkyl" with at least two carbon atoms, if at least two of those carbon atoms of said group are bonded to each other by a double bond.

The term "$C_{2-n}$-alkenylene" is used for a group as defined in the definition for "$C_{1-n}$-alkylene" with at least two carbon atoms, if at least two of those carbon atoms of said group are bonded to each other by a double bond.

The term "$C_{2-n}$-alkynyl", is used for a group as defined in the definition for "$C_{1-n}$-alkyl" with at least two carbon atoms, if at least two of those carbon atoms of said group are bonded to each other by a triple bond.

The term "$C_{2-n}$-alkynylene" is used for a group as defined in the definition for "$C_{1-n}$-alkylene" with at least two carbon atoms, if at least two of those carbon atoms of said group are bonded to each other by a triple bond.

By the term "$C_{1-6}$-alkoxy" (including those which are part of other groups) are meant branched and unbranched alkoxy groups with 1 to 6 carbon atoms and by the term "$C_{1-4}$-alkoxy" are meant branched and unbranched alkoxy groups with 1 to 4 carbon atoms. Alkoxy groups with 1 to 4 carbon atoms are preferred. Examples include: methoxy, ethoxy, propoxy, butoxy or pentoxy. The abbreviations OMe, OEt, OPr, etc. may optionally be used for the above-mentioned groups. Unless stated otherwise, the definitions propoxy, butoxy and pentoxy include all the possible isomeric forms of the respective groups. Thus for example propoxy includes n-propoxy and iso-propoxy, butoxy includes iso-butoxy, sec-butoxy and tert-butoxy etc.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "$C_{3-n}$-cycloalkenyl", wherein n is an integer 3 to n, either alone or in combination with another radical, denotes an cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl cycloheptadienyl and cycloheptatrienyl.

In all cases of contradictions between structure and their naming, structure shall prevail.

5. PREFERRED EMBODIMENTS

The substituent $R^1$ denotes H or $C_{1-4}$-alkyl, preferably methyl or H, particularly preferred hydrogen.

The substituent $R^2$ denotes H or $C_{1-4}$-alkyl, preferably methyl or H, particularly preferred hydrogen.

The substituent $R^3$ denotes H or methyl, preferably hydrogen.

The substituent $R^4$ denotes H or methyl, preferably hydrogen, or the substituents $R^3$ and $R^4$ together form an ethylene bridge, preferably if m=n=1.

The substituent $R^5$ is selected from the group consisting of
H, $C_{1-4}$-alkyl-O—CO—, $C_{1-4}$-alkyl-O—CO—$C_{1-4}$-alkyl-, $C_{1-4}$-alkyl-O—$C_{1-4}$-alkyl-, HO—CO— and HO—CO—$C_{1-4}$-alkyl-,
preferably H, $C_{1-4}$-alkyl-O—CO— and $C_{1-4}$-alkyl, particularly preferred H.

The substituent $R^6$ is selected from the group consisting of
H, halogen, CN, $N_3$, $C_{1-4}$-alkyl-, which is optionally substituted by one or more F atoms, HC≡C—, OH, $C_{1-4}$-alkyl-O—, HO—CH$_2$—, H$_2$C=CH—CH$_2$—O—, HC≡C—CH$_2$—O— and —NR$^{6.1}$R$^{6.2}$,
preferably H, halogen, CN, $C_{1-4}$-alkyl-, OH, $C_{1-4}$-alkyl-O—, HO—CH$_2$—, and —NR$^{6.1}$R$^{6.2}$, particularly preferred H, halogen, CN, CH$_3$-alkyl-, OH, and CH$_3$-alkyl-O—,
wherein,
$R^{6.1}$ denotes H, $C_{1-4}$-alkyl-, $C_{1-4}$-alkyl-CO— or $C_{1-4}$-alkyl-SO$_2$—, preferably H, $C_{1-2}$-alkyl-, $C_{1-2}$-alkyl-CO— or $C_{1-2}$-alkyl-SO$_2$—, particularly preferred $C_{1-2}$-alkyl-CO— or $C_{1-2}$-alkyl-SO$_2$—,
$R^{6.2}$ denotes H or $C_{1-4}$-alkyl-, preferably H or CH$_3$-alkyl-, particularly preferred H.

The substituent $R^7$ is selected from the group consisting of
H, halogen, CN, $N_3$, $C_{1-4}$-alkyl- which is optionally substituted by one or more F atoms, HC≡C—, OH, $C_{1-4}$-alkyl-O—, HO—CH$_2$—, H$_2$C=CH—CH$_2$—O—, HC≡C—CH$_2$—O—, —NR$^{7.1}$R$^{7.2}$, H$_2$N—C(NH)—, H$_2$N—C(NH)NH—, H$_2$N—C(NH)NH—CH$_2$—, —COOH, $C_{1-4}$-alkyl-OCO—, $C_{1-4}$-alkyl-COOH, —$C_{1-4}$-alkyl-COO—$C_{1-4}$-alkyl, —OCH$_2$—COOH, —OCH$_2$—COO—$C_{1-4}$-alkyl, —P(O)(OR$^{7.3}$)(OR$^{7.4}$), —CH$_2$—P(O)(OR$^{7.3}$)(OR$^{7.4}$) and —B(OH)$_2$,
preferably H, halogen, CN, $C_{1-4}$-alkyl-, OH, $C_{1-2}$-alkyl-O—, HO—CH$_2$—, —NR$^{7.1}$R$^{7.2}$, H$_2$N—C(NH)—, H$_2$N—C(NH)NH—, H$_2$N—C(NH)NH—CH$_2$—, —COOH, $C_{1-4}$-alkyl-OCO—, —CH$_2$COOH, —(CH$_2$)$_2$COOH, —CH$_2$COO—$C_{1-4}$-alkyl, —(CH$_2$)$_2$COO—$C_{1-4}$-alkyl, —OCH$_2$—COOH, —OCH$_2$—COO—$C_{1-4}$-alkyl, —P(O)(OR$^{7.3}$)(OR$^{7.4}$), —CH$_2$—P(O)(OR$^{7.3}$)(OR$^{7.4}$) and —B(OH)$_2$,
particularly preferred H, halogen, CN, CH$_3$-alkyl-, OH, CH$_3$-alkyl-O—, H$_2$N—C(NH)—, —COOH, $C_{1-4}$-alkyl-OCO—, CH$_2$COOH, —(CH$_2$)$_2$COOH, —CH$_2$COO—$C_{1-2}$-alkyl, —(CH$_2$)$_2$COO—$C_{1-2}$-alkyl, —OCH$_2$—COOH, —OCH$_2$—COO—$C_{1-2}$-alkyl, —P(O)(OR$^{7.3}$)(OR$^{7.4}$), —CH$_2$—P(O)(OR$^{7.3}$)(OR$^{7.4}$) and —B(OH)$_2$,
wherein,
$R^{7.1}$ denotes H, $C_{1-4}$-alkyl-, $C_{1-4}$-alkyl-CO— or $C_{1-4}$-alkyl-SO$_2$—, preferably H, $C_{1-2}$-alkyl-, $C_{1-2}$-alkyl-CO— or $C_{1-2}$-alkyl-SO$_2$—, particularly preferred $C_{1-2}$-alkyl-CO— or $C_{1-2}$-alkyl-SO$_2$—,
$R^{7.2}$ denotes H or $C_{1-4}$-alkyl-, preferably H or CH$_3$-alkyl-, particularly preferred H or
$R^{7.3}$, $R^{7.4}$ independently from each other denote H or $C_{1-4}$-alkyl, preferably H, methyl, ethyl or 2-propyl, particularly preferred H, methyl or ethyl.

The substituent $R^8$ is selected from the group consisting of
H, halogen, CN, $N_3$, $C_{1-4}$-alkyl- which is optionally substituted by one or more F atoms, HC≡C—, OH, $C_{1-4}$-alkyl-O—, HO—CH$_2$—, H$_2$C=CH—CH$_2$—O—, HC≡C—CH$_2$—O—, —NR$^{8.1}$R$^{8.2}$, H$_2$N—C(NH)—, H$_2$N—C(NH)NH—, H$_2$N—C(NH)NH—CH$_2$—, —COOH, $C_{1-4}$-alkyl-OCO—, —$C_{1-4}$-alkyl-COOH, —$C_{1-4}$-alkyl-COO—$C_{1-4}$-alkyl, —OCH$_2$—COOH, —OCH$_2$—COO—$C_{1-4}$-alkyl, —P(O)(OR$^{8.3}$)(OR$^{8.4}$), —CH$_2$—P(O)(OR$^{8.3}$)(OR$^{8.4}$) and —B(OH)$_2$,
preferably H, halogen, CN, $C_{1-4}$-alkyl-, OH, $C_{1-4}$-alkyl-O—, HO—CH$_2$—, —NR$^{8.1}$R$^{8.2}$, H$_2$N—C(NH)—, H$_2$N—C(NH)NH—, H$_2$N—C(NH)NH—CH$_2$—, —COOH, $C_{1-4}$-alkyl-OCO—, CH$_2$COOH, —(CH$_2$)$_2$COOH, —CH$_2$COO—$C_{1-4}$-alkyl, —(CH$_2$)$_2$COO—$C_{1-4}$-alkyl, —OCH$_2$—COON and —OCH$_2$—COO—$C_{1-4}$-alkyl,
particularly preferred H, halogen, CN, CH$_3$-alkyl-, OH, CH$_3$-alkyl-O—, —COOH, $C_{1-2}$-alkyl-OCO—, CH$_2$COOH, —(CH$_2$)$_2$COOH, —CH$_2$COO—C$_{1-2}$-alkyl, —(CH$_2$)$_2$COO—C$_{1-2}$-alkyl, —OCH$_2$COOH and —OCH$_2$—COO—C$_{1-2}$-alkyl, or R$^8$ denotes -L$^2$-Y$^1$-L$^3$-Y$^2$-L$^4$-R$^{8.5}$ wherein, R$^{8.1}$ denotes H, C$_{1-4}$-alkyl, C$_{1-4}$-alkyl-CO— or C$_{1-4}$-alkyl-SO$_2$—, preferably H, C$_{1-2}$-alkyl-, C$_{1-2}$-alkyl-CO— or C$_{1-2}$-alkyl-SO$_2$—, particularly preferred C$_{1-2}$-alkyl-CO— or C$_{1-2}$-alkyl-SO$_2$—, R$^{8.2}$ denotes H or C$_{1-4}$-alkyl preferably H or CH$_3$-alkyl-, particularly preferred H or R$^{8.1}$ and R$^{8.2}$ together with the nitrogen atom they are attached to form a heterocycle Y$^3$, preferably pyrrolidine, piperidine, piperazine, 4-methylpiperazine, 4-acetylpiperazine or morpholine, particularly preferred piperazine, 4-methylpiperazine, 4-acetylpiperazine or morpholine, R$^{8.3}$, R$^{8.4}$ independently from each other denote H or C$_{1-4}$-alkyl, preferably H, methyl, ethyl or 2-propyl, particularly preferred H, methyl or ethyl, R$^{10}$, R$^{8.5}$ independently from each other are selected from the group consisting of H, halogen, CN, N$_3$, C$_{1-4}$-alkyl, HC≡C—, OH, C$_{1-4}$-alkyl-O—, HO—CH$_2$—, H$_2$C═CH—CH$_2$—O—, HC≡C—CH$_2$—O—, —NR$^{8.5.1}$R$^{8.5.2}$, B(OH)$_2$, BF$_3^-$, —S(O)$_2$OH, —O—C(C$_6$H$_6$)$_3$, —C(CH$_2$OH)$_3$, —CH(CH$_2$OH)$_2$, —CH(OH)CH$_2$OH and —N$^+$(R$^{8.5.3}$)$_3$, preferably H, halogen, CN, C$_{1-4}$-alkyl, OH, C$_{1-4}$-alkyl-O—, HO—CH$_2$—, —NR$^{8.5.1}$R$^{8.5.2}$, B(OH)$_2$, BF$_3^-$, —S(O)$_2$OH, —C(CH$_2$OH)$_3$, —CH(CH$_2$OH)$_2$, —CH(OH)CH$_2$OH and —N$^+$(R$^{8.5.3}$)$_3$, particularly preferred H, CN, C$_{1-2}$-alkyl, OH, C$_{1-2}$-alkyl-O—, B(OH)$_2$, BF$_3^-$, —S(O)$_2$OH, —C(CH$_2$OH)$_3$, —CH(CH$_2$OH)$_2$, —CH(OH)CH$_2$OH and —N$^+$R$^{8.5.3}$)$_3$, R$^{8.5.1}$ denotes H, C$_{1-4}$-alkyl, C$_{1-4}$-alkyl-CO— or C$_{1-4}$-alkyl-SO$_2$—, preferably H, C$_{1-2}$-alkyl-, C$_{1-2}$-alkyl-CO— or C$_{1-2}$-alkyl-SO$_2$—, particularly preferred C$_{1-2}$-alkyl-CO— or C$_{1-2}$-alkyl-SO$_2$ R$^{8.5.2}$ denotes H or C$_{1-4}$-alkyl, preferably H or CH$_3$-alkyl-, particularly preferred H, or R$^{8.5.1}$ and R$^{8.5.2}$ together with the nitrogen atom they are attached to form an optionally substituted 4-7-membered heterocycle containing at least one N-atom, preferably pyrrolidine, piperidine, piperazine, 4-methylpiperazine, 4-acetylpiperazine or morpholine, particularly preferred piperazine, 4-methylpiperazine, 4-acetylpiperazine or morpholine, R$^{8.5.3}$ denotes methyl or ethyl, preferably methyl.

The substituent R$^9$ denotes H or methyl, preferably H.

Variables m, n independently from each other with the proviso that (m+n)<4, denote 0, 1 or 2, preferably with the proviso that 0<(m+n)<4 denote 0, 1 or 2, particularly preferred denote m=n=1, The symbol X denotes halogen, preferably Cl or Br, particularly preferred Cl.

The symbol L' denotes a bond or is selected from the group consisting of

—CH$_2$—, —CH$_2$—CH$_2$—, —CH$_2$O—, —CO—, —S—, —SO—, SO—CH$_2$— and —SO$_2$—CH$_2$, preferably bond, —CH$_2$—, —CH$_2$O— and —CO—, particularly preferred a bond.

The symbol L$^2$ denotes a bond or is selected from the group consisting of —O—, —CH$_2$—, —CH$_2$—CH$_2$—, —CH$_2$—O—, —O—CH$_2$—, —CO—, —S—, —SO—, —SO$_2$— and —O—CO—, preferably a bond, —O—, —CH$_2$—, —CH$_2$—CH$_2$—, —CH$_2$—O—, —O—CH$_2$—, —CO— and —SO$_2$—, particularly preferred a bond, —CH$_2$—, —CH$_2$—CH$_2$—, —CO— and —SO$_2$—.

The symbols L$^3$, L$^4$, L$^5$ independently from each other denote a bond or a linear chain of formula (m), —(CH$_2$)$_i$—[O—(CH$_2$)$_{g1}$]$_{p1}$—[NH—(CH$_2$)$_{g2}$]$_{p2}$—[O(CH$_2$)$_{g3}$]$_{p3}$ (m)

wherein i denotes 0, 1, 2, 3 or 4, preferably 0, 1, 2, or 3, particularly preferred 1 or 2, g1, g2, g3 independently from each other denote 2, 3 or 4, preferably 2 or 3, particularly preferred 2, p1, p3 independently from each other denote 0, 1, 2, 3 or 4, preferably 0, 1, 2 or 3, particularly preferred 0 or 1, p2 denotes 0 or 1, preferably 0, with the proviso that the linear chain consists of 1 to 15 moieties, preferably 1 to 6, particularly preferred 1 to 3 moieties, selected from the group consisting of —CH$_2$—, —O— and —NH— and with the proviso that the nitrogen atom of formula (m) is not directly linked to another nitrogen atom.

The symbol Y$^1$ denotes a bond, Y$^{1.1}$ or —NR$^{Y1.1}$—, wherein,

R$^{Y1.1}$ denotes L$^3$-H or L$^3$-NR$^{Y1.1.1}$R$^{Y1.1.2}$, preferably L$^3$-H, particularly preferred H, wherein R$^{Y1.1.1}$ is selected from among H, C$_{1-4}$-alkyl-, C$_{1-4}$-alkyl-CO— and C$_{1-4}$-alkyl-SO$_2$—, preferably H, C$_{1-2}$-alkyl-CO— and C$_{1-2}$-alkyl-SO$_2$—, particularly preferred H, CH$_3$-alkyl-CO— and CH$_3$-alkyl-SO$_2$—, R$^{Y1.1.2}$ denotes H or C$_{1-4}$-alkyl-, preferably H or —CH$_3$, particularly preferred H, or R$^{Y1.1.1}$ and R$^{Y1.1.2}$ together with the nitrogen atom they are attached to form an optionally substituted 4-7-membered heterocycle containing at least one N-atom, preferably pyrrolidine, piperidine, piperazine, 4-methylpiperazine, 4-acetylpiperazine and morpholine.

The symbol Y$^2$ denotes a bond or is selected from a group consisting of

Y$^{2.1}$, —CO—, —NR$^{Y2.1}$—CO—, —CO—NR$^{Y2.1}$—, Y$^{2.1}$—CONR$^{Y2.1}$—, —Y$^{2.1}$—CO— and —NR$^{Y2.1}$—CO—Y$^{2.1}$—, preferably bond or Y$^{2.1}$, —NR$^{Y2.1}$—CO—, —CO—NR$^{Y2.1}$, and —Y$^{2.1}$—CO—, particularly preferred bond or —NR$^{Y2.1}$—CO— and —CO—NR$^{Y2.1}$, with the proviso that carbonyl moieties are not directly attached to nitrogen atoms of aromatic heterocycles, wherein R$^{Y2.1}$ denotes L$^3$-H or L$^3$-NR$^{Y2.1.1}$R$^{Y2.1.2}$, preferably L$^3$-H, R$^{Y2.1.1}$ is selected from among H, C$_{1-4}$-alkyl-, C$_{1-4}$-alkyl-CO— and C$_{1-4}$-alkyl-SO$_2$—, preferably H, C$_{1-2}$-alkyl-, C$_{1-2}$-alkyl-CO— and C$_{1-2}$-alkyl-SO$_2$—, particularly preferred H, CH$_3$-alkyl-CO— and CH$_3$-alkyl-SO$_2$—, R$^{Y2.1.2}$ denotes H or C$_{1-4}$-alkyl-, preferably H or CH$_3$-alkyl-, particularly preferred H, or R$^{Y2.1.1}$ and R$^{Y2.1.2}$ together with the nitrogen atom they are attached to form an optionally substituted 4-7-membered heterocycle containing at least one N-atom, preferably selected from the group consisting of pyrrolidine, piperidine, piperazine, 4-methylpiperazine, 4-acetylpiperazine and morpholine, $Y^{1.1}, Y^{2.1}$ independently from each other denote a linker in the form of a phenylene group optionally substituted by $-L^5R^{10}$, preferably a linker in the form of an unsubstituted phenylene, or an optionally substituted heteroaromatic or heterocyclic moiety each containing at least one nitrogen atom, preferably $Y^{1.2}, Y^{2.1}$ independently from each other are selected from a group consisting of a linker of formula (a) to (k)

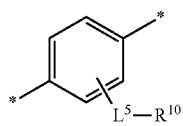

(a)

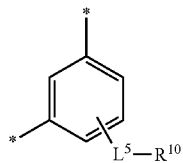

(b)

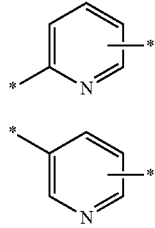

(c)

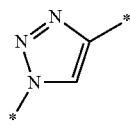

(d)

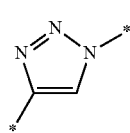

(e)

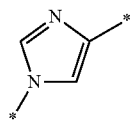

(f)

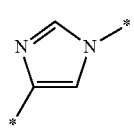

(g)

(h)

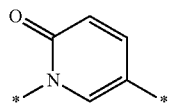

(i)

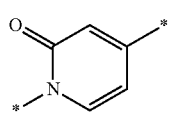

(j)

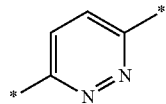

(k)

particularly preferred selected from a group consisting of a linker of formula (a), (e), (f) or (k).

Any and each other of the substituents defined above may be combined with each other.

6. PREPARATION

The following methods are suitable for preparing compounds of general formula (I), The compounds according to the invention may be obtained using methods of synthesis which are known to the one skilled in the art and described in the literature of organic synthesis. General methods for functional groups protection and deprotection steps are described e.g. in: Greene, T. W. and Wuts, P. G. M. (eds.): *Protective Groups in Organic Synthesis*, third edition 1999; John Wiley and Sons, inc. Preferably the compounds are obtained analogously to the methods of preparation explained more fully hereinafter, in particular as described in the experimental section.

Compounds of general formula (I) can be prepared by reacting S-methylisothioureas of formula (II) with primary amines of formula (III) in a solvent like THF, acetonitrile or DMF or in a solvent mixture, preferably in the presence of a base, especially when the primary amine (III) is applied is as an acid addition salt, preferably at r.t. (room temperature).

Scheme 1

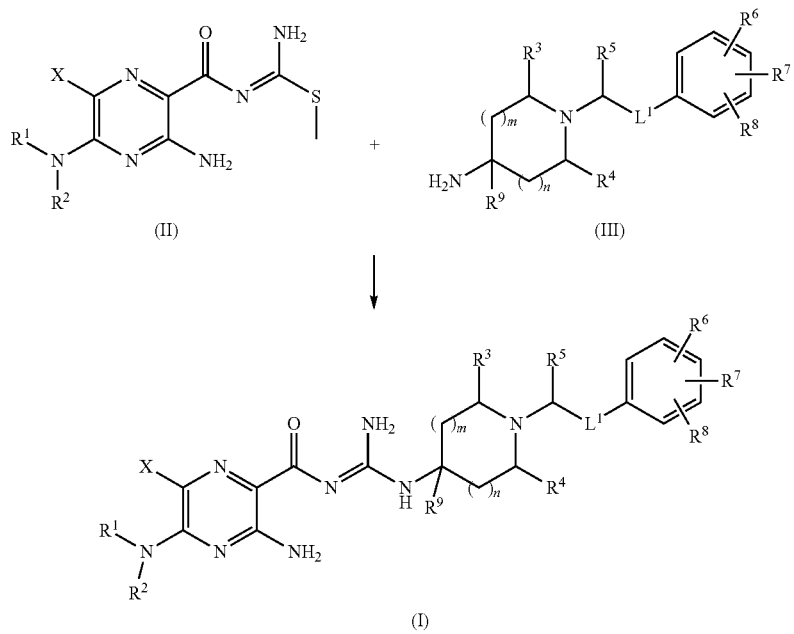

Compounds of general formula (II) can be prepared by reacting S-methylisothiourea (which may be generated in situ from its sulphuric acid salt by addition of base) with a 1-(tert-butylcarbamoyl)prop1-en-2-yl carboxylate of general formula (IV) in a solvent like DCM, THF, water or a mixture of these solvents, preferably at r.t. Compounds of general formula (IV) can be prepared from the respective carboxylic acid of general formula (V) and a 2-tert-butyl-5-methyl-isoxazolium salt of general formula (VI), which can be applied as an isolated salt (e.g. the hexafluorophosphate salt; $X=PF_6$) or generated in situ from tert-butanol, 5-methylisoxazole and trifluoromethanesulphonic acid. The latter reaction is preferably performed in a solvent like DMF or in a solvent mixture with the addition of triethylamine or another base, preferably while cooling to 0-10° C.

Scheme 2

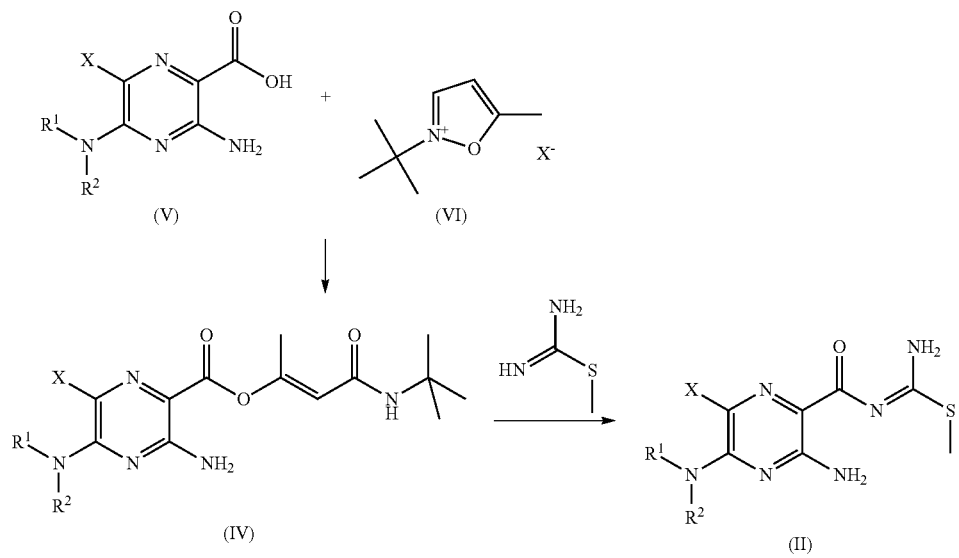

Compounds of general formula (III) can be prepared from compounds of general formula (VII) by removal of the respective protecting group, preferably the BOC or FMOC protecting group which can be removed by standard acidic or basic conditions, respectively. Compounds of general formula (VII) can be modified using methods of synthesis which are known to the one skilled in the art and described in the literature of organic synthesis, preferably by functional group protection or deprotection steps, esterifications, amidations, hydrogenations, or 1,3-dipolar cycloadditions of an azide to a terminal alkyne group or vice versa. Compounds of general formula (VII) can be prepared from secondary amines of general formula (VIII), preferably either by alkylation with a compound of general formula (IX) (wherein the leaving group LG is preferably Cl, Br, OMesyl, or OTosyl), or by reductive amination with an aldehyde of general formula (X) (wherein $R^5$=H).

using methods of synthesis which are known to the one skilled in the art and described in the literature of organic synthesis, preferably by functional group protection or deprotection steps, esterifications, amidations, hydrogenations, or 1,3-dipolar cycloadditions of an azide to a terminal alkyne group or vice versa. After such modification steps, the BOC protecting group in compounds of general formula (XI) can

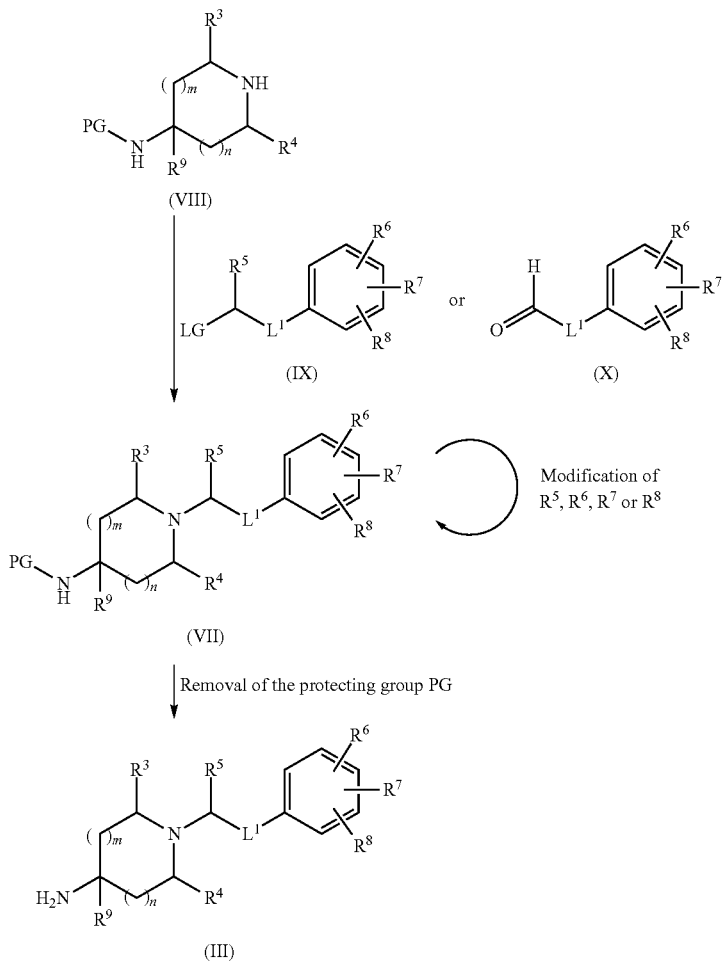

Compounds of general formula (I) can be converted into intermediates of general formula (XI) by BOC-protection. Compounds of general formulas (I) or (XI) can be modified be removed again by standard acidic deprotection conditions to yield modified compounds of general formula (I).

Scheme 4

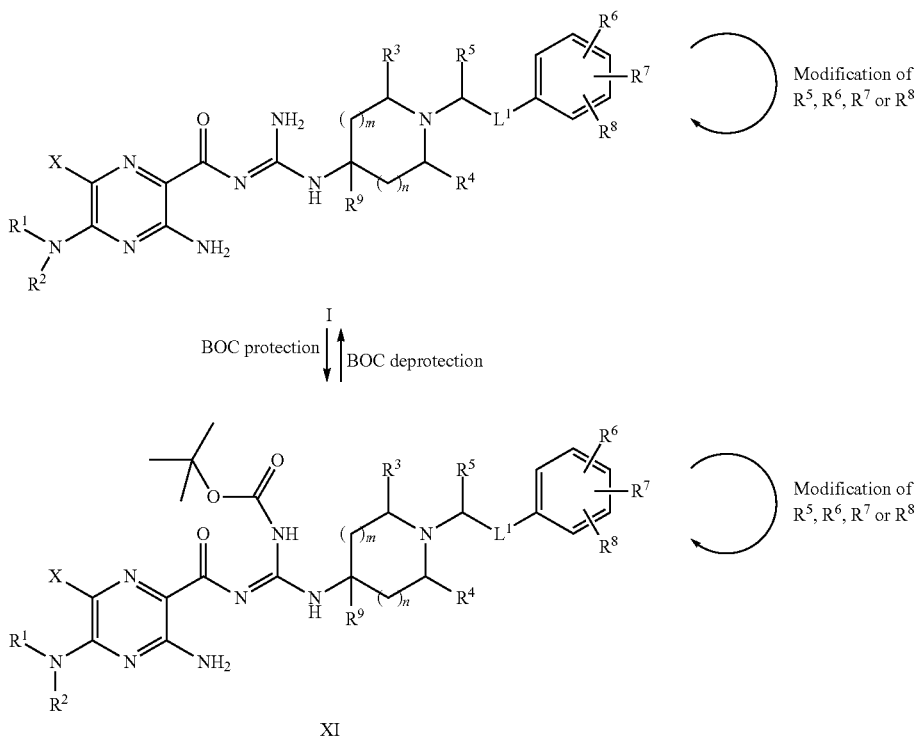

7. EXAMPLES

Where no salt forms of compounds are specified, the compound may exist as a free base or a salt, depending on the synthesis conditions and the processes of workup and purification applied. The skilled person will appreciate that the compound is not limited to the free base or a certain salt form. Where salt forms of compounds are specified, the stoichiometry of the counterion is usually omitted. The skilled person will appreciate that the compound is not limited to the mono salt form and that it may exist as a disalt, trisalt or other compound:counterion stoichiometries. Furthermore, the skilled person will appreciate that such compound may unexpectedly exist as a free base or as a salt with a different counterion, depending on the synthesis conditions and the processes of workup and purification applied. Solely for the purpose of yield is determination, an estimate of the nature of the counterion and of compound:counterion stoichieometry is made (as indicated by the formula given).

7.1 Synthesis of Intermediates

Intermediate I.1

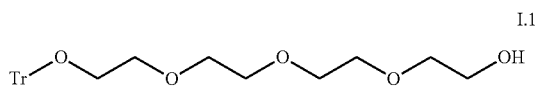

To a solution of tetra(ethylene glycol) (90 g; 463 mmol) in pyridine (100 ml) is added dropwise a solution of triphenylmethyl chloride (30.0 g; 108 mmol) in pyridine (100 ml). The mixture is stirred overnight and evaporated. Water is added and the aqueous layer is decanted, which is repeated for further two times. The residue is dissolved in diethyl ether, extracted with water and then with brine and evaporated. The residue is purified by silica gel column chromatography (gradient: DCM/methanol) 100:0→94:6 to yield the title compound.

Yield: 28.6 g (61% of theory) $C_{27}H_{32}O_5$

ESI Mass spectrum: m/z=454 $[M+NH_4]^+$; m/z=435 $[M-H]^-$

The following compounds are prepared analogously from the starting materials indicated:

TABLE 1

| Intermediate | Structure | Diol starting material |
|---|---|---|
| I.2 | Tr-O-CH2CH2-O-CH2CH2-O-CH2CH2-O-CH2CH2-O-CH2CH2-O-CH2CH2-OH | hexa (ethylene glycol) |
| I.3 | Tr-O-CH2CH2-O-CH2CH2-O-CH2CH2-OH | tri (ethylene glycol) |
| I.4 | Tr-O-CH2CH2-O-CH2CH2-OH | di (ethylene glycol) |

Intermediate II.1

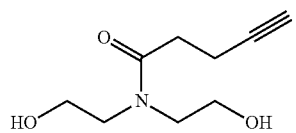

II.1

A mixture of 4-pentynoic acid (2.00 g; 20.4 mmol) and 4-methylmorpholine (2.24 ml; 20.4 mmol) in DCM (20 ml) is cooled to −5° C. Isobutyl chloroformate (2.68 ml; 20.4 mmol) is added, followed by DMF (10 ml). The resulting mixture is added in portions to a solution of diethanolamine (2.25 g; 21.4 mmol) in DCM (10 ml). The resulting mixture is stirred overnight and evaporated. The residue is purified by silica gel column chromatography (gradient: DCM/methanol 100:0→82:18 to yield N,N-bis(2-hydroxyethyl)pent-4-ynamide.

Yield: 2.99 g (79% of theory) $C_9H_{15}NO_3$

ESI Mass spectrum: m/z=186 [M+H]$^+$

Intermediate III.1

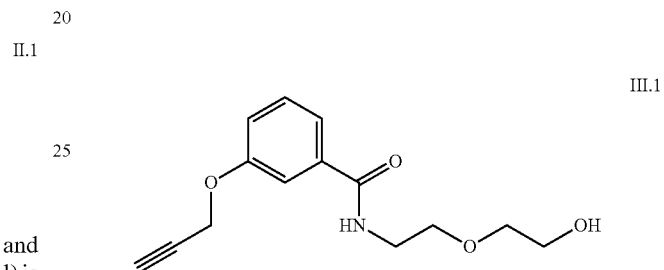

III.1

A mixture of the acid 3-propargyloxy-benzoic acid (0.245 g; 3.35 mmol), triethylamine (0.47 ml; 3.35 mmol) and TBTU (1.08 g; 3.35 ml) in DMF (3 ml) is stirred at ambient temperature for 5 min. The amine 2-(2-hydroxyethoxy)-ethylamine (0.500 g; 4.76 mmol) and further triethylamine (0.47 ml; 3.35 mmol) is added. The mixture is stirred at ambient temperature for 6 h. Ice-water and sodium carbonate solution are added, and the mixture is extracted with ethyl acetate. The organic layer is separated, dried with magnesium sulphate, filtered and evaporated to yield the title compound.

Yield: 0.33 g (37% of theory) $C_{14}H_{17}NO_4$
ESI Mass spectrum: m/z=264 [M+H]$^+$; m/z=262 [M−H]$^-$; m/z=308 [M+HCOO]$^-$ The following compounds are prepared accordingly from the starting materials as indicated:

TABLE 2

| Intermediate | Structure | Acid/amine starting materials | Synthesis comment |
|---|---|---|---|
| III.2 | (structure shown) | N-BOC-beta-alanine/N-methyl-propargylamine | |

TABLE 2-continued

| Intermediate | Structure | Acid/amine starting materials | Synthesis comment |
|---|---|---|---|
| III.3 | 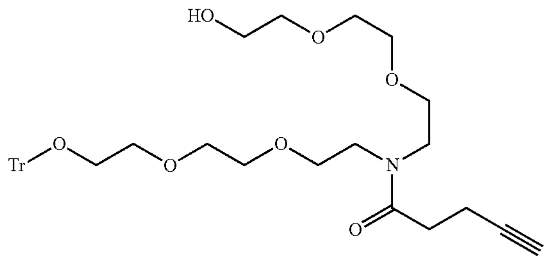 | 4-pentynoic acid/IV.2 | The crude product is further purified by silsica gel column chromatography (gradient: DCM/methanol 100:0 → 90:10). |
| III.4 | 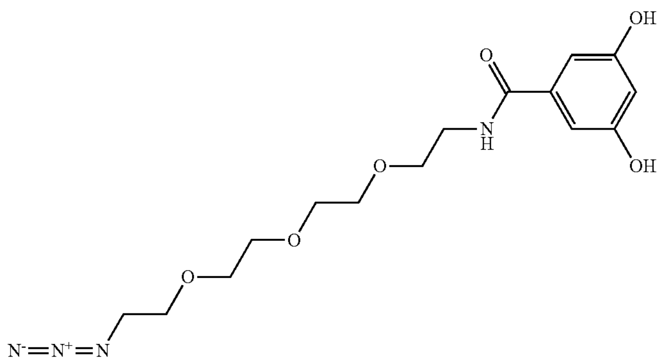 [SMILES: [N-]=[N+]=NCCOCCOCCOCCNC(=O)c1cc(O)cc(O)c1] | 3,5-dihydroxy-benzoic acid/ 1-amino-11-azido-3,6,9-trioxaundecane | The crude product is purified by RP-HPLC (modifier: TFA). |

Intermediate IV.1

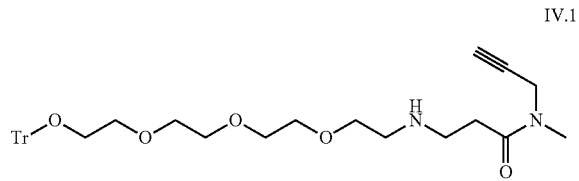

IV.1

To a solution of the alcohol intermediate 1.1 (3.49 g; 8.00 mmol) and triethylamine (1.64 g; 16.0 mmol) in DCM (20 ml) is added slowly methanesulphonyl chloride (0.929 ml; 12.0 mmol). The mixture is stirred at ambient temperature for 1 h and then extracted with water. The organic layer is evaporated and the residue is taken up in acetonitrile (20 ml). The amine 3-amino-N-methyl-N-(prop-2-yn-1-yl)propanamide hydrochloride (2.54 g; 10.1 mmol; prepared from Intermediate III.2 by BOC-deprotection with HCl in dioxane (4 mol/l)) and triethylamine (2.45 g; 24.0 mmol) are added and the mixture is stirred at 60° C. overnight. Water is added and the resulting mixture is extracted with extracted with DCM. The organic layer is dried with magnesium sulphate, filtered and evaporated. The residue is purified by silica gel column chromatography (gradient: DCM/methanol 100:0→86:14 to yield the title compound.

Yield: 1.11 g (25% of theory) $C_{34}H_{42}N_2O_5$

ESI Mass spectrum: m/z=559 $[M+H]^+$; m/z=603 $[M+HCOO]^-$

HPLC analytics: RT=1.38 min (HPLC method 4)

The following compounds are prepared analogously from the starting materials indicated:

TABLE 3

| Intermediate | Structure | Alcohol/amine starting materials |
|---|---|---|
| IV.2 | 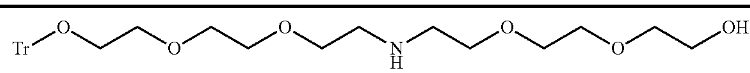 | I.3/2-[2-(2-amino-ethoxy)-ethoxy]-ethanol |
| IV.3 | 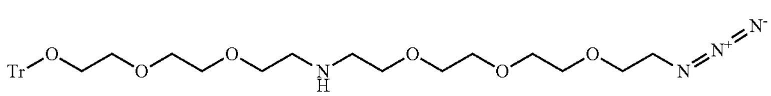 | I.3/1-[2-(2-amino-ethoxy)-ethoxy]-2-(2-azidoethoxy)-ethane |

Intermediate V.1

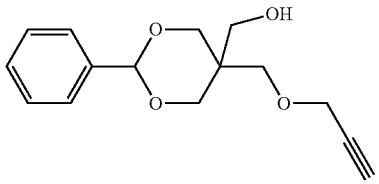

A mixture of 5,5-bis(hydroxymethyl)-2-phenyl-1,3-dioxane (500 mg; 2.23 mmol), propargyl bromide (80% in toluene; 224 µl; 2.01 mmol) and NaH (60% in mineral oil; 85 mg; 2.22 mmol) in THF is stirred overnight at 50° C. Water is added and the organic solvent is evaporated. Further water is added under stirring. The precipitate formed is filtered off and purified by silica gel column chromatography (gradient: DCM/methanol 100:0→90:10 to yield the title compound as a mixture of E/Z isomers.

Yield: 190 mg (32% of theory) $C_{15}H_{18}O_4$
ESI Mass spectrum: m/z=263 [M+H]$^+$

Intermediate VI.1

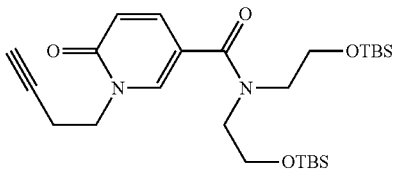

A mixture of 6-hydroxynicotinic acid (300 mg; 2.16 mmol) and CDI (420 mg; 2.59 mmol) in THF is stirred at ambient temperature for 30 min. O,O'-Bis(TBDMS)-diethanolamine (720 mg; 2.16 mmol) is added and the mixture is stirred overnight at ambient temperature. Volatiles are evaporated and the residue is purified by silica gel column chromatography (gradient: DCM/methanol 100:0→90:10 to yield the respective amide intermediate (750 mg; 76% of theory) which is further reacted as follows:

A mixture of the amide intermediate (710 mg; 1.56 mmol), 4-bromo-1-butyne (228 mg; 1.72 mmol) and cesium carbonate (712 mg; 2.19 mmol) in acetonitrile (10 ml) is stirred overnight at 70° C. Further 4-bromo-1-butyne (500 µl; 5.33 mmol) and cesium carbonate (712 mg; 2.19 mmol) are added and the mixture is stirred for one more day at 70° C. Volatiles are evaporated, water is added and the mixture is extracted with DCM. The organic layer is separated and evaporated. The residue is purified by silica gel column chromatography (gradient: DCM/methanol 100:0→70:30 to yield the title compound.

Yield: 315 mg (40% of theory) $C_{26}H_{46}N_2O_4Si_2$
ESI Mass spectrum: m/z=507 [M+H]$^+$; m/z=551 [M+HCOO]$^-$

Intermediate VII.1

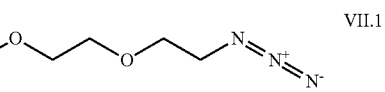

A mixture of the alcohol I.2 (5.00 g; 9.53 mmol), methanesulphonyl chloride (1.11 ml; 14.3 mmol) and triethylamine (3.35 ml; 23.8 mmol) in DCM (50 ml) is stirred at ambient temperature for 1 h. Sodium azide (1.86 g; 28.6 mmol) is added and the mixture is stirred overnight, then for 2 h at 50° C. Further DCM is added and the mixture is extracted with sodium carbonate solution. The organic layer is separated, dried with magnesium sulphate, filtered and evaporated. The residue is purified by silica gel column chromatography (gradient: DCM/methanol 100:0→70:30 to yield the title compound.

Yield: 4.39 g (84% of theory) $C_{31}H_{39}N_3O_6$
ESI Mass spectrum: m/z=567 [M+H]$^+$; m/z=594 [M+HCOO]$^-$ The following compounds are prepared analogously from the starting materials indicated:

TABLE 4

| Intermediate | Structure | Alcohol starting material |
|---|---|---|
| VII.2 | Tr-O-CH2CH2-O-CH2CH2-O-CH2CH2-N=N+=N- | I.3 |
| VII.3 | Tr-O-CH2CH2-O-CH2CH2-N=N+=N- | I.4 |

Intermediate VIII.1

VIII.1

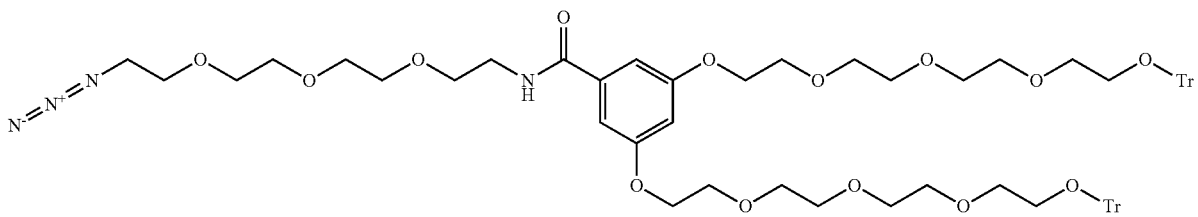

Methanesulphonyl chloride (426 µl; 5.50 mmol) is added carefully to a mixture of the trityl ether I.1 (2.18 g; 5.00 mmol) and triethylamine (1.85 ml; 13.2 mmol) in DCM (20 ml). The mixture is stirred for 2 h, then extracted with water. The organic layer is separated and evaporated. Acetonitrile (20 ml), the diphenol intermediate III.4 (780 mg; 2.20 mmol) and potassium carbonate (913 mg; 6.60 mmol) are added, and the mixture is refluxed overnight. Water is added and the mixture is extracted with DCM. The organic layer is separated, dried with magnesium sulphate, filtered and evaporated. The residue is purified by silica gel column chromatography (gradient: DCM/(methanol:aqueous ammonia 9:1) 100:0→85:15 to yield the title compound.

Yield: 2.28 g (63% of theory) $C_{69}H_{82}N_4O_{14}$

ESI Mass spectrum: m/z=1191 $[M+H]^+$; m/z=594 $[M+HCOO]^-$

The following compounds are prepared analogously from the starting materials indicated:

Yield: 910 mg (60% of theory) $C_{33}H_{44}N_4O_6$
ESI Mass spectrum: m/z=593 $[M+H]^+$ Intermediate X.1

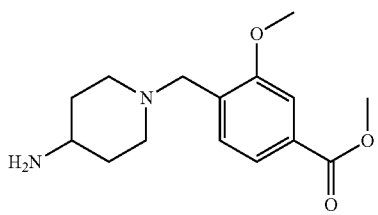

X.1

TABLE 5

| Intermediate | Structure | Trityl ether starting |
|---|---|---|
| VIII.2 | 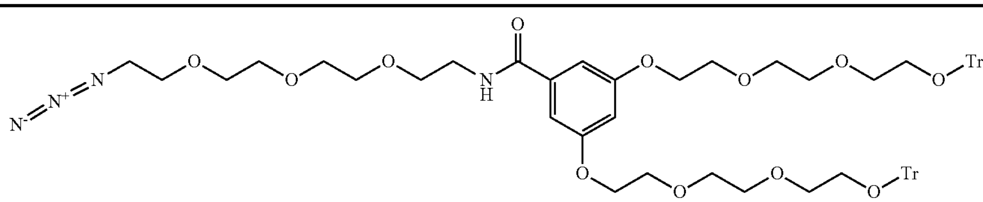 | I.3 |

Intermediate IX.1

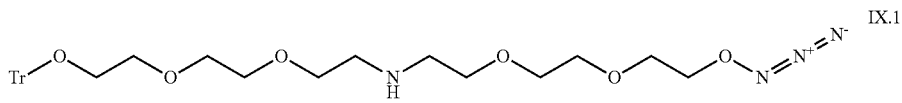

IX.1

Methanesulphonyl chloride (276 µl; 3.57 mmol) is added carefully to a mixture of the trityl ether intermediate I.3 (1.00 g; 2.55 mmol) and triethylamine (715 µl; 5.60 mmol) in DCM (10 ml). The mixture is stirred overnight, then extracted with water. The organic layer is separated and evaporated. Acetonitrile (10 ml), triethylamine (715 µl; 5.60 mmol) and 1-amino-11-azido-3,6,9-trioxaundecane (850 mg; 3.90 mmol) is added and the mixture is refluxed for 4 h. The mixture is evaporated and the residue is purified by silica gel column chromatography (gradient: DCM/(methanol:aqueous ammonia 9:1) 100:0→90:10 to yield the title compound.

Stage 1: A mixture of the halide methyl-4-(bromomethyl)-3-methoxy-benzoate (0.50 g; 1.93 is mmol), the amine tert-butyl N-(piperidin-4-yl)carbamate (0.386 g; 1.93 mmol) and triethylamine (0.538 ml; 3.86 mmol) in THF (10 ml) is stirred for 4 h. The solvent is evaporated. The residue is taken up in water and sodium carbonate solution and extracted with DCM. The organic layer is dried with magnesium sulphate, filtered and evaporated. The residue is purified by silica gel column chromatography (gradient: DCM/Methanol 100:0→92:8 to yield Methyl 4-[(4-{[(tertbutoxy)carbonyl]amino}piperidin-1-ylmethyl]-3-methoxybenzoate.

Yield: 650 mg (89% of theory) $C_{20}H_{30}N_2O_5$
ESI Mass spectrum: m/z=379 $[M+H]^+$; m/z=423 $[M+HCOO]^-$ Stage 2 (removal of BOC protecting group): A mixture of Methyl 4-[(4-{[(tertbutoxy)carbonyl]amino}piperidin-1-yl-methyl]-3-methoxybenzoate and HCl in dioxane (4 mol/l; 1.82 ml; 7.27 mmol) in methanol (10 ml) is stirred overnight. Volatiles are evaporated and the resulting solid is suspended in ethyl acetate, filtered and evaporated again to yield Methyl (4-aminopiperidin-1-yl)methyl-3-methoxybenzoate as a hydrochloride salt.

Yield: 480 mg (105% of theory calculated for the dihydrochloride salt)

$C_{15}H_{22}N_2O_3 \times 2HCl$

The following compounds are prepared accordingly from starting materials as indicated. Unless stated otherwise, the amine component applied is tert-butyl N-(piperidin-4-yl)carbamate. Depending on conditions applied, the syntheses may yield a free base, a hydrochloride or dihydrochloride salt, a zwitterion or other salt forms which can be applied equally to the syntheses of example compounds as described above.

TABLE 6

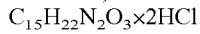

| Intermediate | Structure | Halide starting material | Synthesis comment |
|---|---|---|---|
| X.2 | 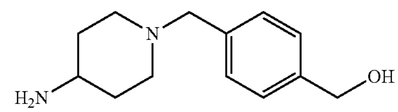 [SMILES: NC1CCN(Cc2ccc(CO)cc2)CC1] | 4-Hydroxymethyl-benzylchloride | |
| X.3 | 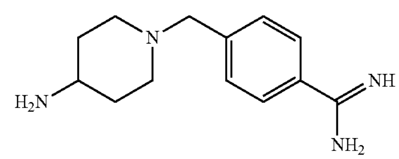 [SMILES: N=C(N)c1ccc(CN2CCC(N)CC2)cc1] | 4-bromomethyl-benzamide hydrochloride *[a] | *[b], without prior extraction. |
| X.4 | 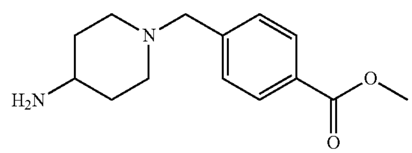 [SMILES: COC(=O)c1ccc(CN2CCC(N)CC2)cc1] | Methyl-4-(bromomethyl)-benzoate | |
| X.5 | 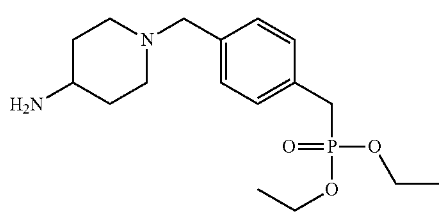 [SMILES: CCOP(=O)(Cc1ccc(CN2CCC(N)CC2)cc1)OCC] | (4-Bromomethyl-benzyl)-phosphoric acid diethyl ester | |
| X.6 | 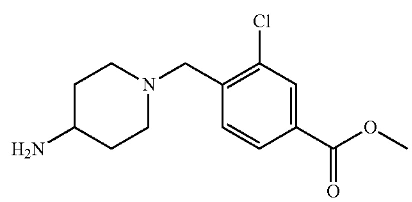 [SMILES: COC(=O)c1ccc(CN2CCC(N)CC2)c(Cl)c1] | Methyl 3-chloro-4-bromomethyl-benzoate | |
| X.7 | 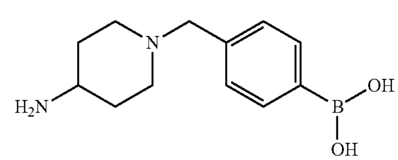 [SMILES: NC1CCN(Cc2ccc(B(O)O)cc2)CC1] | 4-Bromomethyl-phenylboronic acid | |
| X.8 | 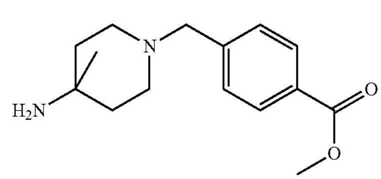 | Methyl 4-bromomethyl-benzoate | Amine applied: tert-butyl N-(4-methyl-piperidin-4-yl)carbamate |

TABLE 6-continued

| Intermediate | Structure | Halide starting material | Synthesis comment |
|---|---|---|---|
| X.9 | 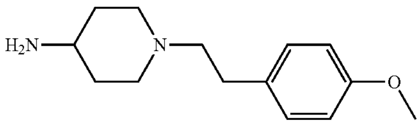 [SMILES: COc1ccc(CCN2CCC(N)CC2)cc1] | 1-(2-bromoethyl)-4-methoxybenzene | |
| X.10 | 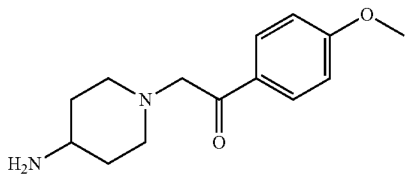 [SMILES: COc1ccc(C(=O)CN2CCC(N)CC2)cc1] | 4-Methoxyphenacyl bromide | |
| X.11 | 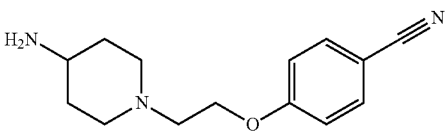 [SMILES: N#Cc1ccc(OCCN2CCC(N)CC2)cc1] | 4-(2-Bromoethoxy)-benzonitrile | |
| X.12 | 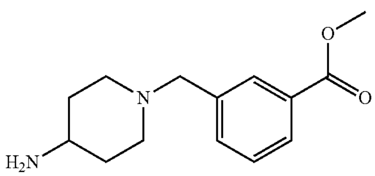 [SMILES: COC(=O)c1cccc(CN2CCC(N)CC2)c1] | Methyl 3-(bromoethyl)-benzoate | The product is purified by RP-HPLC (modifier: ammonia). |
| X.13 | 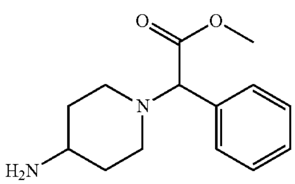 [SMILES: COC(=O)C(c1ccccc1)N1CCC(N)CC1] | Methyl alpha-bromophenyl-acetate | |
| X.14 | 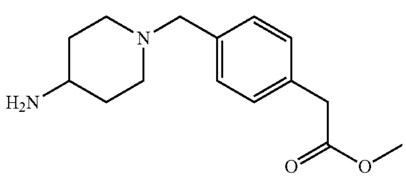 [SMILES: COC(=O)Cc1ccc(CN2CCC(N)CC2)cc1] | Methyl (4-bromomethyl-phenyl)-acetate | |
| X.15 | 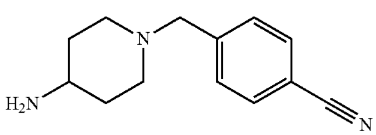 [SMILES: N#Cc1ccc(CN2CCC(N)CC2)cc1] | 4-Bromomethyl-benzonitrile | |
| X.16 | 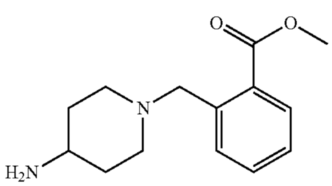 [SMILES: COC(=O)c1ccccc1CN1CCC(N)CC1] | Methyl 2-(bromomethyl)-benzoate | |
| X.17 | 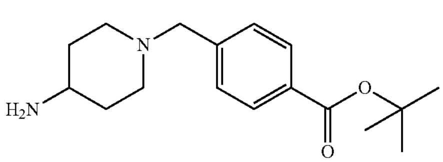 [SMILES: CC(C)(C)OC(=O)c1ccc(CN2CCC(N)CC2)cc1] | tert-Butyl 4-(bromomethyl)-benzoate | Product purified by silica gel chromatography (DCM/MeOH/aq. ammonia). |
| X.18 | 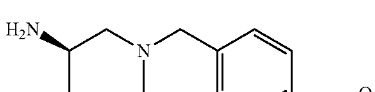 | tert-Butyl 4-(bromomethyl)-benzoate | Amine applied: (R)-3-N-BOC-aminopiperidine; removal of BOC protecting |

Intermediate XI.1

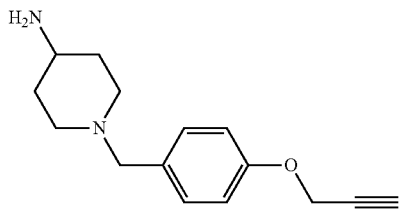

XI.1

Stage 1: Methanesulphonyl chloride (0.929 ml; 12 mmol) is added to an ice-cold mixture of the alcohol (4-prop-2-ynyloxy-phenyl)-methanol (1.62 g; 10 mmol) and triethylamine (2.81 ml; 20 mmol) in DCM (20 ml). After stirring overnight, the amine tert-butyl N-(piperidin-4-yl)carbamate (4.01 g; 20 mmol) is added. After further stirring overnight, water is added. The organic phase is separated, dried with magnesium sulphate, filtered and evaporated. The residue is purified by silica gel column chromatography (DCM/Methanol 9:1) to yield tert-Butyl N-(1-{[4-(prop-2-yn-1-yloxy)phenyl]methyl}piperidin-4-yl)carbamate.

Yield: 1.07 g (31% of theory) $C_{20}H_{28}N_2O_3$

ESI Mass spectrum: m/z=345 [M+H]$^+$

Stage 2: The BOC protecting group is removed as described for compound X.1 to yield 1-{[4-(prop-2-yn-1-yloxy)phenyl]methyl}piperidin-4-amine as a hydrochloride salt.

$C_{15}H_{20}N_2O \times 2HCl$

ESI Mass spectrum: m/z=245 [M+H]$^+$

The following compounds are prepared accordingly from starting materials as indicated. Unless stated otherwise, the amine component applied is tert-butyl N-(piperidin-4-yl)carbamate. Due to conditions applied, the syntheses may yield a free base, a hydrochloride or dihydrochloride salt, a zwitterion or other salt forms which can be applied equally to the syntheses of example compounds as described above.

TABLE 7

| Intermediate | Structure | Alcohol starting materials | Synthesis comment |
|---|---|---|---|
| XI.2 | 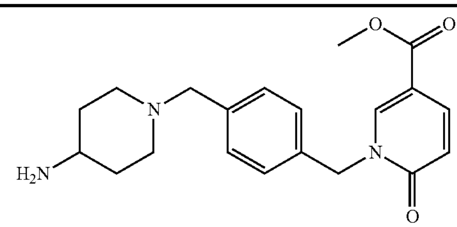 | XXII.1 | The crude product is further purified by RP HPLC (modifier: TFA) to yield the title compound as a TFA salt. |
| XI.3 | 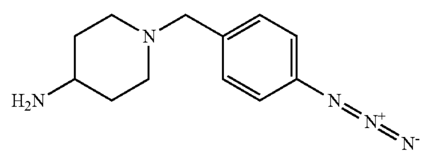 [SMILES: [N-]=[N+]=Nc1ccc(CN2CCC(N)CC2)cc1] | (4-azidophenyl)-methanol | |
| XI.4 | 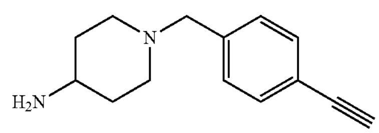 [SMILES: C#Cc1ccc(CN2CCC(N)CC2)cc1] | (4-Ethynyl-phenyl)-methanol | |
| XI.5 | 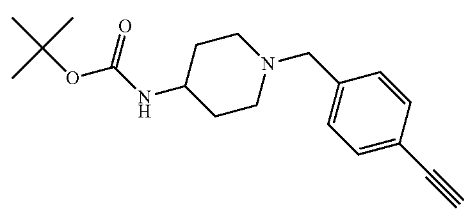 [SMILES: C#Cc1ccc(CN2CCC(NC(=O)OC(C)(C)C)CC2)cc1] | See entry for XI.4 | The BOC removal step (stage 2) is not applied. |
| XI.6 | 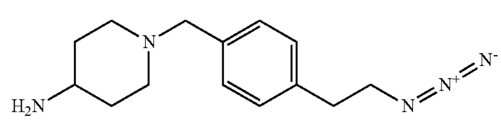 [SMILES: [N-]=[N+]=NCCc1ccc(CN2CCC(N)CC2)cc1] | [4-(2-azido-ethyl)-phenyl]-methanol | Alcohol prepared from [4-(2-chloro-ethyl)-phenyl]-methanol and sodium azide in DMF/ 100° C./5 h. |

Intermediate XII.1

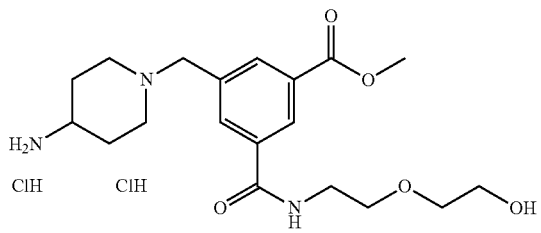

Stage 1: A mixture of the aldehyde methyl 3-formyl-5-{[2-(2-hydroxyethoxy)ethyl]-carbamoyl}-benzoate (4.51 g; 12.2 mmol) (which is prepared beforehand by amidation of Methyl 3-formyl-5-hydroxycarbonyl-benzoate with 2-(2-Hydroxyethoxy)-ethylamine using HATU as coupling reagent) and tert-butyl N-(piperidin-4-yl)carbamate (3.67 g; 18.3 mmol) in THF (50 ml) is refluxed for 3 h. Glacial acetic acid (approx. 2 ml) is added to adjust at pH5. Sodium triacetoxyborohydride (5.18 g; 24.4 mmol) is added and the mixture is refluxed for further 2 h. Ethyl acetate and water are added, the organic layer is separated, dried with Magnesium Sulphate, filtered and evaporated. The residue is purified first by silica gel column chromatography (gradient DCM/methanol 100:0→88:12), then by RP HPLC (modifier: ammonia) to yield Methyl 3-[(4-{[(tertbutoxy)carbonyl]amino}piperidin-1-yl)methyl]-5-{[2-(2-hydroxyethoxy)ethyl]carbamoyl}benzoate Yield: 915 mg (16% of theory) $C_{24}H_{37}N_3O_7$ ESI Mass spectrum: m/z=480 $[M+H]^+$ Stage 2: The BOC protecting group is removed as described for compound X.1 to yield Methyl 3-[(4-aminopiperidin-1-yl)methyl]-5-{[2-(2-hydroxyethoxy)ethyl]carbamoyl}benzoate as a Hydrochloride $C_{19}H_{29}N_3O_5 \times 2HCl$ ESI Mass spectrum: m/z=380 $[M+H]^+$; m/z=378 $[M-H]^-$ The following compounds are prepared accordingly from starting materials as indicated. Unless stated otherwise, the amine component applied is tert-butyl N-(piperidin-4-yl)carbamate. Due to conditions applied, the syntheses may yield a free base, a hydrochloride or dihydrochloride salt, a zwitterion or other salt forms which can be applied equally to the syntheses of example compounds as described above.

TABLE 8

| Intermediate | Structure | Aldehyde starting material applied | Synthesis comment |
|---|---|---|---|
| XII.2 | 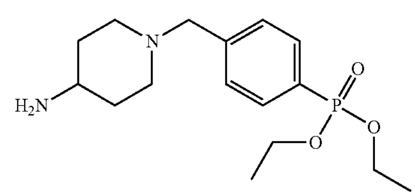 [SMILES: CCOP(=O)(OCC)c1ccc(CN2CCC(N)CC2)cc1] | Diethyl (4-formylphenyl)-phosphonate | |
| XII.3 | 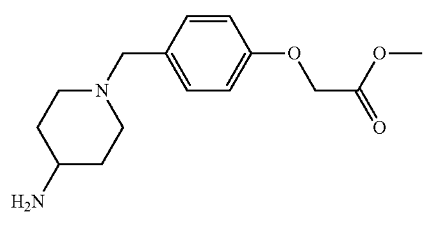 [SMILES: COC(=O)COc1ccc(CN2CCC(N)CC2)cc1] | Methyl (4-formyl-phenoxy)-acetate | |
| XII.4 | 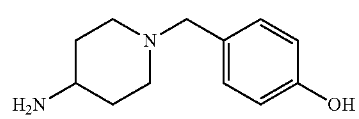 [SMILES: NC1CCN(Cc2ccc(O)cc2)CC1] | 4-Hydroxy-benzaldehyde | |
| XII.5 | 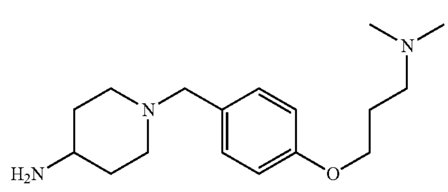 [SMILES: CN(C)CCCOc1ccc(CN2CCC(N)CC2)cc1] | 4-[3-(dimethylamino)-propoxy]-benzaldehyde | |

TABLE 8-continued

| Intermediate | Structure | Aldehyde starting material applied | Synthesis comment |
|---|---|---|---|
| XII.6 | 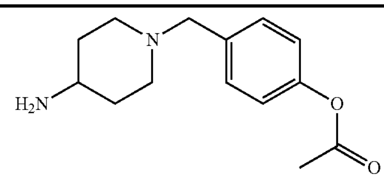 | 4-Formylphenyl acetate | |
| XII.7 | 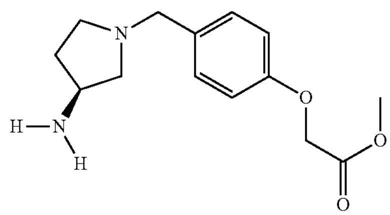 [SMILES: COC(=O)COc1ccc(CN2CC[C@H](N)C2)cc1] | Methyl 2-(4-formylphenoxy)-acetate | Amine applied: (3S)-3-tert-butoxycarbonyl-amino-pyrrolidine |
| XII.8 | 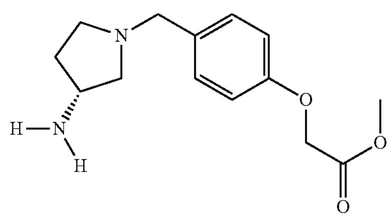 [SMILES: COC(=O)COc1ccc(CN2CC[C@@H](N)C2)cc1] | Methyl 2-(4-formylphenoxy)-acetate | Amine applied: (3R)-3-tert-butoxycarbonyl-amino-pyrrolidine |
| XII.9 | 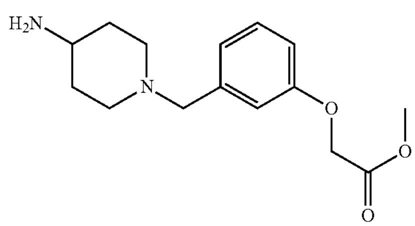 [SMILES: COC(=O)COc1cccc(CN2CCC(N)CC2)c1] | Methyl 2-(3-formylphenoxy)-acetate | |
| XII.10 | 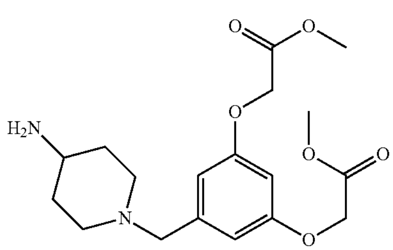 [SMILES: COC(=O)COc1cc(CN2CCC(N)CC2)cc(OCC(=O)OC)c1] | 3,5-Bis(methoxy)-carbonylmethoxy)-benzaldehyde | |
| XII.11 | 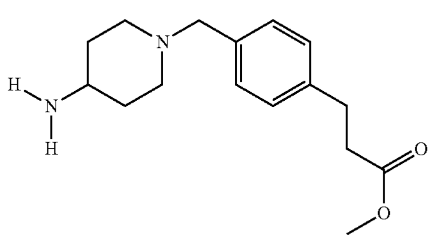 [SMILES: COC(=O)CCc1ccc(CN2CCC(N)CC2)cc1] | Methyl 3-(4-formylphenyl)-propanoate | |
| XII.12 | 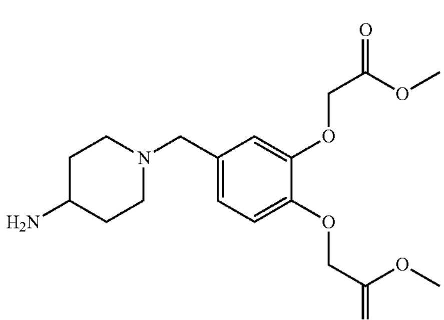 | 3,4-Bis(methoxy)-carbonylmethoxy)-benzaldehyde | |

Intermediate XIII.1

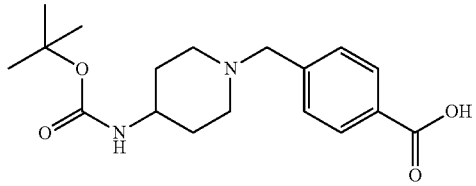

XIII.1

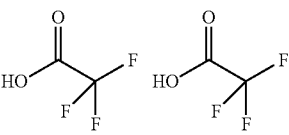

A mixture of 4-[(4-{[(tert-butoxy)carbonyl] amino}piperidin-1-yl)methyl]benzoic acid (BOC protected intermediate from the synthesis of X.4 [without application of stage 2]; 3.80 g; 10.5 mmol) and aqueous NaOH solution (4 mol/l; 4.0 ml) in ethanol (20 ml) is stirred overnight at 50° C. Volatiles are evaporated and aqueous hydrochloric acid (4 mol/l; 4.0 ml) is added. The mixture is extracted three times with ethyl acetate. The combined organic layers are dried with sodium sulphate, filtered and evaporated to yield 4-[(4-{[(tert-butoxy)carbonyl]amino}piperidin-1-yl)methyl]benzoic acid.

Yield: 1.80 g (51% of theory) $C_{18}H_{26}N_2O_4$

ESI Mass spectrum: m/z=335 [M+H]$^+$; m/z=333 [M−H]$^−$

Intermediate XIV.1

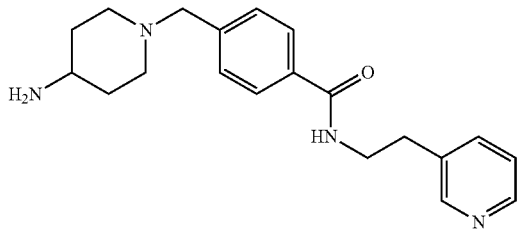

XIV.1

Stage 1: A mixture of 4-[(4-{[(tert-butoxy)carbonyl] amino}piperidin-1-yl)methyl]benzoic acid (Intermediate XIII.1; 3.00 g; 8.97 mmol), TBTU (3.20 mg; 9.97 mmol) and triethylamine (1.40 ml; 10.0 mmol) in DMF (50 ml) is stirred for 5 min. The amine 3-(2-aminoethyl)-pyridine (1.06 ml; 9.00 mmol) is added. After further 3 h stirring, the solvent is evaporated and the residue is taken up in DCM and washed with sodium carbonate solution. The organic layer is dried over sodium sulphate, filtered and evaporated. The residue is purified by silica gel column chromatography (gradient DCM/Methanol) to yield tert-Butyl N-[1-({4-[(2-(3-pyridyl)-ethylamino)carbonyl]phenyl}methyl)piperidin-4-yl] carbamate Yield: 3.36 g (85% of theory)

$C_{25}H_{34}N_4O_3$

ESI Mass spectrum: m/z=439 [M+H]$^+$

Stage 2: The BOC protecting group is removed as described for intermediate X.1 to yield N-[1-({4-[(2-(3-pyridyl)-ethylamino)carbonyl]phenyl}methyl)piperidin-4-yl] amine. The crude product is further purified by RP HPLC (modifier: TFA) to yield the title compound as a TFA salt.

Yield: 3.91 g (90% of theory)

$C_{20}H_{26}N_4O \times 2TFA$

ESI Mass spectrum: m/z=339 [M+H]$^+$

The following compounds are prepared accordingly from starting materials as indicated. Depending on conditions applied, the syntheses may yield a free base, a TFA salt or bis-TFA salt, a zwitterion or other salt forms which can be applied equally to the syntheses of example compounds as described above.

TABLE 9

| Intermediate | Structure | Amine starting material | Synthesis comment |
|---|---|---|---|
| XIV.2 | 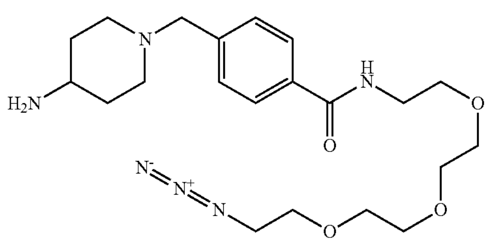 [SMILES: [N-]=[N+]=NCCOCCOCCOCCNC(=O)c1ccc(CN2CCC(N)CC2)cc1] | 1-[2-(2-aminoethoxy)-ethoxy]-2-(2-azido-ethoxy)-ethane | |
| XIV.3 | 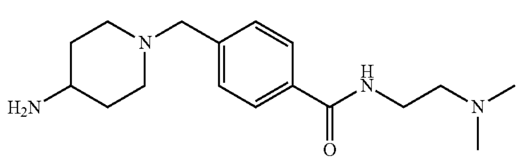 [SMILES: CN(C)CCNC(=O)c1ccc(CN2CCC(N)CC2)cc1] | 2-dimethylamino-ethylamine | |

TABLE 9-continued

| Intermediate | Structure | Amine starting material | Synthesis comment |
| --- | --- | --- | --- |
| XIV.4 | 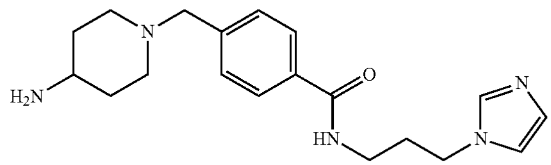 [SMILES: NC1CCN(Cc2ccc(C(=O)NCCCn3ccnc3)cc2)CC1] | 1-(3-aminopropyl)-imidazole | |
| XIV.5 | 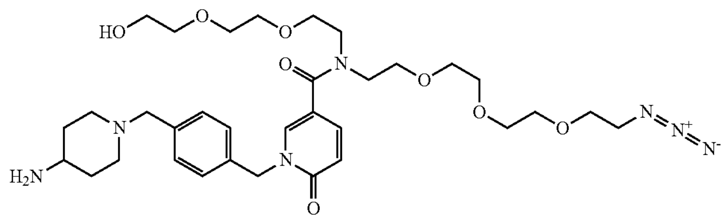 [SMILES: [N-]=[N+]=NCCOCCOCCOCCN(CCOCCOCCO)C(=O)c1ccc(=O)n(Cc2ccc(CN3CCC(N)CC3)cc2)c1] | IV.3 | *c |
| XIV.6 | 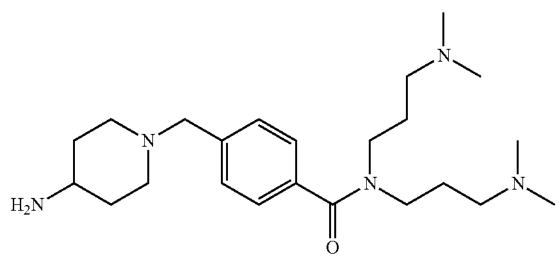 [SMILES: CN(C)CCCN(CCCN(C)C)C(=O)c1ccc(CN2CCC(N)CC2)cc1] | 3,3'-bis(dimethyl-amino)-dipropylamine | |
| XIV.7 | 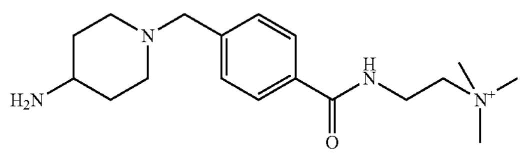 [SMILES: C[N+](C)(C)CCNC(=O)c1ccc(CN2CCC(N)CC2)cc1] | (2-aminoethyl)-trimethyl-ammonium chloride hydrochloride | *d |
| XIV.8 | 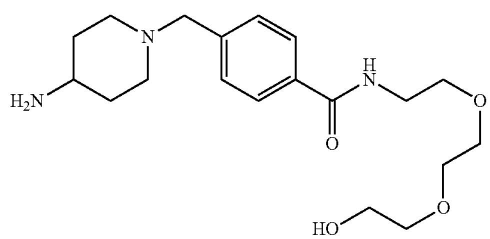 [SMILES: NC1CCN(Cc2ccc(C(=O)NCCOCCOCCO)cc2)CC1] | 2-[2-(2-amino-ethoxy)-ethoxy]-ethanol | |
| XIV.9 | 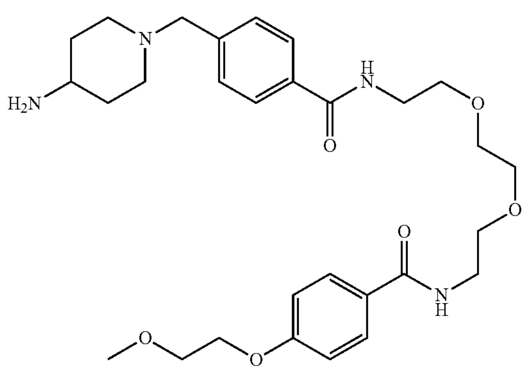 [SMILES: COCCOc1ccc(C(=O)NCCOCCOCCNC(=O)c2ccc(CN3CCC(N)CC3)cc2)cc1] | N-{2-[2-(2-amino-ethoxy)ethoxy]ethyl}-4-(2-methoxyethoxy)-benzamide *a | |
| XIV.10 | 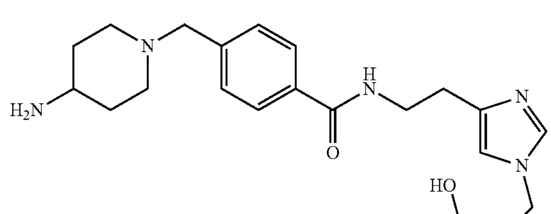 | 3-[4-(2-aminoethyl)-1H-imidazol-1-yl]propan-1-ol *b | *e |

Intermediate XV.1

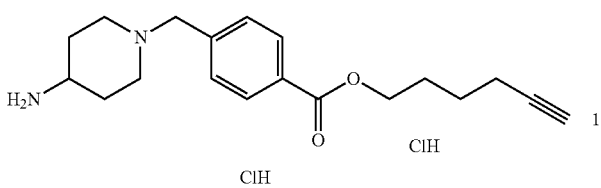

XV.1

Stage 1: To a solution of 4-(chloromethyl)benzoyl chloride (2.00 g; 10.6 mmol) in THF (30 ml) are added 5-hexyn-1-ol (1.18 ml; 10.6 mmol) and DMAP (0.1 g; 0.82 mmol). The mixture is refluxed overnight with stirring. BOC-4-aminopiperidine (2.33 g; 11.6 mmol) and triethylamine (3.24 ml; 23.3 mmol) are added and the mixture is refluxed for further 3 h. Ethyl acetate (200 ml) and water (50 ml) are added. The organic layer is separated, washed with water and with brine and evaporated to dryness. The residue is purified by silica gel column chromatography (gradient cyclohexane/ethyl acetate 8:2→2:8) to yield 5-Hexyn-1-yl 4-[(4-{[(tertbutoxy)carbonyl]amino}piperidin-1-yl)methyl]-benzoate.

Yield: 3.11 g (71% of theory) $C_{24}H_{34}N_2O_4$
ESI Mass spectrum: m/z=415 $[M+H]^+$ Stage 2: The BOC protecting group is removed as described for intermediate X.1 to yield Hex-5-yn-1-yl 4-[(4-aminopiperidin-1-yl)methyl]benzoate as a hydrochloride salt.

$C_{18}H_{28}N_3O_4P\times 2HCl$
ESI Mass spectrum: m/z=315 $[M+H]^+$

Intermediate XVI.1

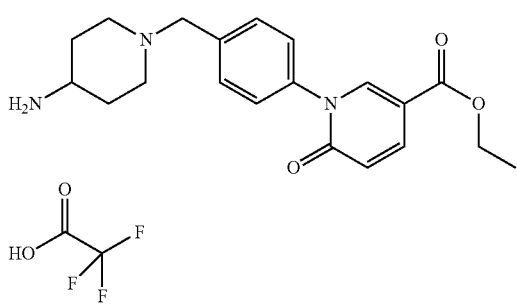

XVI.1

Stage 1: A mixture of {4-[(4-{[(tert-butoxy)carbonyl]amino}piperidin-1-yl)methyl]phenyl}boronic acid (800 mg; 2.39 mmol; prepared as described for the synthesis of intermediate X.7 without BOC deprotection step), ethyl 6-hydroxypyridine-3-carboxylate (420 mg; 2.51 mmol), copper (II) acetate (250 mg; 1.38 mmol) and pyridine (210 μl; 2.60 mmol) in DCM (10 ml) is stirred overnight. The mixture is filtered and extracted with water. The organic layer is dried with sodium sulphate, filtered and evaporated. The residue is purified by silica gel column chromatography (gradient DCM/methanol 98:2→94:4) to yield ethyl 1-{4-[(4-{[(tert-butoxy)carbonyl]amino}piperidin-1-yl)methyl]phenyl}-6-oxo-1,6-dihydropyridine-3-carboxylate Yield: 580 mg (53% of theory) $C_{25}H_{33}N_3O_5$
ESI Mass spectrum: m/z=456 $[M+H]^+$ Stage 2: The BOC protecting group is removed by stirring in TFA/DCM (1:5) at r.t. to yield ethyl 1-{4-[(4-aminopiperidin-1-yl)methyl]phenyl}-6-oxo-1,6-dihydropyridine-3-carboxylate.

$C_{20}H_{25}N_3O_3P\times TFA$
ESI Mass spectrum: m/z=356 $[M+H]^+$

Intermediate XVII.1

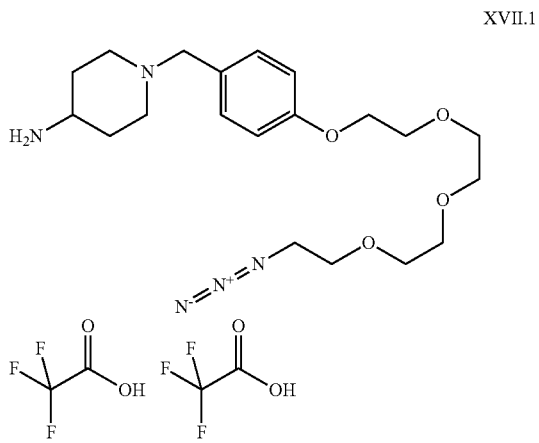

XVII.1

Stage 1: To a mixture of 1-azido-3,6,9-trioxaundecane-11-ol (220 mg; 0.98 mmol) and triethylamine (550 μl; 3.92 mmol) in DCM (5 ml) is added methanesulphonyl chloride (250 μl; 3.23 mmol). After stirring for 2 h water is added. The organic layer is separated at evaporated. Acetonitrile (5 ml), tert-butyl N-{1-[(4-hydroxyphenyl)methyl]piperidin-4-yl}carbamate (300 mg; 0.98 mmol; prepared as described for the synthesis of intermediate XII.4 without BOC deprotection step) and potassium carbonate (410 mg; 2.97 mmol) are added and the resulting mixture is refluxed overnight. The mixture is evaporated to dryness, taken up in water and extracted with DCM. The organic layer is dried with magnesium sulphate, filtered and evaporated. The residue is purified by silica gel column chromatography (gradient DCM/methanol 98:2→94:4) to yield tert-butyl N-(1-{[4-(2-{2-[2-(2-azidoethoxy)ethoxy]ethoxy}ethoxy)phenyl]methyl}piperidin-4-yl)carbamate.

Yield: 84 mg (17% of theory) $C_{25}H_{41}N_5O_6$
ESI Mass spectrum: m/z=508 $[M+H]^+$ Stage 2: The BOC protecting group is removed as described for XVI.1 (stage 2) to yield 1-{[4-(5,8,11-trioxa-1,2-diazamidec-1-en-13-yloxy)phenyl]methyl}piperidin-4-amine as a TFA salt.

$C_{20}H_{33}N_5O_4\times 2$ TFA
ESI Mass spectrum: m/z=408 $[M+H]^+$

Intermediate XVIII.1

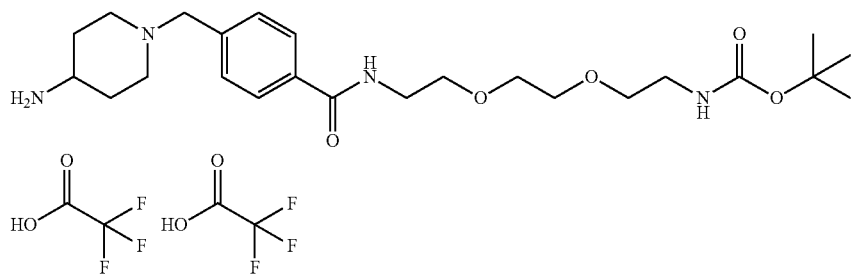

XVIII.1

Stage 1: A mixture of 4-[(4-{[(9H-fluoren-9-ylmethoxy)carbonyl]amino}piperidin-1-yl)methyl]benzoic acid (1.20 g; 2.63 mmol), TBTU (1.01 g; 3.15 mmol) and DIPEA (1.8 ml; 3.15 mmol) in DMF (10 ml) is stirred for 5 min. tert-Butyl N-{2-[2-(2-aminoethoxy)ethoxy]ethyl}carbamate (783 mg; 3.15 mmol) is added and the mixture is stirred overnight. Volatiles are evaporated and the product is purified by RP-HPLC (modifier: TFA) to yield 9H-fluoren-9-ylmethyl N-(1-{[4-({2-[2-(2-{[(tertbutoxy)carbonyl]amino}ethoxy)ethoxy]ethyl}carbamoyl)phenyl]methyl}piperidin-4-yl)carbamate.

Yield: 240 mg (13% of theory) $C_{39}H_{50}N_4O_7$

ESI Mass spectrum: m/z=687 [M+H]$^+$

Stage 2: A mixture of 9H-fluoren-9-ylmethyl N-(1-{[4-({2-[2-(2-{[(tertbutoxy)carbonyl]amino}ethoxy)ethoxy]ethyl}carbamoyl)phenyl]methyl}piperidin-4-yl)carbamate (240 mg; 0.314 mol) and piperidine (0.31 ml; 3.1 mmol) in THF (10 ml) is stirred overnight. Volatiles are evaporated and the product is purified by RP-HPLC (modifier: TFA) to yield tert-butyl N-(2-{2-[2-({4-[(4-aminopiperidin-1-yl)methyl]phenyl}formamido)ethoxy]ethoxy}ethyl)carbamate as a TFA salt.

Yield: 100 mg (37% of theory) $C_{24}H_{40}N_4O_5 \times 2$ TFA

ESI Mass spectrum: m/z=465 [M+H]$^+$

Intermediate XIX.1

A mixture of the aryl halide component tert-butyl N-{1-[(4-iodophenyl)methyl]piperidin-4-yl}carbamate (5.00 g; 12.0 mmol; prepared analogously to the procedure described for the synthesis of intermediate X.1 without BOC-deprotection.), the alkyne component 3-ethynylpyridine (2.48 g; 24.0 mmol), tris(dibenzylideneaceton)dipalladium(0) (0.55 mg; 0.60 mmol) and copper(I)iodide (229 mg; 1.20 mmol) in triethylamine (100 ml) is stirred under argon atmosphere at 70° C. for 3d. Volatiles are evaporated and the residue is taken up in DCM. The resulting mixture is filtered through celite and extracted with water. The organic layer is dried with magnesium sulphate and evaporated. The crude product is purified by silica gel column chromatography (gradient DCM/methanol 100:0→95:5) to yield the BOC-protected alkyne intermediate (3.50 g; 8.98 mmol) which is hydrogenated with Raney-Nickel (0.70 g) in methanol (40 ml) under hydrogen pressure (50 psi). The catalyst is filtered off with suction and the resulting solution is evaporated to dryness to yield the title compound.

Yield: 3.52 g (93% of theory) $C_{24}H_{33}N_3O_2$

ESI Mass spectrum: m/z=396 [M+H]$^+$

The following compounds are prepared analogously from the starting materials indicated.

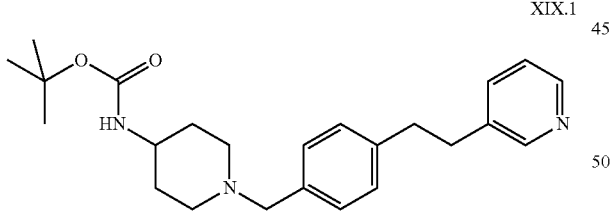

XIX.1

TABLE 10

| Intermediate | Structure | Aryl halide starting material | Alkyne starting material | Synthesis comment |
|---|---|---|---|---|
| XIX.2 | 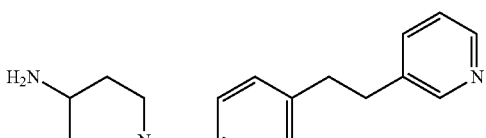 | 3-iodo-6-(2-methoxyethoxy)pyridazine *a | XI.5 | [1,1'-Bis-(diphenylphosphino)-ferrocene]-dichloropalladium (II) applied as catalyst |

*a 3-iodo-6-(2-methoxyethoxy)pyridazine is prepared from 3,6-diiodopyridazine and 2-methoxyethanol with sodium hydride in THF.

Intermediates XX.1 and XX.2

The following intermediates are prepared through BOC-deprotection analogously to the procedure described in the synthesis of intermediate X.1 from the starting material indicated. Due to conditions applied, the syntheses may yield a free base, a hydrochloride or dihydrochloride salt or other salt forms which can be applied equally to the syntheses of example compounds as described above.

TABLE 11

| Intermediate | Structure | Starting materials applied |
|---|---|---|
| XX.1 | 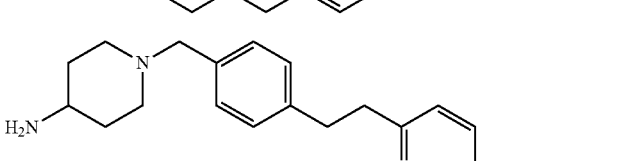 | XIX.1 |
| XX.2 | 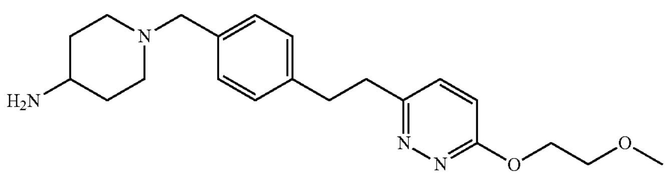 [SMILES: COCCOc1ccc(CCc2ccc(CN3CCC(N)CC3)cc2)nn1] | XIX.2 |

Intermediate XXI.1

XXI.1

$N^- = N^+ = N$ —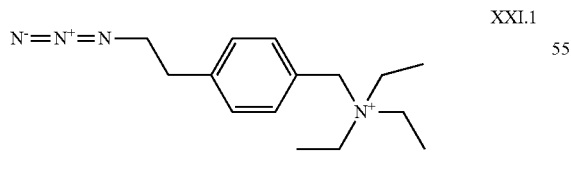

To a mixture of [4-(2-azidoethyl)phenyl]methanol (2.66 g; 15.0 mmol) and triethylamine (6.5 ml; 46 mmol) in toluene (50 ml) is added dropwise POCl₃ (0.67 ml; 7.34 mmol). The mixture is stirred for 5 d at r.t. Water (10 ml) is added and the mixture is stirred for further 2 h. Volatiles are evaporated. The residue is taken up in DCM and extracted with water. The aqueous layer is separated and evaporated. The residue is purified by silica gel column chromatography (gradient: DCM/(Methanol/aq. Ammonia 9:1) 92:8→77:23 to yield the title compound (the counterion may be hydroxide but is not characterized).

Yield: 1.20 g (31% of theory) $C_{15}H_{25}N_4^+ \times HO^-$

ESI Mass spectrum: m/z=261 [M]⁺; 351 [M+2HCOO]⁻

Intermediate XXII.1

XXII.1

A mixture of 6-hydroxynicotinic acid methyl ester (8.00 g; 52.2 mmol), 4-(chloromethyl)-phenylmethanol (9.00 g; 57.5 mmol) and cesium carbonate (34 g) in ACN (200 ml) is stirred overnight at r.t. and then filtered. The filtrate is evaporated and the residue is taken up in water and extracted three times with ethyl acetate. The combined organic layers are dried with magnesium sulphate, filtered and evaporated. The residue is purified by silica gel column chromatography (gradient: DCM/methanol 100:0→90:10 to yield the title compound.

Yield: 4.79 g (34% of theory) $C_{15}H_{15}NO_4$
ESI Mass spectrum: m/z=274 [M+H]$^+$ Intermediate XXIII.1

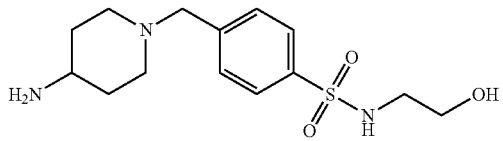

XXIII.1

To a mixture of 4-(bromomethyl)-benzenesulphonyl chloride (1.00 g; 3.71 mmol) and triethylamine (2.08 ml; 14.8 mmol) in DCM (20 ml) is added slowly the amino reagent ethanolamine (0.224 ml; 3.71 mmol). The mixture is stirred for 1 hour at r.t., then tert-butyl N-(piperidin-4-yl)carbamate (892 mg; 4.45 mmol) is added. The mixture is stirred for 3 days at r.t., then water is added. The organic layer is separated and evaporated. The residue is purified by silica gel column chromatography (gradient: DCM/(methanol/aq. ammonia 9:1) 100:0→90:10 to yield the BOC protected intermediate which is deprotected as described for the synthesis of intermediate XVI.1.

Yield: 240 mg (12% of theory, assuming a bis-TFA-salt is generated)
$C_{14}H_{23}N_3O_3S \times 2\ C_2HF_3O_2$
ESI Mass spectrum: m/z=314 [M+H]$^+$; m/z=312 [M−H]$^-$ The following compounds are prepared analogously replacing ethanolamine by the amino reagent indicated:

A mixture of 3-(chloromethyl)benzoic acid (1.00 g; 5.86 mmol), tert-butyl N-(piperidin-4-yl)carbamate (1.17 g; 5.86 mmol), triethylamine (0.832 ml; 5.86 mmol) and ACN (10 ml) is stirred over night at 70° C. The mixture is cooled to r.t., then 2-(2-aminoethoxy)ethanol (1.75 ml; 17.6 mmol) and TBTU (1.98 g; 6.16 mmol) are added. The mixture is stirred for 3 days, then water is added and the mixture is extracted with ethyl acetate. The organic layer is dried with magnesium sulphate, filtered and evaporated. The residue is purified by silica gel column chromatography (gradient: DCM/(Methanol/aq. Ammonia 9:1) 100:0→90:10 to yield the title compound.

Yield: 1.13 g (46% of theory) $C_{22}H_{35}N_3O_5$
ESI Mass spectrum: m/z=422 [M+H]$^+$; m/z=420 [M−H]$^-$; m/z=466 [M+HCOO]$^-$ Intermediate XXV.1

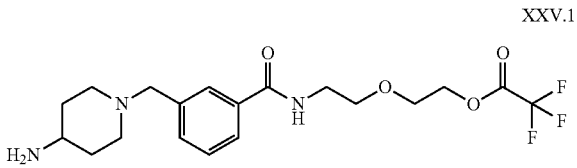

XXV.1

Intermediate XXIV.1 (0.90 g; 2.14 mmol) is stirred in TFA/DCM (3:10; 13 ml) at r.t. for 2 hours. The mixture is evaporated to yield the title compound.

Yield: 2.18 g (103% of theory, assuming a bis-TFA-salt is generated)
$C_{13}H_{26}F_3N_3O_4 \times 2\ C_2HF_3O_2$

TABLE 12

| Intermediate | Structure | Amino reagent applied |
|---|---|---|
| XXIII.2 | 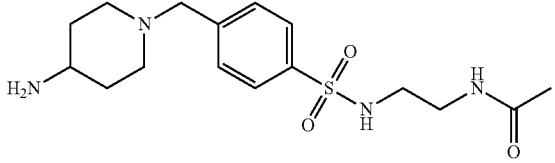 [SMILES: CC(=O)NCCNS(=O)(=O)c1ccc(CN2CCC(N)CC2)cc1] | N-acetyl-ethylenediamine |

Intermediate XXIV.1

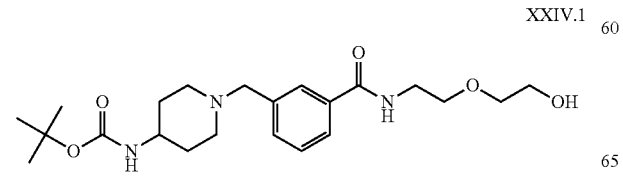

XXIV.1

ESI Mass spectrum: m/z=418 [M+H]+

Intermediate A.1

3,5-diamino-6-chloropyrazine-2-carboxylic acid

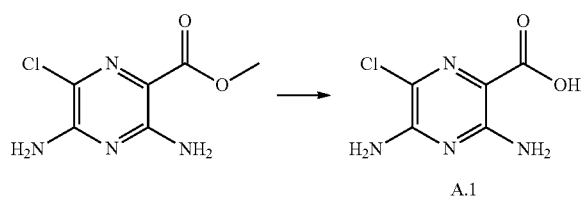

A mixture of methyl 3,5-diamino-6-chloropyrazine-2-carboxylate (100 g; 494 mmol), methanol (1 l) and NaOH (6 mol/l in water; 240 mL; 1.44 mol) is refluxed for 3 h. The mixture is allowed to cool to r.t. and then neutralized by addition of hydrochloric acid (6 mol/l in water; approx. 240 mL). Water (200 mL) is added. The precipitate formed is filtered off with suction, washed with water and dried at 60° C.

Yield: 99.6 g (107% of theory)
$C_5H_5ClN_4O_2$ ESI Mass spectrum: m/z=189 [M+H]+; m/z=187 [M−H]−

Intermediate A.2

3,5-diamino-6-bromopyrazine-2-carboxylic acid is prepared from methyl 3,5-diamino-6-bromopyrazine-2-carboxylate (which is prepared from methyl 3,5-diamino-6-chloropyrazine-2-carboxylate as described in J. Med. Chem. 10 (1967) 66-75) analogously to the procedure described for the synthesis of intermediate A.1

Intermediate B.1

1-(tert-butylcarbamoyl)prop-1-en-2-yl 3,5-diamino-6-chloropyrazine-2-carboxylate

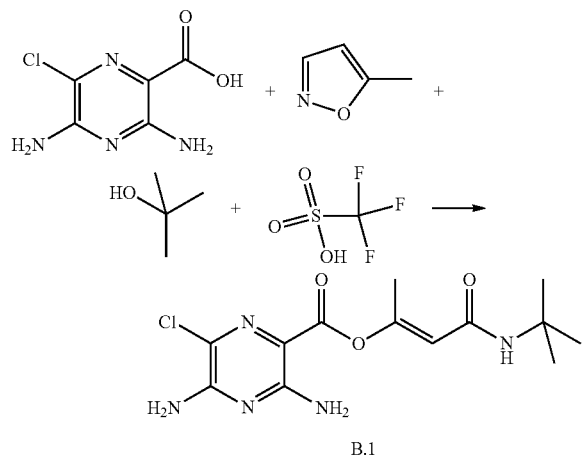

Stage 1:
A mixture of tert-butanol (21.0 mL; 226 mmol) and 5-methylisoxazole (18.0 mL; 221 mmol) is cooled with an ice-bath. Trifluoromethanesulphonic acid (20.0 mL; 221 mmol) is added dropwise with continued cooling. The resulting mixture is stirred for 1 h without further cooling.

Stage 2:
To a solution or suspension of 3,5-diamino-6-chloropyrazine-2-carboxylic acid (Intermediate A.1; 14.0 g; 74.2 mmol) and triethylamine (31.0 mL; 222 mmol) in DMF (100 mL) is added the mixture prepared in stage 1. The resulting mixture is stirred for 4 h at r.t. Ice-water is added with stirring. The precipitate formed is filtered off with suction, washed with water and dried at 65° C. to yield the title compound.

Yield: 18.2 g (75% of theory)
$C_{13}H_{18}ClN_5O_3$ ESI Mass spectrum: m/z=328 [M+H]+; m/z=326 [M−H]−

TLC (Silica; DCM/MeOH 9:1): $R_f$=0.4

Intermediate B.2

1-(2-methyl-2-butyl-carbamoyl)prop-1-en-2-yl 3,5-diamino-6-bromopyrazine-2-carboxylate

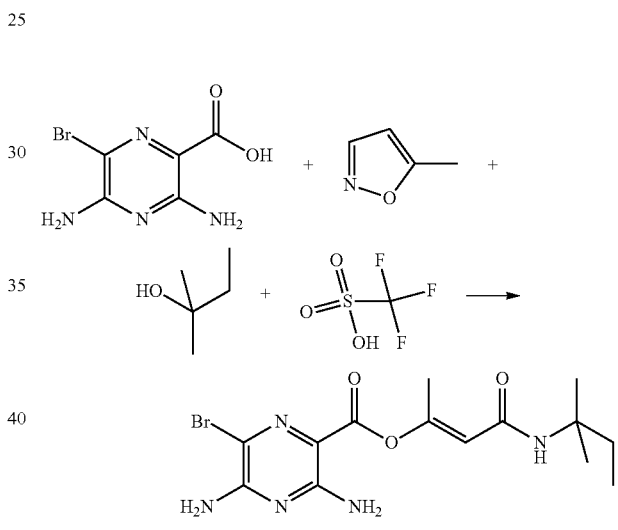

Stage 1:
A mixture of 2-methyl-2-butanol (5.75 mL; 51 mmol) and 5-methylisoxazole (4.42 mL; 51 mmol) is cooled with an ice-bath. Trifluoromethanesulphonic acid (4.84 mL; 54 mmol) is added dropwise with continued cooling. The resulting mixture is stirred over night without further cooling.

Stage 2:
To a solution or suspension of 3,5-diamino-6-bromopyrazine-2-carboxylic acid (Intermediate A.2; 5.00 g; 21.5 mmol) and triethylamine (7.48 mL; 54 mmol) in DMF (50 mL) cooled with an ice-bath is added dropwise the mixture prepared in stage 1. The resulting mixture is stirred for 4 h at r.t., then poured on ice-water. The precipitate formed is filtered off with suction, washed with is water and dried at 50° C. to yield the title compound.

Yield: 7.53 g (91% of theory)

$C_{14}H_{20}BrN_5O_3$ ESI Mass spectrum: m/z=386 [M+H]+; m/z=384 [M−H]−

Intermediate C.1

3,5-diamino-6-chloro-N-[(methylsulfanylmethanimidoyl]pyrazine-2-carboxamide

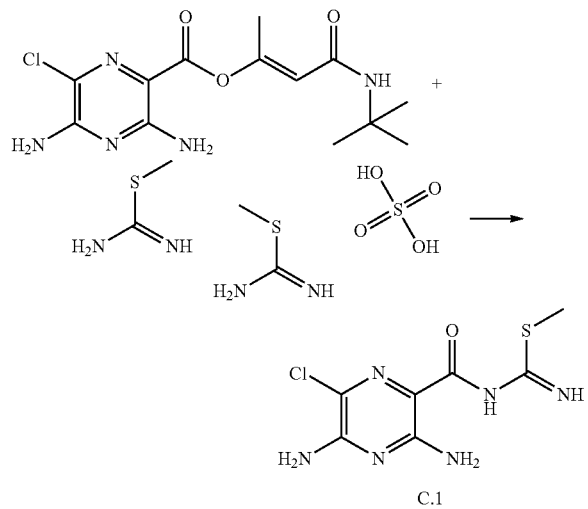

C.1

To NaOH (1 mol/l in water; 9.2 mL; 9.2 mmol) is added S-methylisothiourea sulphate (1.78 g; 6.1 mmol. The mixture is stirred until complete solution is achieved. TBME/THF (1:1; 30 mL) and then 1-(tert-butylcarbamoyl)prop-1-en-2-yl 3,5-diamino-6-chloropyrazine-2-carboxylate (Intermediate B.1; 2.00 g; 6.10 mmol) are added and the mixture is stirred at r.t. over night, then water (6 mL) is added. The precipitate formed is filtered off with suction, washed successively with water, methanol and then with diethyl ether and then dried at 50° C. to yield the title compound.

Yield: 1.33 g (84% of theory)
$C_7H_9ClN_6OS$ ESI Mass spectrum: m/z=261 [M+H]+; m/z=259 [M−H]−

Intermediate C.2

3,5-diamino-6-bromo-N-[(methylsulfanylmethanimidoyl]pyrazine-2-carboxamide

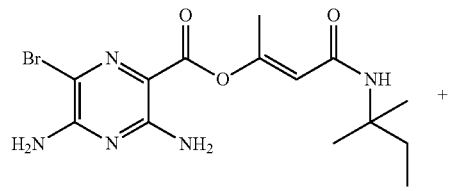

+

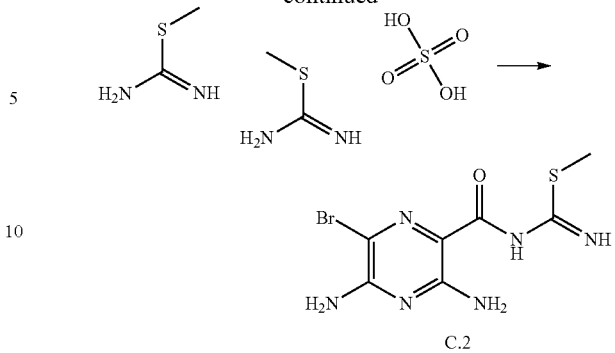

C.2

To NaOH (1 mol/l in water; 30 mL; 30 mmol) is added S-methylisothiourea sulphate (5.42 g; 19.5 mmol. The mixture is stirred until complete solution is achieved. TBME/THF (1:1; 100 mL) and then 1-(2-methyl-2-butyl-carbamoyl)prop-1-en-2-yl 3,5-diamino-6-bromopyrazine-2-carboxylate (Intermediate B.2; 7.52 g; 19.5 mmol) are added and the mixture is stirred at r.t. over night, then water (100 mL) is added. The precipitate formed is filtered off with suction, washed with THF/water (1:2) and then dried at 50° C. to yield the title compound.

Yield: 5.44 g (92% of theory)
$C_7H_9BrN_6OS$ ESI Mass spectrum: m/z=305 [M+H]+

7.2 Synthesis of Examples

Example 1.1

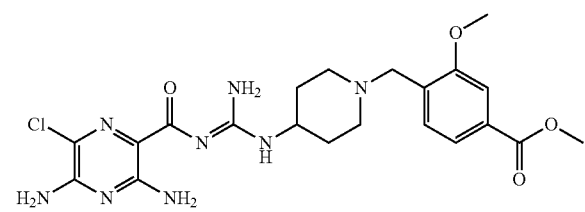

1.1

A mixture of 3,5-diamino-6-chloro-N-[(methylsulfanyl)methanimidoyl]pyrazine-2-carboxamide (Intermediate C.1; 0.35 g; 1.34 mmol), the primary amine X.1 (0.48 g; 1.37 mmol) and triethylamine (0.56 ml; 4.03 mmol) in THF (10 ml) is stirred overnight. Volatiles are evaporated and the residue is purified by silica gel column chromatography (gradient: DCM/(methanol/aq. ammonia 9:1) 100:0→90:10. Product containing fractions are evaporated, suspended in ether, filtered off with suction and dried.

Yield: 293 mg (44% of theory) $C_{21}H_{27}ClN_8O_4$
ESI Mass spectrum: m/z=491 [M+H]+
HPLC analytics: RT=1.26 min (HPLC method 1)
The following compounds of general formula 1.A are prepared accordingly using the respective primary amine as indicated:

TABLE 13

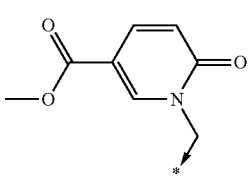

| Example | R⁷ | R⁸ | Primary amine applied: | Synthesis comment | ESI mass spectrum | HPLC Retention time (min) | HPLC method |
|---|---|---|---|---|---|---|---|
| 1.2 | H | —CH₂OH | X.2 | | 433 (M + H)+ | 0.92 | 7 |
| 1.3 | H | —CH₂—CH₂—N₃ | XI.6 | | 472 (M + H)+<br>516 (M + HCOO)— | 1.02 | 7 |
| 1.4 | H | —O—CH₂—CCH | XI.1 | | 457 (M + H)+<br>913 (2M + H)+ | 1 | 7 |
| 1.5 | H | 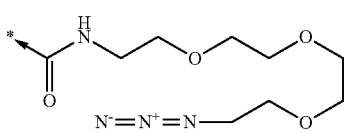 | XI.2 | | 568 (M + H)+<br>566 (M − H)− | 1.28 | 2 |
| 1.7 | H | 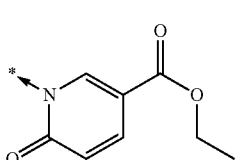 | XIV.2 | | 647 (M + H)+<br>645 (M − H)− | 1.38 | 1 |
| 1.8 | H | —CH₂—P(O)(OEt)₂ | X.5 | | 553 (M + H)+<br>551 (M − H)− | 1.38 | 1 |
| 1.9 | H | —C(O)O—(CH₂)₄—CCH | XV.1 | | 527 (M + H)+<br>525 (M − H)− | 1.01 | 4 |
| 1.10 | H | —N₃ | XI.3 | | 444 (M + H)+<br>442 (M − H)− | 0.82 | 5 |
| 1.12 | Cl | —C(O)OMe | X.6 | | 495 (M + H)+<br>493 (M − H)− | 1.54 | 1 |
| 1.13 | H | —P(O)(OEt)₂ | XII.2 | | 539 (M + H)+<br>583 (M + HCOO)— | 1.29 | 1 |
| 1.14 | H | —C(O)NH—(CH₂)₂—NMe₂ | XIV.3 | | 517 (M + H)+<br>515 (M − H)− | 0.63 | 6 |
| 1.15 | H | —B(OH)₂ | X.7 | | 447 (M + H)+ | 1.05 | 1 |
| 1.16 | H | 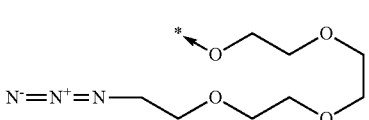 | XVI.1 | | 568 (M + H)+ | 1.25 | 1 |
| 1.18 | H |  | XVII.1 | | 620 (M + H)+ | 0.91 | 6 |
| 1.23 | H | 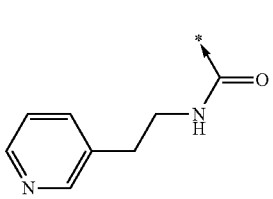 | XIV.4 | | 554 (M + H)+ | 0.67 | 6 |
| 1.24 | H |  | XIV.1 | | 551 (M + H)+ | 0.66 | 6 |

TABLE 13-continued

Structure: Pyrazine carboxamide with Cl, two NH2 groups, connected via guanidine (=N-C(NH2)=N-H) to a piperidine, N-benzyl substituted with R7 (ortho) and R8 (para).

| Example | R⁷ | R⁸ | Primary amine applied: | Synthesis comment | ESI mass spectrum | HPLC Retention time (min) | HPLC method |
|---|---|---|---|---|---|---|---|
| 1.25 | H | —H | *ᵃ | 1-benzyl-piperidin-4-amine | 403 (M + H)+<br>805 (2M + H)+ | 0.97 | 7 |
| 1.29 | H | —C(O)OMe | X.4 | | 461 (M + H)+ | 1.05 | 7 |
| 1.30 | H | —OCH₂—C(O)OMe | XII.3 | | 491 (M + H)+<br>981 (2M + H)+ | 0.81 | 7 |
| 1.31 | H | —OH | XII.4 | | 419 (M + H)+ | 1.39 | 8 |
| 1.33 | H | bis(3-dimethylaminopropyl)amino carbonyl | XIV.6 | | 614 (M − H)− | 0.37 | 8 |
| 1.34 | H | —O(CH₂)₃—NMe₂ | XII.5 | | 504 (M + H)+ | 1.14 | 7 |
| 1.35 | H | —C(O)—(CH₂)₂—N⁺Me₃ | XIV.7 | *ᶠ | 531 (M)+ | 1.15 | 7 |
| 1.38 | H | —CH₂C(O)OMe | X.14 | | 475 (M + H)+<br>473 (M − H)− | *ᵈ | *ᵈ |
| 1.39 | H | —(PEG-like group with terminal OH and NHC(O)*) | XIV.8 | | 578 (M + H)+ | 0.73 | 5 |
| 1.40 | H | —CN | X.15 | | 428 (M + H)+ | 0.74 | 4 |
| 1.41 | H | —OC(O)CH₃ | XII.6 | | 461 (M + H)+ | 0.8 | 4 |
| 1.43 | —C(O)—OMe | —H | X.16 | | 461 (M + H)+ | 0.83 | 4 |
| 1.45 | H | —(CH₂)₂C(O)OMe | XII.11 | | 489 (M + H)+ | 0.88 | 4 |
| 1.47 | H | *C(O)NH-CH₂CH₂-O-CH₂CH₂-O-CH₂CH₂-NH₂ | XVIII.1 | Additional step for removal of BOC group *ᵉ | 577 (M + H)+ | 0.68 | 6 |
| 1.49 | H | (extended PEG linker with benzamide-OCH₂CH₂OMe) | XIV.9 | | 755 (M + H)+ | 0.93 | 4 |
| 1.50 | H | —CCH | XI.4 | | 427 (M + H)+<br>425 (M − H)− | 0.84 | 4 |
| 1.51 | H | —C(O)OH | X.17 | Additional ester cleavage step *ᶜ | 447 (M + H)+<br>445 (M − H)− | 0.68 | 6 |

TABLE 13-continued

[Structure: Chloropyrazine carboxamide-guanidine-piperidine-benzyl scaffold with R⁷ (ortho) and R⁸ (para) substituents on the benzyl ring]

| Example | R⁷ | R⁸ | Primary amine applied: | Synthesis comment | ESI mass spectrum | HPLC Retention time (min) | HPLC method |
|---|---|---|---|---|---|---|---|
| 1.52 | H | [2-(1-(3-hydroxypropyl)imidazol-4-yl)ethylaminocarbonyl] | XIV.10 | *f | 596 (M − H)− | 0.89 | 2 |
| 1.54 | H | [2-(2-hydroxyethoxy)ethylaminocarbonyl] | XIV.11 | *f | 534 (M + H)+<br>532 (M − H)− | 0.74 | 6 |
| 1.55 | H | —C(=NH)NH₂ | X.3 | *f | 445 (M + H)+ | 0.61 | 4 |
| 1.56 | H | [N-(PEG-OH/azide)-N-methyl-6-oxo-1,6-dihydropyridine-3-carboxamide] | XIV.5 | | 886 (M + H)+<br>884 (M − H)− | 0.94 | 4 |
| 1.57 | H | [2-(pyridin-3-yl)ethyl] | XX.1 | | 508 (M + H)+<br>506 (M − H)− | 0.70 | 6 |
| 1.58 | H | [2-(6-(2-methoxyethoxy)pyridazin-3-yl)ethyl] | XX.2 | | 583 (M + H)+ | 1.17 | 2 |
| 1.63 | H | [2-hydroxyethylaminosulfonyl] | XXIII.1 | *g | 526 (M + H)+<br>524 (M − H)− | 0.67 | 4 |
| 1.67 | H | [2-acetamidoethylaminosulfonyl] | XXIII.2 | Reaction in DMF at 70° C.; *g | 567 (M + H)+<br>565 (M − H)− | 0.72 | 4 |

*a The respective component (see "synthesis comment") is described in the literature and/or commercially available.
*c Examples 1.51, 1.60, 1.62: The procedure described for example 1.1 yields the respective tert-butylester which is converted into the title compound by stirring in TFA/DCM at r.t. for 2 h and subsequent purifiction by RP-HPLC (modifier: ammonia).
*d Example 1.38: HPLC retention time not determined. Characterization by TLC (Silica; DCM/methanol/aq. ammonia 80:20:2): Rf = 0.55.
*e The BOC protecting group is removed by stirring in TFA/DCM 1:3 at r.t. for 1 h prior to chromatographic purification.
*f Purification by RP-HPLC (modifier: TFA)
*g Purification by RP-HPLC (modifier: ammonia)

Also the following compounds of general formula 1.B are prepared accordingly using the respective primary amine as indicated:

TABLE 14

1.B

[Structure: chloropyrazine carboxamide guanidine piperidinyl benzyl with R7 and R8 substituents]

| Example | R⁷ | R⁸ | Primary amine applied: | Synthesis comment | ESI mass spectrum | HPLC Retention time (min) | HPLC method |
|---|---|---|---|---|---|---|---|
| 1.6 | H | —CH₂—C(O)OMe | XII.13 | | 475 (M + H)+<br>473 (M − H)− | 0.85 | 4 |
| 1.11 | —C(O)—OMe | [HO-CH₂CH₂-O-CH₂CH₂-NH-C(O)-*] | XII.1 | | 592 (M + H)+<br>590 (M − H)− | 1.21 | 5 |
| 1.32 | H | —CCH | *ᵇ | | 427 (M + H)+<br>471 (M + HCOO)− | 1.33 | 1 |
| 1.36 | H | —C(O)OMe | X.12 | | 461 (M + H)+ | 0.82 | 4 |
| 1.44 | H | —OCH₂—C(O)OMe | XII.9 | | 491 (M + H)+ | 0.81 | 6 |
| 1.48 | OMe | —OCH₂—C(O)OMe | XII.10 | | 579 (M + H)+ | 0.86 | 4 |
| 1.64 | —OMe | —C(O)OH | XII.14 | Reaction at 60° C.; *ᶠ | 477 (M + H)+ | 1.17 | 3 |
| 1.65 | H | [HO-CH₂CH₂-O-CH₂CH₂-NH-C(O)-*] | XXV.1 | Reaction in DMF at 80° C. | 534 (M + H)+<br>532 (M − H)− | 0.76 | 4 |

*ᵃ The respective component (see "synthesis comment") is described in the literature and/or commercially available.
*ᵇ The primary amino compound 1-[(3-ethynylphenyl)methyl]piperidin-4-amine is prepared analogously to the procedure described for intermediate XI.4.
*ᶠ Purification by RP-HPLC (modifier: TFA)

Also the following compounds of general formula 1.C are prepared accordingly using the respective primary amine as indicated:

TABLE 15

1.C

[Structure: chloropyrazine carboxamide amidine with Z¹ substituent]

| Example | Z¹ | Primary amine applied: | Synthesis comment | ESI mass spectrum | HPLC Retention time (min) | HPLC method |
|---|---|---|---|---|---|---|
| 1.17 | [methyl 4-((4-methylpiperidin-4-ylamino)methyl)benzoate group] | X.8 | | 475 (M + H)+ | 0.77 | 6 |

TABLE 15-continued

1.C structure: 3,5-diamino-6-chloropyrazine-2-carbonyl guanidine with $Z^1$ substituent

| Example | $Z^1$ | Primary amine applied: | Synthesis comment | ESI mass spectrum | HPLC Retention time (min) | HPLC method |
|---|---|---|---|---|---|---|
| 1.19 | 4-methoxyphenethyl-piperidin-4-yl-NH-* | X.9 | | 447 (M + H)+ | 1.4 | 1 |
| 1.20 | *-HN-piperidin-4-yl-CH2-C(O)-4-methoxyphenyl | X.10 | | 461 (M + H)+ 459 (M − H)− | 1.28 | 1 |
| 1.21 | 4-cyanophenoxyethyl-piperidin-4-yl-NH-* | X.11 | | 458 (M + H)+ | 1.23 | 2 |
| 1.22 | 1-benzylazepan-4-yl-NH-* | *a | 1-benzylazepan-4-amine | 417 (M + H)+ | 1.2 | 2 |
| 1.26 | *-HN-1-benzylpyrrolidin-3-yl | *a | 1-benzyl-pyrrolidin-3-amine | 389 (M + H)+ | 1.73 | 8 |
| 1.27 | *-HN-endo-8-benzyl-8-azabicyclo[3.2.1]octan-3-yl | *a | endo-8-benzyl-8-azabicyclo[3.2.1]octan-3-amine | 429 (M + H)+ | 0.74 | 7 |
| 1.28 | *-HN-exo-8-benzyl-8-azabicyclo[3.2.1]octan-3-yl | *a | exo-8-benzyl-8-azabicyclo[3.2.1]octan-3-amine | 429 (M + H)+ | 1.26 | 7 |
| 1.37 | methyl 2-phenyl-2-(piperidin-4-yl)acetate-NH-* | X.13 | | 461 (M + H)+ | 1.4 | 1 |
| 1.42 | 1-(4-methoxybenzyl)pyrrolidinyl | XII.7 | | 477 (M + H)+ | 0.78 | 4 |

Also compound 1.68 is prepared accordingly (except that the reaction is carried out at 65° C.) from intermediate C.2 and intermediate 12.3

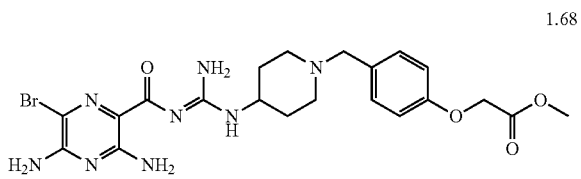 [SMILES: COC(=O)COc1ccc(CN2CCC(N/C(N)=N/C(=O)c3nc(Br)c(N)nc3N)CC2)cc1]

1.68

$C_{21}H_{27}BrN_8O_4$ ESI Mass spectrum: m/z=535 $[M+H]^+$; m/z=569 $[M+Cl]^-$
RP-HPLC: $R_t$=0.55 min (HPLC method 11)

Example 2.1

µl; 1.17 mmol) in THF (100 ml) is stirred at 60° C. for 3d. Volatiles are evaporated and the crude BOC-protected intermediate is further reacted without purification as follows:

A mixture of the intermediate, triethylamine (170 µl; 1.23 mmol) and HATU (147 mg; 0.387 mmol) in DMF (6 ml) and ACN (6 ml) is stirred at ambient temperature for 30 min. The amino component 3-Amino-propylsulphonic acid (98 mg; 0.702 mmol) is added and the mixture is stirred overnight. The mixture is evaporated and the residue is purified by RP-HPLC (modifier: TFA) to yield the BOC-protected amide intermediate which is taken up in DCM and TFA and stirred overnight. Volatiles are evaporated and the residue is taken up in HCl in methanol and evaporated again. The latter is repeated for further two times to yield the title compound.
Yield: 31 mg (15% of theory) $C_{22}H_{30}ClN_9O_5S \times 2HCl$
ESI Mass spectrum: m/z=568 $[M+H]^+$; m/z=566 $[M-H]^-$
RP-HPLC: $R_t$=0.93 min (HPLC method 7)
The following compounds of general formula 2.A are prepared accordingly from starting materials as indicated:

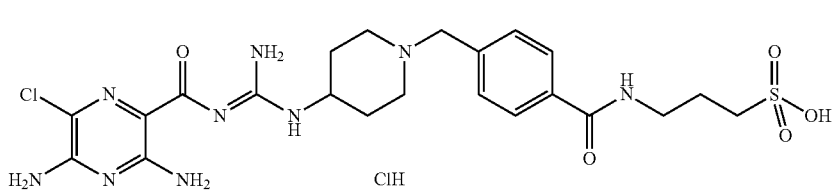

2.1

A mixture of acid example 1.51 (360 mg; 0.427 mmol), BOC-anhydride (247 mg; 1.13 mmol) and triethylamine (230

TABLE 16

2.A

| Example | $Z^2$ | components applied: | Synthesis comment | ESI mass spectrum | HPLC Retention time (min) | HPLC method |
|---|---|---|---|---|---|---|
| 2.2 | ![structure] | 1.51/ *a | (2-{[2-(dimethylamino)ethyl]amino}ethyl)dimethylamine | 588 $(M + H)^+$ | 0.68 | 7 |
| 2.3 | ![structure] | 8.2/ *a | (2-aminoethyl)-trimethyl-ammonium chloride | 531 $(M)^+$ | 1.07 | 1 |
| 2.4 | ![structure] | 1.51/ *a | 2-aminoethyl-sulphonic acid | 554 $(M + H)^+$ | 0.98 | 1 |

TABLE 16-continued

2.A

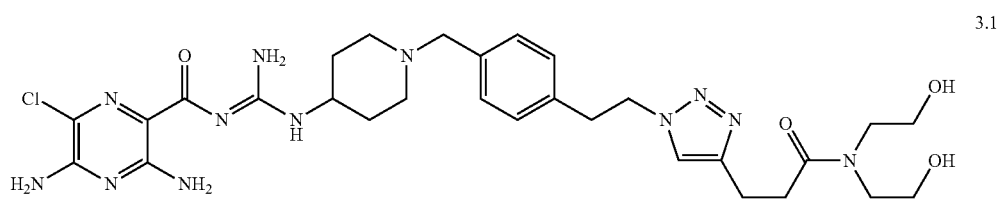 [SMILES: N/C(=N\C(=O)c1nc(Cl)c(N)nc1N)NC1CCN(Cc2ccc(CCn3cc(CCC(=O)N(CCO)CCO)nn3)cc2)CC1]

| Example | $Z^2$ | components applied: | Synthesis comment | ESI mass spectrum | HPLC Retention time (min) | HPLC method |
|---|---|---|---|---|---|---|
| 2.5 | ![structure] | 8.13/ *a | 2-dimethyl-amino-ethylamine | 531 $(M + H)^+$ 529 $(M - H)-$ | 0.66 | 4 |

*a The respective amino component (see "synthesis comment") is described in the literature and/or commercially available.

Example 3.1

3.1

To a mixture of azide component example 1.3 (0.80 g; 1.70 mmol) and the alkyne component II.1 (0.564 ml; 2.37 mmol) in DMF (20 ml) is added a mixture of copper(II) acetate (46 mg; 0.254 mmol) and sodium L-ascorbate (101 mg; 0.51 mmol) in water (2.0 ml). The mixture is stirred at 70° C. overnight and then evaporated to dryness. The residue is purified by silica gel column chromatography (gradient: DCM/(methanol/ammonia 9:1) 95:5→70:30. The crude product is further purified by RP-HPLC (modifier: TFA) to yield the title compound as a TFA salt.

Yield: 0.401 g (36% of theory) $C_{29}H_{41}ClN_{12}O_4 \times 2TFA$

ESI Mass spectrum: m/z=657 $[M+H]^+$; m/z=655 $[M-H]^-$

RP-HPLC: $R_t$=0.77 min (HPLC Method 4)

The following compounds of general formula 3.A, 3.B, 3.C, 3.D, 3.E, 3.F or 3.G are prepared accordingly from starting materials as indicated:

TABLE 17
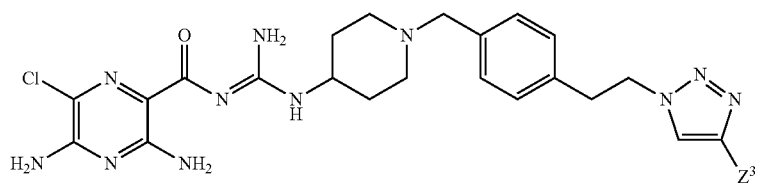
3.A
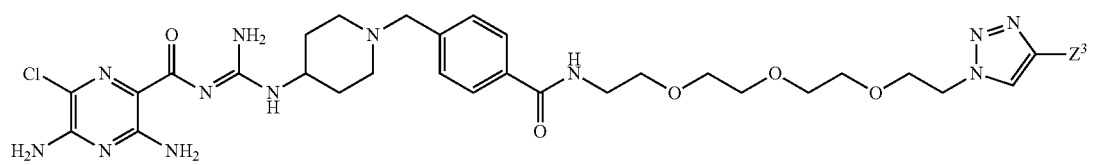
3.B
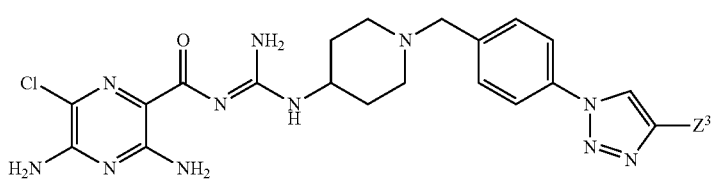
3.C
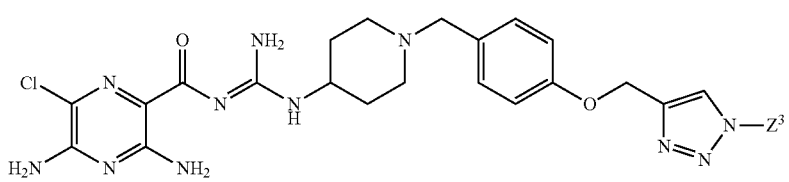
3.D
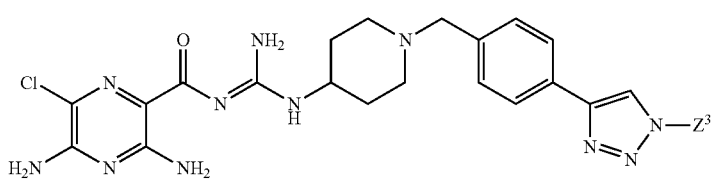
3.E
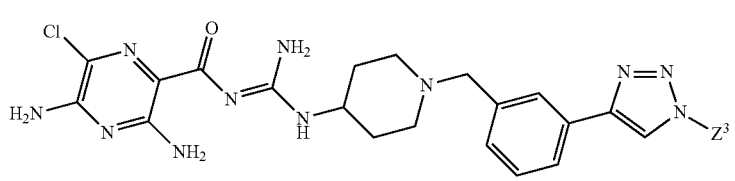
3.F
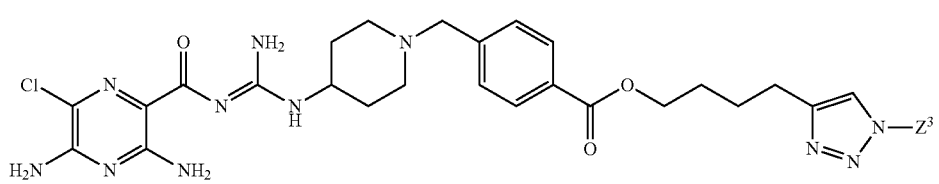
3.G
| Example | General formula | $Z^3$ | Azide/alkyne components applied | Synthesis comment | ESI mass spectrum | HPLC Retention time (min) | HPLC method |
|---|---|---|---|---|---|---|---|
| 3.2 | 3.A | HO-CH₂-CH₂-O-CH₂-* | 1.3/ *a | 2-(prop-2-yn-1-yloxy)ethan-1-ol | 572 (M + H)⁺ | 1.21 | 7 |

TABLE 17-continued

| | | | | | | | |
|---|---|---|---|---|---|---|---|
| 3.3 | 3.A | *-CH2-O-C6H4(m)-C(O)-NH-CH2-CH2-O-CH2-CH2-OH | 1.3/ III.1 | | 735 (M + H)+ | 0.88 | 4 |
| 3.4 | 3.A | —CH2—N(Me)2 | 1.3/ *a | N,N-dimethyl-propargyl-amine | 555 (M + H)+ | 0.69 | 5 |
| 3.5 | 3.A | MeN(CH2*)-C(O)-CH2-CH2-NH-C(O)-O-C(CH3)3 | 1.3/ III.2 | Purification only by silica gel chromatography | 712 (M + H)+ 710 (M − H)− | 0.97 | 4 |
| 3.6 | 3.A | MeN(CH2*)-C(O)-CH2-CH2-NH-CH2-CH2-O-CH2-CH2-O-CH2-CH2-O-C(Ph)3 | 1.3/ IV.1 | Purification only by silica gel chromatography | 516 (M + 2H)++ 1028 (M − H)− | 1.65 | 3 |
| 3.7 | 3.A | C(CH2OH)3-CH2-O-CH2* | 1.3/ V.1 | Additional deprotection step*b | 646 (M + H)+ 644 (M − H)− | 1.00 | 2 |
| 3.8 | 3.B | —CH2—O—CH2—CH2—OH | 1.7/ *a | 2-(prop-2-yn-1-yloxy)ethan-1-ol | 747 (M + H)+ 745 (M − H)− | 1.22 | 1 |
| 3.9 | 3.B | —CH2—O—CH2—BF3− | 1.7/ *a | Potassium propargyloxy-methyl-trifluoro- | 783 (M)− | 0.81 | 4 |
| 3.10 | 3.B | *-CH2-piperazine-NH | 1.7/ *a | 1-propargyl-piperazine | 769 (M − H)− | 0.75 | 4 |
| 3.11 | 3.C | —CH2—O—CH2—CH2—OH | 1.10/ *a | 2-(prop-2-yn-1-yloxy)ethan-1-ol | 544 (M + H)+ 542 (M − H)− | 1.05 | 1 |
| 3.12 | 3.C | (HOCH2CH2)2N-C(O)-CH2-CH2* | 1.10/ II.1 | | 629 (M + H)+ 627 (M − H)− | 1.02 | 1 |
| 3.13 | 3.C | —CH2—CH2—C(O)OH | 1.10/ *a | 4-pentynoic acid | 542 (M + H)+ 540 (M − H)− | 1.46 | 1 |
| 3.14 | 3.C | —CH2—O—CH2—BF3− | 1.10/ *a | Potassium propargyloxy-methyl-trifluoro-borate | 580 (M)− | 0.71 | 6 |
| 3.15 | 3.C | —CH2—N(Me)2 | 1.10/ *a | N,N-dimethyl-propargyl-amine | 527 (M + H)+ 525 (M − H)− | 0.65 | 6 |

TABLE 17-continued

| | | | | | | | |
|---|---|---|---|---|---|---|---|
| 3.16 | 3.C | 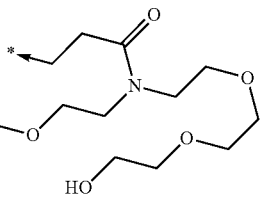 | 1.10/ III.3 | Additional deprotection step*c | 805 (M + H)+ 803 (M − H)− | 1.24 | 2 |
| 3.17 | 3.C | 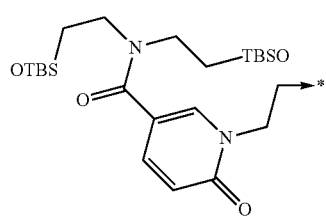 | 1.10/ VI.1 | Purification only by silica gel chromatography | 950 (M + H)+ | 2.03 | 2 |
| 3.18 | 3.C | 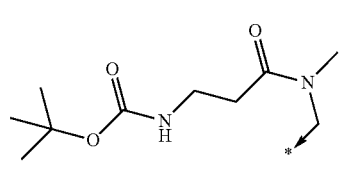 | 1.10/ III.2 | Purification only by silica gel chromatography | 684 (M + H)+ | 0.97 | 4 |
| 3.19 | 3.C | 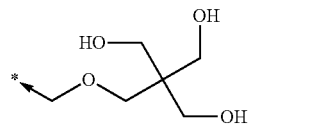 | 1.10/ V.1 | Additional deprotection step *b | 618 (M + H)+ | 0.93 | 2 |
| 3.20 | 3.C | 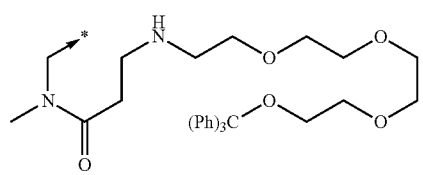 | 1.10/ IV.1 | Purification only by silica gel chromatography | 1002 (M + H)+ 502 (M + H)++ | 1.72 | 3 |
| 3.21 | 3.D | —(CH₂CH₂O)₄H | *a/ 1.4 | 2-{2-[2-(2-azido-ethoxy)ethoxy]-ethoxy}ethan | 676 (M + H)+ 720 (M + HCOO)− | 0.97 | 7 |
| 3.22 | 3.D | —(CH₂CH₂O)₃CH₂CH₂—N₃ | *a/ 1.4 | 2-{2-[2-(2-azido-ethoxy)ethoxy]-ethoxy}-1-azidoethane | 701 (M + H)+ | 2.63 | 9 |
| 3.23 | 3.D | —(CH₂CH₂O)₆C(Ph)₃ | VII.1/ 1.4 | Purification only by silica gel chromatography | 1006 (M + H)+ | 1.21 | 7 |
| 3.24 | 3.D | —(CH₂CH₂O)₃H | VII.2/ 1.4 | | 632 (M + H)+ | 1.01 | 7 |
| 3.25 | 3.D | 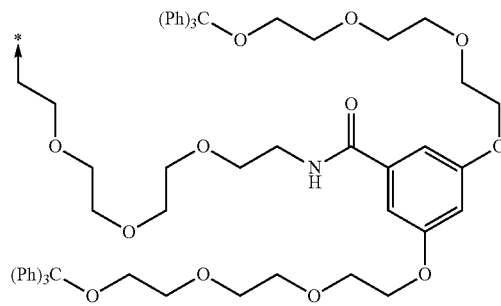 | VIII.2/ 1.4 | Purification only by silica gel chromatography | 1559 (M + H)+ 780.5 (2M + 2H)++ | 2.19 | 2 |
| 3.26 | 3.E | —(CH₂CH₂O)₄H | *a/ 1.50 | 2-{2-[2-(2-azido-ethoxy)ethoxy]-ethoxy}ethan | 646 (M + H)+ | 0.98 | 7 |
| 3.27 | 3.E | —(CH₂CH₂O)₆H | VII.1/ | | 734 (M + H)+ | 0.87 | 4 |

TABLE 17-continued

| | | | | | | | |
|---|---|---|---|---|---|---|---|
| 3.28 | 3.E | —(CH₂CH₂O)₃C(Ph)₃ | VII.2/ 1.50 | Purification only by silica gel chromatography | 844 (M + H)⁺ | 1.88 | 1 |
| 3.29 | 3.E | —(CH₂CH₂O)₈H | *ᵃ/ 1.50 | 23-amino-3,6,9,12,15,18,21-heptaoxatricosan-1-ol | 822 (M + H)⁺ | 1.08 | 7 |
| 3.30 | 3.E | —(CH₂CH₂O)₂C(Ph)₃ | VII.3/ 1.50 | Purification only by silica gel chromatography | 800 (M + H)⁺ | 2.01 | 1 |
| 3.31 | 3.E | [structure: bis-trityl-PEG benzamide] | VIII.1/ 1.50 | Purification only by silica gel chromatography | 1133 (M − 2 Trityl + 3H)⁺ | 2.35 | 1 |
| 3.32 | 3.E | —(CH₂CH₂O)₃CH₂CH₂—N₃ | *ᵃ/ 1.50 | 2-{2-[2-(2-azidoethoxy)ethoxy]ethoxy}-1-azidoethan | 671 (M + H)⁺ 669 (M − H)− | 0.92 | 4 |
| 3.33 | 3.E | [structure: triethyl ammonium benzyl] | XXI.1/ 1.50 | | 344 (M + H)⁺⁺ 229 (M + 2H)³⁺ | 1.22 | 1 |
| 3.34 | 3.E | [structure: bis-trityl-PEG benzamide] | VIII.2/ 1.50 | Purification only by silica gel chromatography | 776 (M + H + Na)⁺⁺ | 2.27 | 2 |
| 3.35 | 3.E | [structure: amino-PEG-OH] | IX.1/ 1.50 | Additional deprotection step *ᵈ | 777 (M + H)⁺ | 0.76 | 6 |
| 3.36 | 3.F | —(CH₂CH₂O)₄H | *ᵃ/ 1.32 | 2-{2-[2-(2-azidoethoxy)ethoxy]ethoxy}ethan | 646 (M + H)⁺ | 1.2 | 1 |
| 3.37 | 3.F | —(CH₂CH₂O)₆C(Ph)₃ | VII.1/ 1.32 | Purification only by silica gel chromatography | 976 (M + H)⁺ | 1.97 | 1 |

TABLE 17-continued

| | | Structure | | Synthesis comment | MS | Rt [min] | Method |
|---|---|---|---|---|---|---|---|
| 3.38 | 3.F | [structure: N,N,N-triethyl benzylammonium with ethyl linker] | XXI.1/ 1.32 | | 687 (M)+ | 1.25 | 1 |
| 3.39 | 3.F | [structure: bis-trityl-PEG benzamide] | VIII.2/ 1.32 | Purification only by silica gel chromatography | 776.5 (M + Na + H)++ | 2.16 | 2 |
| 3.40 | 3.F | [structure: bis-trityl-PEG amine] | IX.1/ 1.32 | Purification only by silica gel chromatography | 1019 (M + H)+ | 1.86 | 2 |
| 3.41 | 3.F | [structure: bis-trityl-PEG benzamide, longer] | VIII.1/ 1.32 | Purification only by silica gel chromatography | 1617 (M + H)+ | 2.24 | 3 |
| 3.42 | 3.G | —(CH$_2$CH$_2$O)$_4$H | *a/ 1.9 | | 746 (M + H)+ 744 (M − H)− | 1.40 | 1 |
| 3.43 | 3.A | [structure: morpholine propanoyl] | 1.3/ *e | Reaction at 80° C. for 5 days | 639 (M + H)+ 637 (M − H)− | 1.23 | 2 |
| 3.44 | 3.A | [structure: 4-acetylpiperazine propanoyl] | 1.3/*f | Reaction at 80° C. for 5 days | 680 (M + H)+ 678 (M − H)− | 1.20 | 2 |

*[a] The respective component (see "synthesis comment") is described in the literature and/or commercially available.
*[b] Examples 3.7 and 3.19: The procedure described for example 3.1 yields a benzylidene-protected intermediate which is deprotected by heating overnight in a mixture of hydrochloric acid (4 mol/l) and methanol. Purification by RP-HPLC (modifier: TFA).
*[c] Example 3.16: The procedure described for example 3.1 yields a trityl-protected intermediate which is deprotected using the procedure described for the synthesis of example 5.1.
*[d] Example 3.35: The trityl group is removed prior to chromatographic purification as described for the synthesis of example 5.1.
*[e] Alkyne component: 1-(morpholin-4-yl)pent-4-yn-1-one
*[f] Alkyne component 1-(4-acetylpiperazin-1-yl)pent-4-yn-1-one prepared as described for 1-(morpholin-4-yl)pent-4-yn-1-one Example 4.1

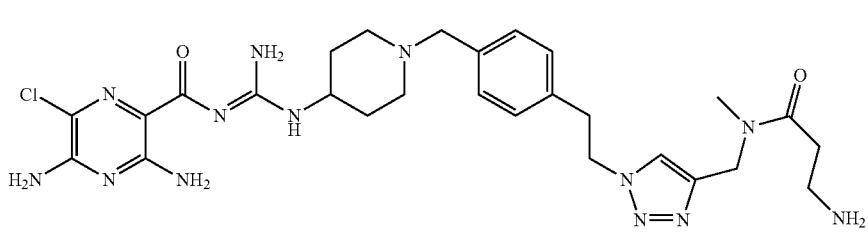

A mixture of the BOC-protected compound example 3.5 (300 mg; 0.421 mmol), HCl in dioxan (4 mol/l; 2.0 ml; 8.0 mmol) and methanol (1.0 ml) is stirred at ambient temperature for 2 h. The mixture is evaporated to dryness to the title compound as a hydrochloride salt.

Yield: 0.282 g (98% of theory) $C_{27}H_{38}ClN_{13}O_2 \times 2HCl$
ESI Mass spectrum: m/z=612 [M+H]$^+$; m/z=610 [M−H]$^-$
RP-HPLC: $R_t$=0.72 min (HPLC Method 4)

The following compounds of general formula 3.0 are prepared accordingly from starting materials as indicated:

Yield: 29 mg (31% of theory) $C_{33}H_{50}ClN_{11}O_8$
ESI Mass spectrum: m/z=764 [M+H]$^+$; m/z=762 [M−H]$^-$ HPLC analytics: RT=1.28 min (HPLC method 7)

The following compounds of general formula 3.A, 3.C, 3.D, 3.E or 3.F are prepared accordingly from starting materials as indicated:

TABLE 18

| Example | General formula | $Z^3$ | BOC-protected starting material | ESI mass spectrum | HPLC Retention time (min) | HPLC method |
|---|---|---|---|---|---|---|
| 4.2 | 3.C |  | 3.18 | 584 (M + H)$^+$<br>582 (M − H)− | 0.98 | 4 |

Example 5.1

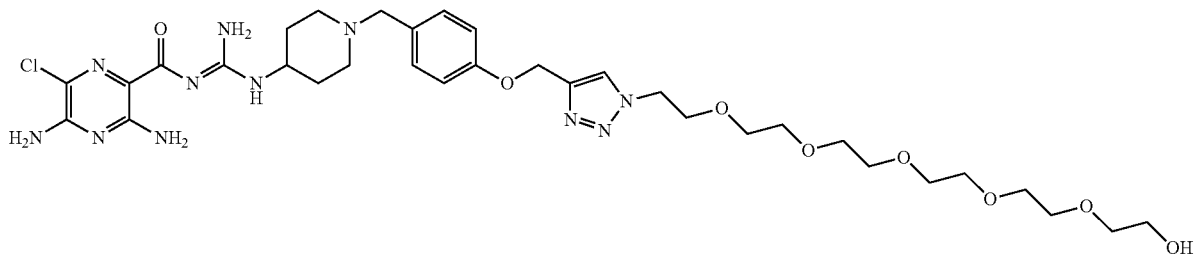

A mixture of Trityl-protected compound example 3.23 (0.124 g; 0.123 mmol) and formic acid (1.0 ml) in DCM (1 ml) is stirred at ambient temperature for 1 h. Volatiles are evaporated and the residue is purified by silica gel column chromatography (gradient: DCM/(Methanol/aq. Ammonia 9:1) 95:5→70:30 to yield the title compound.

TABLE 20
| Example | General formula | Z³ | Trityl-protected starting material | ESI mass spectrum | HPLC Retention time (min) | HPLC method |
|---|---|---|---|---|---|---|
| 5.2 | 3.A | 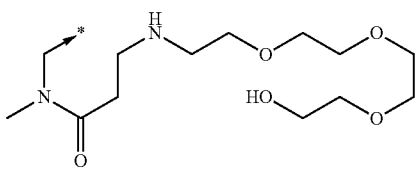 | 3.6 | 786 (M − H)−<br>394 (M + 2H)++ | 0.76 | 4 |
| 5.3 | 3.C | 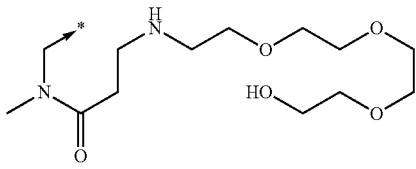 | 3.20 | 760 (M + H)+ | 0.78 | 4 |
| 5.4 | 3.E | —(CH$_2$CH$_2$O)$_3$H | 3.28 | 602 (M + H)+ | 1.18 | 1 |
| 5.5 | 3.E | 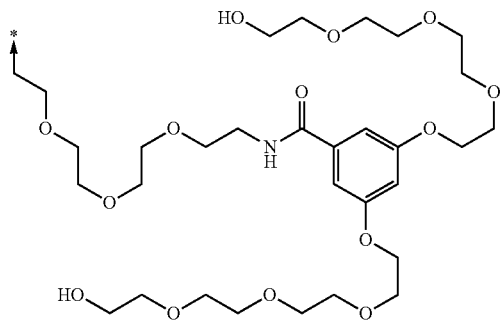 | 3.31 | 1131 (M − H)− | 0.93 | 5 |
| 5.6 | 3.E | —(CH$_2$CH$_2$O)$_2$H | 3.30 | 558 (M + H)+ | 0.73 | 5 |
| 5.7 | 3E | 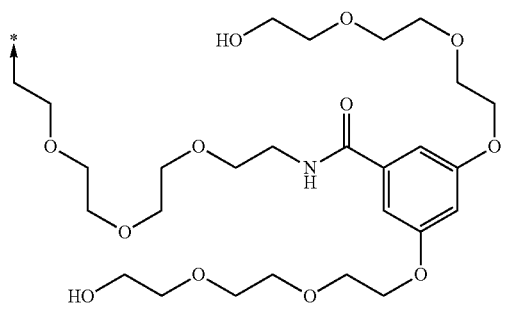 | 3.34 | 1045 (M + H)+<br>523 (M + H)++ | 1.33 | 2 |
| 5.8 | 3.D | 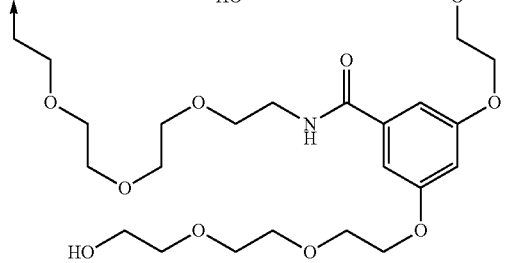 | 3.25 | 1075 (M + H)+<br>538 (M + 2H)++ | 1.43 | 2 |
| 5.9 | 3.F | —(CH$_2$CH$_2$O)$_6$H | 3.37 | 734 (M + H)+ | 0.83 | 6 |
| 5.10 | 3.F | 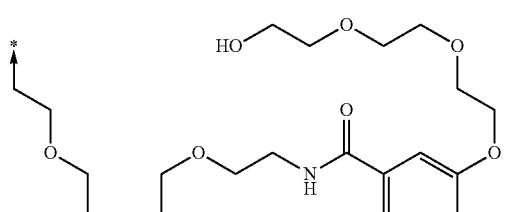 | 3.39 | 1045 (M + H)+ | 1.48 | 2 |

Example 6.1

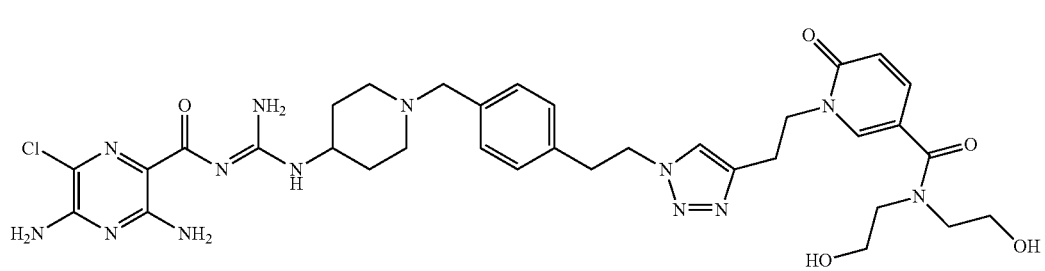

HPLC analytics: RT=1.09 min (Method 1)

Example 8.1

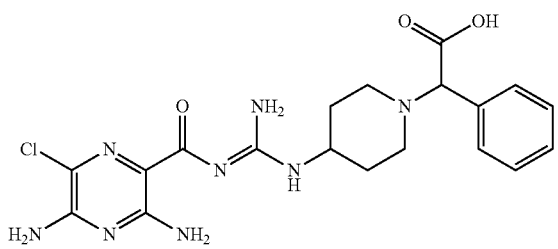

To a mixture of the TBS-protected compound example 3.17 (170 mg; 0.179 mmol) and tetrabutylammonium fluoride on silica (1.5 mmol/g; 0.30 g; purchased from Fluka) in THF (3 ml) is added aqueous hydrochloric acid (1 mol/l; 0.5 ml) and methanol (10 ml). The mixture is stirred at ambient temperature for 5 h. Volatiles are evaporated and the residue is purified by silica gel column chromatography (gradient: DCM/(Methanol/aq. Ammonia 9:1) 100:0→70:30 to yield the title compound.

Yield: 71 mg (55% of theory) $C_{32}H_{40}ClN_{13}O_5$

ESI Mass spectrum: m/z=722 [M+H]$^+$; m/z=720 [M−H]$^−$

HPLC analytics: RT=1.05 min (HPLC method 3)

Example 7.1

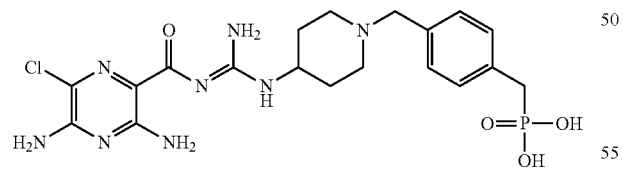

To the phosphonic ester example 1.8 (600 mg; 1.09 mmol) in DCM (5 ml) under argon atmosphere is added bromotrimethylsilane (2.87 ml; 21.8 mmol). The mixture is refluxed for 4 h, then methanol is added and the mixture is stirred for further 30 min at r.t. Volatiles are evaporated and the residue is purified by RP-HPLC (modifier: ammonia) to yield the title compound.

Yield: 300 mg (56% of theory) $C_{19}H_{26}ClN_8O_4P$

ESI Mass spectrum: m/z=497 [M+H]$^+$; m/z=495 [M−H]$^−$

To a solution of the ester compound example 1.37 (150 mg; 0.218 mmol) in methanol (4 ml) is added aqueous NaOH solution (4 mol/l; 218 μl; 0.871 mmol). The mixture is stirred for 40 min at 50° C., then neutralised by addition of aqueous hydrochloric acid. Volatiles are evaporated and the residue is purified by silica gel column chromatography (gradient: DCM/(Methanol/aq. Ammonia 9:1) 95:5→75:25 to yield the title compound.

Yield: 20 mg (19% of theory) $C_{19}H_{23}ClN_8O_3$

ESI Mass spectrum: m/z=447 [M+H]$^+$; m/z=445 [M−H]$^−$

HPLC analytics: RT=0.73 min (HPLC method 6)

The following compounds of general formula 1.A or 1.B are prepared accordingly from starting materials as indicated:

TABLE 21

| Example | General formula | R⁷ | R⁸ | ester starting material | Synthesis comment | ESI mass spectrum | HPLC Retention time (min) | HPLC method |
|---|---|---|---|---|---|---|---|---|
| 8.2 | 1.B | H | —C(O)OH | 1.36 | Purification by silica gel chromatography (gradient: DCM/(Methanol/glacial acetic acid 9:1) 95:5 → 50:50 | 447 (M + H)⁺ | 1.15 | 7 |
| 8.3 | 1.A | H | —P(O)(OH)OEt | 1.13 | Saponification conditions: Stirred for 3 d at r.t. in Ethanol/aq. NaOH | 511 (M + H)⁺ | 0.87 | 1 |
| 8.4 | 1.A | H | (5-carboxy-2-oxo-1(2H)-pyridinyl) | 1.16 | Saponifiaction conditions: 1 h at 70° C.; Purification by RP-HPLC (modifier: NH₃) | 540 (M + H)⁺ | 1.03 | 1 |
| 8.6 | 1.B | —C(O)—OH | HOCH₂CH₂OCH₂CH₂NHC(O)— | 1.11 | Purification: Freeze-drying of neutralised aqueous phase after extraction with DCM. | 578 (M + H)⁺ | 1.25 | 6 |
| 8.7 | 1.A | —C(O)—OH | H | 1.43 | Purification by RP-HPLC (modifier: TFA) | 447 (M + H)⁺ | 0.75 | 6 |
| 8.8 | 1.A | H | —OCH₂—C(O)OH | 1.30 | Purification by RP-HPLC (modifier: TFA) | 477 (M + H)⁺ | 1.55 | 8 |
| 8.9 | 1.A | —OCH₃ | —C(O)OH | 1.1 | Saponifiaction conditions: 3 d at r.t. with addition of THF | 477 (M + H)⁺ | 1.04 | 2 |
| 8.10 | 1.B | H | —CH₂—C(O)OH | 1.6 | Purification by RP-HPLC (modifier: TFA) | 461 (M + H)⁺ | 0.77 | 4 |
| 8.11 | 1.A | —Cl | —C(O)OH | 1.12 | Saponification at 70° C.; Purification by preparative TLC (Silica; DCM/MeOH/aq. Ammonia 70:30:3) | 481 (M + H)⁺ | 0.74 | 6 |
| 8.12 | 1.A | H | (5-carboxy-1-ethyl-2-oxo-1(2H)-pyridinyl) | 1.5 | Saponification overnight at 70° C.; Purification by preparative TLC (Silica; DCM/MeOH/aq. Ammonia 80:20:2) | 554 (M + H)⁺ | 1.25 | 10 |
| 8.13 | 1.A | H | —CH₂—C(O)OH | 1.38 | | 461 (M + H)⁺ 459 (M − H)− | 0.75 | 4 |
| 8.14 | 1.A | H | —CH₂CH₂—C(O)OH | 1.45 | Purification by RP-HPLC (modifier: TFA) | 475 (M + H)⁺ | 0.80 | 4 |
| 8.15 | 1.B | H | —OCH₂—C(O)OH | 1.44 | Purification by RP-HPLC (modifier: TFA) | 477 (M + H)⁺ 475 (M − H)− | 0.77 | 4 |

Also the following compounds of general formula 1.C are prepared accordingly from starting materials as indicated:

TABLE 22

| Example | Y¹ | ester starting material | Synthesis comment | ESI mass spectrum | HPLC Retention time (min) | HPLC method |
|---|---|---|---|---|---|---|
| 8.5 | | 1.53 | Purification by RP-HPLC (modifier: TFA) | 551 (M + H)⁺ | 0.72 | 4 |
| 8.16 | | 1.42 | Purification by RP-HPLC (modifier: TFA) | 463 (M + H)⁺ 461 (M − H)− | 0.69 | 4 |

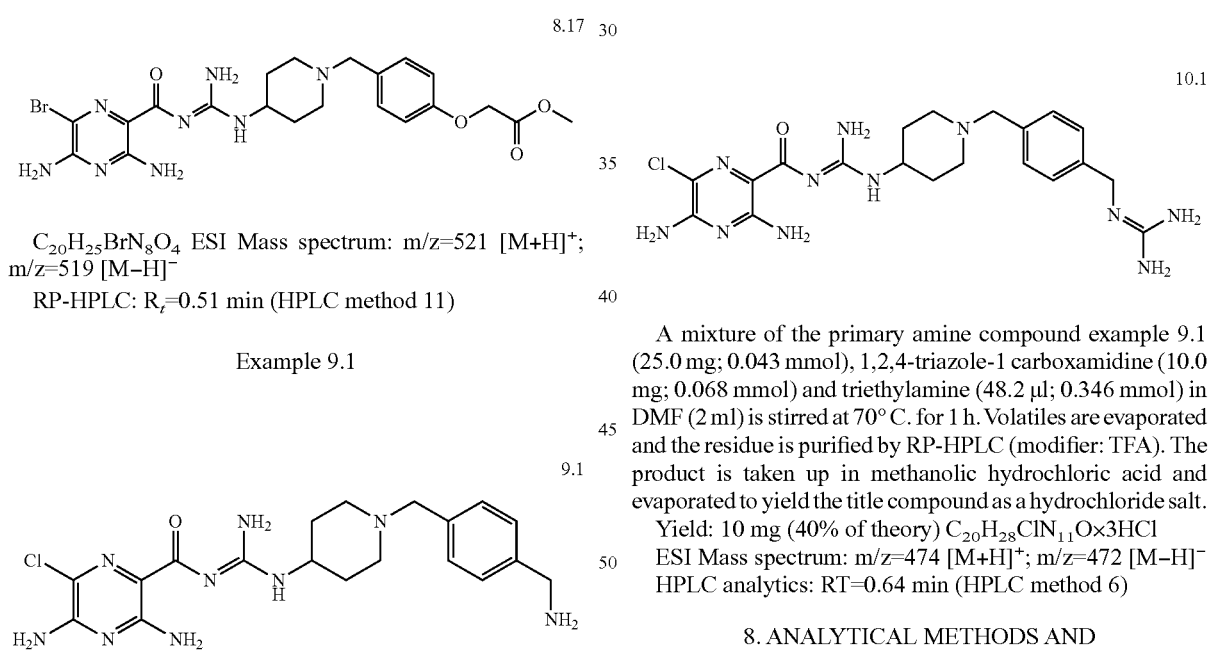

Also compound 8.17 is prepared accordingly (Purification by RP-HPLC with modifier TFA) from example 1.68.

8.17

$C_{20}H_{25}BrN_8O_4$ ESI Mass spectrum: m/z=521 [M+H]⁺; m/z=519 [M−H]⁻

RP-HPLC: $R_f$=0.51 min (HPLC method 11)

Example 9.1

9.1

A mixture of the nitrile compound example 1.40 (1.00 g; 2.34 mmol) and Raney-Nickel (500 mg) in methanolic ammonia solution (50 ml) is shaken under hydrogen (50 psi) for 8.5 h at 50° C. The catalyst is filtered off with suction and the filtrate is evaporated. The residue is taken up in DMF (12 ml), insolubles are removed by filtration. The filtrate is evaporated and the crude product is purified by RP-HPLC (modifier: TFA), taken up in methanolic hydrochloric acid, and evaporated to dryness to yield the title compound as a hydrochloride salt.

Yield: 28 mg (2% of theory) $C_{19}H_{26}ClN_9O \times 4HCl$

ESI Mass spectrum: m/z=432 [M+H]⁺; m/z=430 [M−H]⁻

HPLC analytics: RT=0.60 min (HPLC Method 4)

Example 10.1

10.1

A mixture of the primary amine compound example 9.1 (25.0 mg; 0.043 mmol), 1,2,4-triazole-1 carboxamidine (10.0 mg; 0.068 mmol) and triethylamine (48.2 μl; 0.346 mmol) in DMF (2 ml) is stirred at 70° C. for 1 h. Volatiles are evaporated and the residue is purified by RP-HPLC (modifier: TFA). The product is taken up in methanolic hydrochloric acid and evaporated to yield the title compound as a hydrochloride salt.

Yield: 10 mg (40% of theory) $C_{20}H_{28}ClN_{11}O \times 3HCl$

ESI Mass spectrum: m/z=474 [M+H]⁺; m/z=472 [M−H]⁻

HPLC analytics: RT=0.64 min (HPLC method 6)

8. ANALYTICAL METHODS AND PREPARATIVE CHROMATOGRAPHY

As a rule, ¹H-NMR and mass spectra have been obtained for the compounds prepared. Mass peaks given (e.g. (M+H)⁺, (M+HCOO)⁻) refer to monoisotopic molecular weight. $R_f$ values from TLC are determined using ready-made silica gel 60 TLC plates $F_{254}$ (E. Merck, Darmstadt, Item no. 1.05714) without chamber saturation or using ready-made aluminium oxide 60 $F_{254}$ TLC plates (E. Merck, Darmstadt, Item no. 1.05713) without chamber saturation. The ratios given for the eluents relate to units by volume of the solvent in question. The units by volume for $NH_3$ relate to a concentrated solution of $NH_3$ in water. For silica gel chromatographic purifications, silica gel made by Millipore (MATREX™, 35-70 my) is used.

Preparative Thin Layer Chromatochraphy (TLC):

Preparative TLC plates from Merck (PLC Silica gel 60 $E_{254+366}$, 2 mm) are used. Product containing bands are scraped off and the resulting product-on-silica powder is extracted with DCM, methanol or a mixture thereof (depending on product solubility). Silica is filtered off and the filtrate is evaporated to dryness to yield the purified compound.

Preparative HPLC:

Stationary Phase:

XBridge C18; 10 μm or Sunfire C18; 10 μm (both from waters, www.waters.com)

Mobile Phase:

water/methanol gradient with addition of either TFA or ammonia as modifier as indicated.

Analytical HPLC/MS Methods

The HPLC retention times given are measured under the following parameters:

HPLC Method 1

| Column XBridge C18, 4.6 × 30 mm, 2.5 μm (Waters) | | | | |
|---|---|---|---|---|
| Gradient time [min] | % Sol [H2O, 0.1% TFA] | % Sol [Methanol, 0.1% TFA] | Flow [ml/min] | Temp [° C.] |
| 0.0 | 95 | 5 | 4 | 60 |
| 0.05 | 95 | 5 | 3 | 60 |
| 2.05 | 0 | 100 | 3 | 60 |
| 2.10 | 0 | 100 | 4 | 60 |
| 2.35 | 0 | 100 | 4 | 60 |

HPLC Method 2

| Column XBridge C18, 4.6 × 30 mm, 2.5 μm (Waters) | | | | |
|---|---|---|---|---|
| Gradient time [min] | % Sol [H2O, 0.1% TFA] | % Sol [Methanol] | Flow [ml/min] | Temp [° C.] |
| 0.0 | 95 | 5 | 4 | 60 |
| 0.05 | 95 | 5 | 3 | 60 |
| 2.05 | 0 | 100 | 3 | 60 |
| 2.10 | 0 | 100 | 4.5 | 60 |
| 2.40 | 0 | 100 | 4.5 | 60 |

HPLC Method 3

| Column Sunfire C18, 4.6 × 30 mm, 2.5 μm (Waters) | | | | |
|---|---|---|---|---|
| Gradient time [min] | % Sol [H2O, 0.1% TFA] | % Sol [Methanol] | Flow [ml/min] | Temp [° C.] |
| 0.0 | 95 | 5 | 4 | 60 |
| 0.05 | 95 | 5 | 3 | 60 |
| 2.05 | 0 | 100 | 3 | 60 |
| 2.10 | 0 | 100 | 4.5 | 60 |
| 2.40 | 0 | 100 | 4.5 | 60 |

HPLC Method 4

| Column Sunfire C18, 3 × 30 mm, 2.5 μm (Waters) | | | | |
|---|---|---|---|---|
| Gradient time [min] | % Sol [H2O, 0.1% TFA] | % Sol [Methanol] | Flow [ml/min] | Temp [° C.] |
| 0.0 | 95 | 5 | 1.8 | 60 |
| 0.25 | 95 | 5 | 1.8 | 60 |
| 1.70 | 0 | 100 | 1.8 | 60 |
| 1.75 | 0 | 100 | 2.5 | 60 |
| 1.90 | 0 | 100 | 2.5 | 60 |

HPLC Method 5

| Column XBridge C18, 3 × 30 mm, 2.5 μm (Waters) | | | | |
|---|---|---|---|---|
| Gradient time [min] | % Sol [H2O, 0.1% TFA] | % Sol [Methanol, 0.1% TFA] | Flow [ml/min] | Temp [° C.] |
| 0.0 | 95 | 5 | 2.2 | 60 |
| 0.30 | 95 | 5 | 2.2 | 60 |
| 1.50 | 0 | 100 | 2.2 | 60 |
| 1.55 | 0 | 100 | 2.9 | 60 |
| 1.65 | 0 | 100 | 2.9 | 60 |

HPLC Method 6

| Column XBridge C18, 3 × 30 mm, 2.5 μm (Waters) | | | | |
|---|---|---|---|---|
| Gradient time [min] | % Sol [H2O, 0.1% TFA] | % Sol [Methanol] | Flow [ml/min] | Temp [° C.] |
| 0.0 | 95 | 5 | 2.2 | 60 |
| 0.30 | 95 | 5 | 2.2 | 60 |
| 1.50 | 0 | 100 | 2.2 | 60 |
| 1.55 | 0 | 100 | 2.9 | 60 |
| 1.65 | 0 | 100 | 2.9 | 60 |

HPLC Method 7

Solvent A: Water+0.1% formic acid; Solvent B: Acetonitrile+0.1% formic acid

Gradient:

| Time (min) | % A | % B | Flow rate (ml/min) |
|---|---|---|---|
| 0.00 | 95.0 | 5.0 | 1.5 |
| 2.00 | 0.0 | 100 | 1.5 |
| 2.50 | 0.0 | 100 | 1.5 |
| 2.60 | 95.0 | 5.0 | 1.5 |

Column: X-terra™ MS C18 2.5 μm 4.6 mm×30 mm (Waters); Temperature: r.t. (ca. 25° C.)

HPLC Method 8

Solvent A: Water+0.1% formic acid; Solvent B: Acetonitrile+0.1% formic acid

Gradient:

| Time (min) | % A | % B | Flow rate (ml/min) |
|---|---|---|---|
| 0.00 | 95.0 | 5.0 | 1.00 |
| 0.10 | 95.0 | 5.0 | 1.00 |
| 3.10 | 2.00 | 98.00 | 1.00 |
| 4.50 | 2.00 | 98.00 | 1.00 |
| 5.00 | 95.0 | 5.0 | 1.00 |

Column: X-terra™ MS C18 2.5 μm 4.6 mm×30 mm (Waters); Temperature: r.t. (ca. 25° C.)

HPLC Method 9

Solvent A: Water+0.1% formic acid; Solvent B: Acetonitrile+0.1% formic acid

Gradient:

| Time (min) | % A | % B | Flow rate (ml/min) |
|---|---|---|---|
| 0.00 | 95.0 | 5.0 | 1.5 |
| 2.00 | 0.0 | 100 | 1.5 |
| 2.50 | 0.0 | 100 | 1.5 |
| 2.60 | 95.0 | 5.0 | 1.5 |

Column: X-terra™ MS C18 2.5 μm 4.6 mm×30 mm (Waters); Temperature: r.t. (ca. 25° C.)

HPLC Method 10

Solvent A: Water+0.1% formic acid; Solvent B: Acetonitrile+0.1% formic acid

Gradient:

| Time (min) | % A | % B | Flow rate (ml/min) |
|---|---|---|---|
| 0.00 | 95.0 | 5.0 | 1.5 |
| 2.00 | 0.0 | 100 | 1.5 |
| 2.50 | 0.0 | 100 | 1.5 |
| 2.60 | 95.0 | 5.0 | 1.5 |

Column: X-terra™ MS C18 2.5 μm 4.6 mm×30 mm (Waters); Temperature: r.t. (ca. 25° C.)

HPLC Method 11

Solvent A: water+0.1% TFA; Solvent B: acetonitrile

| time (min | % A | % B | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Column: Sunfire, 3×30 mm, 2.5 μm (Waters)

The following abbreviations are used above and hereinafter:

ACN Acetonitrile
BOC tert-Butoxycarbonyl
CDI 1,1'-Carbonyldiimidazole
DCM Methylene chloride
DIPEA Diisopropyl-ethylamine
DMF N,N-Dimethylformamide
ESI Electrospray ionization
HATU O-(7-Azabenzotriazol-1-yl)-N,N,N',N'-tetramethyluronium hexafluorophosphate
Ph Phenyl
r.t. ambient temperature (about 20° C.)
TBS tert-Butyl-dimethylsilyl
TBTU 2-(1H-Benzotriazol-1-yl)-1,1,3,3-tetramethyluronium-tetrafluoroborate
TEA Triethylamine
THF Tetrahydrofuran
Tr Triphenylmethyl
Fmoc 9H-Fluoren-9-yl-methoxycarbonyl
TFA Trifluoroacetic acid
TLC Thin layer chromatography

arrow and asterisk indicate the binding site, i.e. the point of attachment (here: atom "A") within a chemical entity (here exemplified by the group "A-R")

9. PHARMACOLOGICAL TEST METHOD

Ussing Chamber:

Mouse kidney M-1 cells were cultivated in DMEM containing 5% FCS and 5 μM dexamethasone for 10 to 12 days on polyester transwell filters. Filters were inserted into a teflon-coated well-plate which fit into the in-house ussing chamber system. Prior to measurement the medium of M-1 cells was replaced with Caco-2 transport buffer (Invitrogen, Germany). During measurements, the Ussing chamber temperature was kept at 37° C. Short circuit currents (I_sc) were measured in the voltage-clamp mode using an in-house built amplifier (Boehringer Ingelheim, Biberach) with the software package Lab View for data acquisition and analysis. The transepithelial electrical resistance (TEER) was determined by the application of voltage steps of ±5 mV every 5 sec. Compounds were administered at a final concentration of 3 μM or at increasing concentrations (1-3-10 μM) to the apical solution. At the end of each experiment the amiloride sensitive I_SC was measured by adding 3 μM amiloride to the apical compartment. Results are expressed as inhibition in percent of the amiloride effect or as $IC_{50}$. With the example compounds given above, the following $IC_{50}$ values were determined in the Ussing Chamber assay:

| Example | 1.1 | 1.2 | 1.3 | 1.4 | 1.5 | 1.6 | 1.7 | 1.8 | 1.9 | 1.10 | 1.11 | 1.12 |
|---|---|---|---|---|---|---|---|---|---|---|---|---|
| $IC_{50}$ [nM] | 5 | 10 | 4 | 4 | 7 | 4 | 4 | 10 | 8 | 6 | 4 | 4 |
| Example | 1.13 | 1.14 | 1.15 | 1.16 | 1.17 | 1.18 | 1.19 | 1.20 | 1.21 | 1.22 | 1.23 | 1.24 |
| $IC_{50}$ [nM] | 5 | 1 | 7 | 17 | 66 | 7 | 12 | 11 | 11 | 14 | 2 | 3 |
| Example | 1.25 | 1.26 | 1.27 | 1.28 | 1.29 | 1.30 | 1.31 | 1.32 | 1.33 | 1.34 | 1.35 | 1.36 |
| $IC_{50}$ [nM] | 6 | 20 | 49 | 16 | 2 | 8 | 7 | 7 | 15 | 5 | 2 | 3 |
| Example | 1.37 | 1.38 | 1.39 | 1.40 | 1.41 | 1.42 | 1.43 | 1.44 | 1.45 | 1.46 | 1.47 | 1.48 |
| $IC_{50}$ [nM] | 17 | 8 | 6 | 2 | 7 | 59 | 15 | 20 | 10 | 73 | 3 | 4 |
| Example | 1.49 | 1.50 | 1.51 | 1.52 | 1.53 | 1.54 | 1.55 | 1.56 | 1.57 | 1.58 | 1.59 | 1.60 |
| $IC_{50}$ [nM] | 6 | 5 | 23 | 2 | 7 | 4 | 2 | 24 | 5 | 7 | 227 | 165 |
| Example | 1.61 | 1.62 | 1.63 | 1.64 | 1.65 | 1.66 | 1.67 | 1.68 | | | | |
| $IC_{50}$ [nM] | 47 | 87 | 6 | 17 | 4 | 261 | 8 | 11 | | | | |
| Example | 2.1 | 2.2 | 2.3 | 2.4 | 2.5 | | | | | | | |
| $IC_{50}$ [nM] | 12 | 6 | 3 | 35 | 6 | | | | | | | |
| Example | 3.1 | 3.2 | 3.3 | 3.4 | 3.5 | 3.6 | 3.7 | 3.8 | 3.9 | 3.10 | 3.11 | 3.12 |
| $IC_{50}$ [nM] | 29 | 10 | 24 | 7 | 7 | 1 | 22 | 19 | 20 | 23 | 6 | 5 |
| Example | 3.13 | 3.14 | 3.15 | 3.16 | 3.17 | 3.18 | 3.19 | 3.20 | 3.21 | 3.22 | 3.23 | 3.24 |
| $IC_{50}$ [nM] | 57 | 6 | 2 | 18 | 3 | 5 | 8 | 1 | 12 | 2 | 13 | 25 |
| Example | 3.25 | 3.26 | 3.27 | 3.28 | 3.29 | 3.30 | 3.31 | 3.32 | 3.33 | 3.34 | 3.35 | 3.36 |
| $IC_{50}$ [nM] | 93 | 8 | 1 | 6 | 12 | 1 | 49 | 25 | 3 | 178 | 4 | 4 |
| Example | 3.37 | 3.38 | 3.39 | 3.40 | 3.41 | 3.42 | 3.43 | 3.44 | 4.1 | 4.2 | | |
| $IC_{50}$ [nM] | 9 | 1 | 61 | 1 | 44 | 10 | 15 | 16 | 9 | 4 | | |
| Example | 5.1 | 5.2 | 5.3 | 5.4 | 5.5 | 5.6 | 5.7 | 5.8 | 5.9 | 5.10 | 5.11 | 5.12 |
| $IC_{50}$ [nM] | 42 | 14 | 2 | 3 | 109 | 3 | 45 | 52 | 10 | 31 | 7 | 62 |
| Example | 6.1 | | 7.1 | | 8.1 | 8.2 | 8.3 | 8.4 | 8.5 | 8.6 | 8.7 | 8.8 |
| $IC_{50}$ [nM] | 6 | | 477 | | 136 | 45 | 23 | 210 | 151 | 53 | 243 | 86 |

| Example | 8.9 | 8.10 | 8.11 | 8.12 | 8.13 | 8.14 | 8.15 | 8.16 | 8.17 | 9.1 | 10.1 |
|---|---|---|---|---|---|---|---|---|---|---|---|
| $IC_{50}$ [nM] | 74 | 24 | 50 | 39 | 44 | 30 | 37 | 31 | 103 | 7 | 3 |

10. INDICATIONS

As has been found, the compounds of formula (I) are characterised by their wide range of applications in the therapeutic field. Particular mention should be made of those applications for which the compounds according to the invention of formula (I) are preferably suited on account of their pharmaceutical efficacy as ENaC inhibitors. Examples include respiratory diseases or complaints, or allergic diseases of the airways.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Particularly preferably the present invention relates to the use of compounds of formula (I) for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, COPD, chronic bronchitis, chronic sinusitis and asthma.

It is most preferable to use the compounds of formula (I) for the treatment of inflammatory and obstructive diseases such as COPD, chronic bronchitis, chronic sinusitis, asthma, cystic fibrosis, particularly COPD, chronic bronchitis, asthma and cystic fibrosis.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

11. COMBINATIONS

The compounds of formula (I) may be used on their own or in conjunction with other active substances of (I) according to the invention. If desired the compounds of formula (I) may also be used in combination with other pharmacologically active substances.

Therefore the invention further relates to medicament combinations which preferably contain, besides one or more compounds of formula (I), as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators, or double or triple combinations thereof.

Examples of preferred betamimetics which may be mentioned include Albuterole, Arformoterole, Bambuterole, Bitolterole, Broxaterole, Carbuterole, Clenbuterole, Fenoterole, Formoterole, Hexoprenaline, Ibuterole, Isoetharine, Isoprenaline, Levosalbutamole, Mabuterole, Meluadrine, Metaproterenole, Milveterol, Orciprenaline, Pirbuterole, Procaterole, Reproterole, Rimiterole, Ritodrine, Salmefamole, Salmeterole, Soterenole, Sulphonterole, Terbutaline, Tiaramide, Tolubuterole, Zinterole, Nolomirole, and
1-(2-chloro-4-hydroxyphenyl)-t-butylaminoethanole,
(−)-2-[7(S)-[2(R)-Hydroxy-2-(4-hydroxyphenyl)-ethylamino]-5,6,7,8-tetrahydro-2-naphthyloxy]-N,N-dimethylacetamide hydrochloride monohydrate,
3-(4-{6-[2-Hydroxy-2-(4-hydroxy-3-hydroxymethyl-phenyl)-ethylamino]-hexyloxy}-butyl)benzyl-sulfonamide
5-[2-(5,6-Diethyl-indan-2-ylamino)-1-hydroxy-ethyl]-8-hydroxy-1H-quinoline-2-one
4-Hydroxy-7-[2-{[2-{[3-(2-phenylethoxy)propyl] sulphonyl}ethyl]-amino}ethyl]-2(3H)-benzothiazolone
1-(2-Fluoro-4-hydroxyphenyl)-2-[4-(1-benzimidazolyl)-2-methyl-2-butylamino]ethanole
1-[3-(4-Methoxybenzyl-amino)-4-hydroxyphenyl]-2-[4-(1-benzimidazolyl)-2-methyl-2-butylamino]ethanole
1-[2H-5-hydroxy-3-oxo-4H-1,4-benzoxazin-8-yl]-2-[3-(4-N,N-dimethylaminophenyl)-2-methyl-2-propylamino] ethanole
1-[2H-5-hydroxy-3-oxo-4H-1,4-benzoxazin-8-yl]-2-[3-(4-methoxyphenyl)-2-methyl-2-propylamino]ethanole
1-[2H-5-hydroxy-3-oxo-4H-1,4-benzoxazin-8-yl]-2-[3-(4-n-butyloxyphenyl)-2-methyl-2-propylamino]ethanole
1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanole
5-Hydroxy-8-(1-hydroxy-2-isopropylaminobutyl)-2H-1,4-benzoxazin-3-(4H)-one
1-(4-Amino-3-chloro-5-trifluormethylphenyl)-2-tert.-butylamino)ethanole
6-Hydroxy-8-{1-hydroxy-2-[2-(4-methoxy-phenyl)-1,1-dimethyl-ethylamino]-ethyl}-4H-benzo[1,4]oxazin-3-one
6-Hydroxy-8-{1-hydroxy-2-[2-(4-phenoxy-acetic acid ethylester)-1,1-dimethyl-ethylamino]-ethyl}-4H-benzo[1,4] oxazin-3-one
6-Hydroxy-8-{1-hydroxy-2-[2-(4-phenoxy-acetic acid)-1,1-dimethyl-ethylamino]-ethyl}-4H-benzo[1,4]oxazin-3-one
8-{2-[1,1-Dimethyl-2-(2,4,6-trimethylphenyl)-ethylamino]-1-hydroxy-ethyl}-6-hydroxy-4H-benzo[1,4]oxazin-3-one
6-Hydroxy-8-{1-hydroxy-2-[2-(4-hydroxy-phenyl)-1,1-dimethyl-ethylamino]-ethyl}-4H-benzo[1,4]oxazin-3-one
6-Hydroxy-8-{1-hydroxy-2-[2-(4-isopropyl-phenyl)-1,1-dimethyl-ethylamino]-ethyl}-4H-benzo[1,4]oxazin-3-one
8-{2-[2-(4-Ethyl-phenyl)-1,1-dimethyl-ethylamino]-1-hydroxy-ethyl}-6-hydroxy-4H-benzo[1,4]oxazin-3-one
8-{2-[2-(4-Ethoxy-phenyl)-1,1-dimethyl-ethylamino]-1-hydroxy-ethyl}-6-hydroxy-4H-benzo[1,4]oxazin-3-one
4-(4-{2-[2-Hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-Difluor-phenyl)-1,1-dimethyl-ethylamino]-1-hydroxy-ethyl}-6-hydroxy-4H-benzo[1,4]oxazin-3-one 1-(4-Ethoxy-carbonylamino-3-cyano-5-fluorophenyl)-2-(tert.-butylamino)ethanole N-[2-Hydroxy-5-(1-hydroxy-2-{2-[4-(2-hydroxy-2-phenyl-ethylamino)-phenyl]-ethylamino}-ethyl)-phenyl]formamide 8-Hydroxy-5-(1-hydroxy-2-{2-[4-(6-methoxy-biphenyl-3-ylamino)-phenyl]-ethylamino}-ethyl)-1H-quinolin-2-one 8-Hydroxy-5-[1-hydroxy-2-(6-phenethylamino-hexylamino)-ethyl]-1H-quinolin-2-one 5-[2-(2-{4-[4-(2-Amino-2-methyl-propoxy)-phenylamino]-phenyl}-ethylamino)-1-hydroxyethyl]-8-hydroxy-1H-quinolin-2-one

[3-(4-{6-[2-Hydroxy-2-(4-hydroxy-3-hydroxymethyl-phenyl)-ethylamino]-hexyloxy}-butyl)-5-methyl-phenyl]-urea 4-(2-{6-[2-(2,6-Dichloro-benzyloxy)-ethoxy]-hexylamino}-1-hydroxy-ethyl)-2-hydroxymethyl-phenole 3-(4-{6-[2-Hydroxy-2-(4-hydroxy-3-hydroxymethyl-phenyl)-ethylamino]-hexyloxy}-butyl)-benzenesulfonamide 3-(3-{7-[2-Hydroxy-2-(4-hydroxy-3-hydroxymethyl-phenyl)-ethylamino]-heptyloxy}-propyl)-benzenesulfonamide 4-(2-{6-[4-(3-Cyclopentanesulfonyl-phenyl)-butoxy]-hexylamino}-1-hydroxy-ethyl)-2-hydroxymethyl-phenole N-Adamantan-2-yl-2-(3-{2-[2-hydroxy-2-(4-hydroxy-3-hydroxymethyl-phenyl)-ethylamino]-propyl}-phenyl)-acetamide (R,S)-4-(2-{[6-(2,2-Difluoro-4-phenylbutoxy)hexyl]amino}-1-hydroxy-ethyl)-2-(hydroxymethyl)phenole (R,S)-4-(2-{[6-(2,2-Difluoro-2-phenylethoxy)hexyl]amino}-1-hydroxy-ethyl)-2-(hydroxymethyl)phenole (R,S)-4-(2-{[4,4-Difluoro-6-(4-phenylbutoxy)hexyl]amino}-1-hydroxy-ethyl)-2-(hydroxy-methyl)phenole (R,S)-4-(2-{[6-(4,4-Difluoro-4-phenylbutoxy)hexyl]amino}-1-hydroxy-ethyl)-2-(hydroxymethyl)phenole (R,S)-5-(2-{[6-(2,2-Difluoro-2-phenylethoxy)hexyl]amino}-1-hydroxy-ethyl)-8-hydroxyquinolin-2(1H)-one (R,S)-[4-[2-({6-[2,2-Difluoro-2-(3-methylphenyl)ethoxy]hexyl}amino)-1-hydroxyethyl]-2-(hydroxymethyl)phenole 4-(1R)-2-{[6-(2,2-Difluoro-2-phenylethoxy)hexyl]amino}-1-hydroxyethyl)-2-(hydroxymethyl)phenol (R,S)-2-(Hydroxymethyl)-4-(1-hydroxy-2-{[4,4,5I5-tetrafluoro-6-(3-phenylpropoxy)-hexyl]amino}ethyl)phenole (R,S)-[5-(2-{[6-(2,2-Difluoro-2-phenylethoxy)hexyl]amino}-1-hydroxy-ethyl)-2-hydroxy-phenyl]formamide (R,S)-4-[2-({6-[2-(3-Bromophenyl)-2,2-difluoroethoxy]hexyl}amino)-1-hydroxyethyl]-2-(hydroxymethyl)phenole (R,S)—N-[3-(1,1-Difluoro-2-{[6-({2-hydroxy-2-[4-hydroxy-3-(hydroxymethyl)phenyl]-ethyl}amino)hexyl]oxy}ethyl)phenyl]urea 3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidine-2,4-dione (R,S)-4-[2-({6-[2,2-difluoro-2-(3-methoxyphenyl)ethoxy]hexyl}amino)-1-hydroxyethyl]-2-(hydroxymethyl)phenole 5-((1R)-2-{[6-(2,2-difluoro-2-phenylethoxy)hexyl]amino}-1-hydroxyethyl)-8-hydroxyquinolin-2(1H)-one 4-((1R)-2-{[4,4-Difluoro-6-(4-phenylbutoxy)hexyl]amino}-1-hydroxyethyl)-2-(hydroxymethyl)phenole (R,S)-4-(2-{[6-(3,3-Difluoro-3-phenylpropoxy)hexyl]amino}-1-hydroxy-ethyl)-2-(hydroxymethyl)phenole (R,S)-(2-{[6-(2,2-Difluoro-2-phenylethoxy)-4,4-difluorohexyl]amino}-1-hydroxyethyl)-2-(hydroxymethyl)phenole (R,S)-4-(2-{[6-(2,2-difluoro-3-phenylpropoxy)hexyl]amino}-1-hydroxy ethyl)-2-(hydroxymethyl)phenole 3-[2-(3-Chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide 7-[2-(2-{3-[2-(2-Chloro-phenyl)-ethylamino]-propylsulfanyl}-ethylamino)-1-hydroxy-ethyl]-4-hydroxy-3H-benzothiazol-2-one and 7-[(1R)-2-(2-{3-[2-(2-Chloro-phenyl)-ethylamino]-propylsulfanyl}-ethylamino)-1-hydroxy-ethyl]-4-hydroxy-3H-benzothiazol-2-one optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred anticholinergics which may be mentioned include Tiotropium salts, preferred the bromide salt, Oxitropium salts, preferred the bromide salt, Flutropium salts, preferred the bromide salt, Ipratropium salts, preferred the bromide salt, Aclidinium salts, preferred the bromide salt, Glycopyrronium salts, preferred the bromide salt, Trospium salts, preferred the chloride salt, Tolterodin. From the above mentioned salts the pharmacologically active part is the cation, possible anions are chloride, bromide, iodide, sulfate, phosphate, methansulfonate, nitrate, maleate, acetate, citrate, fumarate, tartrate, oxalate, succinate, benzoate or p-toluenesulfonate. Further examples of preferred anticholinergics are selected from among 2,2-Diphenylpropionic acid tropenole ester-methobromide 2,2-Diphenylpropionic acid scopine ester-methobromide 2-Fluor-2,2-Diphenylacetic acid scopine ester-methobromide 2-Fluor-2,2-Diphenylacetic acid tropenole ester-methobromide 3,3',4,4'-Tetrafluorbenzil acid tropenole ester-methobromide 3,3',4,4'-Tetrafluorbenzil acid scopine ester-methobromide 4,4'-Difluorbenzil acid tropenole ester-methobromide 4,4'-Difluorbenzil acid scopine ester-methobromide 3,3'-Difluorbenzil acid tropenole ester-methobromide 3,3'-Difluorbenzil acid scopine ester-methobromide 9-Hydroxy-fluorene-9-carbon acid tropenole ester-methobromide 9-Fluor-fluorene-9-carbon acid tropenole ester-methobromide 9-Hydroxy-fluorene-9-carbon acid scopine ester-methobromide 9-Fluor-fluorene-9-carbon acid scopine ester methobromide 9-Methyl-fluorene-9-carbon acid tropenole estermethobromide 9-Methyl-fluorene-9-carbon acid scopine estermethobromide Benzil acid cyclopropyl tropine ester-methobromide 2,2-Diphenylpropionic acid cyclopropyl tropine ester-methobromide 9-Hydroxy-xanthene-9-carbon acid cyclopropyl tropine ester-methobromide 9-Methyl-fluorene-9-carbon acid cyclopropyl tropine ester-methobromide 9-Methyl-xanthene-9-carbon acid cyclopropyl tropine ester-methobromide 9-Hydroxy-fluorene-9-carbon acid cyclopropyl tropine ester-methobromide 4,4'-Difluorbenzil acid methylester cyclopropyl tropine ester-methobromide 9-Hydroxy-xanthene-9-carbon acid tropenole ester-methobromide 9-Hydroxy-xanthene-9-carbon acid scopine ester methobromide 9-Methyl-xanthene-9-carbon acid tropenole ester-methobromide 9-Methyl-xanthene-9-carbon acid scopine estermethobromide 9-Ethyl-xanthene-9-carbon acid tropenole ester methobromide 9-Difluoromethyl-xanthene-9-carbon acid tropenole ester-methobromide 9-Hydroxymethyl-xanthene-9-carbon acid scopine ester methobromide.

Examples of preferred corticosteroids which may be mentioned include Beclomethasone, Betamethasone, Budesonide, Butixocorte, Ciclesonide, Deflazacorte, Dexamethasone, Etiprednole, Flunisolide, Fluticasone, Loteprednole, Mometasone, Prednisolone, Prednisone, Rofleponide, Triamcinolone, Tipredane, and {20R-16alpha,17alpha-[butylidenebis(oxy)]-6alpha,9alpha-difluoro-11beta-hydroxy-17beta-(methylthio)androsta-4-en-3-one}, 9-fluoro-11beta,17,21-trihydroxy-16alpha-methylpregna-1,4-diene-3,20-dione 21-cyclohexanecarboxylate 17-cyclopropanecarboxylate, 16,17-butylidene dioxy-6,9-difluoro-11-hydroxy-17-(methylthio)androst-4-en-3-one Flunisolide-21-[4'-(nitrooxymethyl)benzoate]

6,9-Difluoro-17-[(2-furanylcarbonyl)oxy]-11-hydroxy-16-methyl-3-oxo-androsta-1,4-dien-17-carbothion acid (S)-fluoromethylester, 6,9-Difluoro-11-hydroxy-16-methyl-3-oxo-17-propionyloxy-androsta-1,4-dien-17-carbothion acid (S)-(2-oxo-tetrahydro-furan-3S-yl)ester, and 6alpha,9alpha-difluoro-11beta-hydroxy-16alpha-methyl-3-oxo-17alpha-(2,2,3,3-tertamethylcyclopropylcarbonyl)oxy-androsta-1,4-diene-17beta-carboxylic acid cyanomethyl ester optionally in racemic form, as enantiomers, diastereomeres or as pharmacologically acceptable salts, solvates or hydrates. Examples for preferred salts and derivatives are alkali salts, i.e. sodium or potassium salts, sulfobenzoates, phosphates, isonicotinates, acetates, dichloroacetates, propionates, dihydrogenphosphates, palmitates, pivalates or furoates.

Examples of preferred PDE4-inhibitors which may be mentioned include Enprofylline, Theophylline, Roflumilaste, Ariflo (Cilomilaste), Tofimilaste, Pumafentrine, Lirimilaste, Apremilaste, Arofylline, Atizorame, Oglemilastum, Tetomilaste and 5-[(N-(2,5-dichloro-3-pyridinyl)-carboxamide]-8-methoxyquinoline 5-[N-(3,5-dichloro-1-oxido-4-pyridinyl)-carboxamide]-8-methoxy-2-(trifluoromethyl)-quinoline N-(3,5-dichloropyrid-4-yl)-[1-(4-fluorobenzyl)-5-hydroxyindole-3-yl]glyoxyl acid amide), 9-[(2-fluorophenyl)methyl]-N-methyl-2-(trifluoromethyl)-9H-purine-6-amine 4-[(2R)-2-[3-(cyclopentyloxy)-4-methoxyphenyl]-2-phenylethyl]-pyridine, N-[(3R)-3,4,6,7-tetrahydro-9-methyl-4-oxo-1-phenylpyrrolo[3,2,1-jk][1,4]benzodiazepin-3-yl]-4-Pyridinecarboxamide, 4-[6,7-diethoxy-2,3-bis(hydroxymethyl)-1-naphthalenyl]-1-(2-methoxyethyl)-2(1H)-pyridinone, 2-[4-[6,7-diethoxy-2,3-bis(hydroxymethyl)-1-naphthalenyl]-2-pyridinyl]-4-(3-pyridinyl)-1(2H)-Phthalazinone, (3-(3-cyclopenyloxy-4-methoxybenzyl)-6-ethylamino-8-isopropyl-3H-purine, beta-[3-(cyclopentyloxy)-4-methoxyphenyl]-1,3-dihydro-1,3-dioxo-2H-isoindole-2-propanamide, 9-ethyl-2-methoxy-7-methyl-5-propyl-imidazo[1,5-a]pyrido[3,2-e]pyrazin-6(5H)-one 5-[3-(cyclopentyloxy)-4-methoxyphenyl]-3-[(3-methylphenyl)methyl] (3S,5S)-2-piperidinone, 4-[1-[3,4-bis(difluoromethoxy)phenyl]-2-(3-methyl-1-oxido-4-pyridinyl)ethyl]-alpha,alpha-bis(trifluoromethyl)-Benzenemethanol N-(3,5-Dichloro-1-oxo-pyridine-4-yl)-4-difluoromethoxy-3-cyclopropylmethoxybenzamide (−)p-[(4aR*,10bS*)-9-Ethoxy-1,2,3,4,4a,10b-hexahydro-8-methoxy-2-methylbenzo[s][1,6]naphthyridin-6-yl]-N,N-diisopropylbenzamide (R)-(+)-1-(4-Bromobenzyl)-4-[(3-cyclopentyloxy)-4-methoxyphenyl]-2-pyrrolidone 3-(Cyclopentyloxy-4-methoxyphenyl)-1-(4-N'-[N-2-cyano-S-methyl-isothioureido]benzyl)-2-pyrrolidone cis[4-Cyano-4-(3-cyclopentyloxy-4-methoxyphenyl)cyclohexan-1-carbon acid]

2-carbomethoxy-4-cyano-4-(3-cyclopropylmethoxy-4-difluoromethoxyphenyl)cyclohexan-1-one cis[4-Cyano-4-(3-cyclopropylmethoxy-4-difluoromethoxyphenyl)cyclohexan-1-ol]

(R)-(+)-Ethyl[4-(3-cyclopentyloxy-4-methoxyphenyl)pyrrolidine-2-yliden]acetate (S)-(−)-Ethyl[4-(3-cyclopentyloxy-4-methoxyphenyl)pyrrolidine-2-yliden]acetate 9-Cyclopentyl-5,6-dihydro-7-ethyl-3-(2-thienyl)-9H-pyrazolo[3,4-c]-1,2,4-triazolo[4,3-a]pyridine 9-Cyclopentyl-5,6-dihydro-7-ethyl-3-(tert-butyl)-9H-pyrazolo[3,4-c]-1,2,4-triazolo[4,3-a]pyridine optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred LTD4-antagonists which may be mentioned include Montelukast, Pranlukast, Zafirlukast, Masikulast, L-733321 (see compound 2ab of D. Guay et al, Bioorg. Med. Chem. Lett. 8 (1998) 453-458) and (E)-8-[2-[4-[4-(4-Fluorophenyl)butoxy]phenyl]ethenyl]-2-(1H-tetrazole-5-yl)-4H-1-benzopyran-4-one (MEN-91507)

4-[6-Acetyl-3-[3-(4-acetyl-3-hydroxy-2-propylphenylthio)propoxy]-2-propylphenoxy]-butyric acid (MN-001)

1-(((R)-(3-(2-(6,7-Difluoro-2-quinolinyl)ethenyl)phenyl)-3-(2-(2-hydroxy-2-propyl)phenyl)thio)methylcyclopropane-acetic acid, 1-(((1R)-3(3-(2-(2,3-Dichlorothieno[3,2-b]pyridin-5-yl)-(E)-ethenyl)phenyl)-3-(2-(1-hydroxy-1-methylethyl)phenyl)propyl)thio)methyl)cyclopropane acetic acid

[2-[[2-(4-tert-Butyl-2-thiazolyl)-5-benzofuranyl]oxymethyl]phenyl]acetic acid optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate. Further examples for optionally preferred salts and derivatives are alkali salts, i.e. sodium or potassium salts, sulfobenzoates, phosphates, isonicotinates, acetates, propionates, dihydrogenphosphates, palmitates, pivalates or furoates.

Examples of preferred EGFR-inhibitors which may be mentioned include Cetuximab, Trastuzumab, Panitumumab Gefitinib, Canertinib, Erlotinib, Mab ICR-62 and 4-[(3-Chlor-4-fluorphenyl)amino]-6-{[4-(morpholine-4-yl)-1-oxo-2-butene-1-yl]amino}-7-cyclopropylmethoxy-quinazoline 4-[(3-Chlor-4-fluorphenyl)amino]-6-{[4-(N,N-diethylamino)-1-oxo-2-butene-1-yl]amino}-7-cyclopropyl-methoxy-quinazoline 4-[(3-Chlor-4-fluorphenyl)amino]-6-{[4-(N,N-dimethylamino)-1-oxo-2-butene-1-yl]amino}-7-cyclopropyl-methoxy-quinazoline 4-[(R)-(1-Phenyl-ethyl)amino]-6-{[4-(morpholine-4-yl)-1-oxo-2-butene-1-yl]amino}-7-cyclopentyloxy-quinazoline 4-[(3-Chlor-4-fluor-phenyl)amino]-6-{[4-((R)-6-methyl-2-oxo-morpholine-4-yl)-1-oxo-2-butene-1-yl]amino}-7-cyclopropylmethoxy-quinazoline 4-[(3-Chlor-4-fluor-phenyl)amino]-6-{[4-((R)-6-methyl-2-oxo-morpholine-4-yl)-1-oxo-2-butene-1-yl]amino}-7-[(S)-(tetrahydrofuran-3-yl)oxy]-quinazoline 4-[(3-Chlor-4-fluor-phenyl)amino]-6-{[4-((R)-2-methoxymethyl-6-oxo-morpholine-4-yl)-1-oxo-2-butene-1-yl]amino}-7-cyclopropylmethoxy-quinazoline 4-[(3-Chlor-4-fluor-phenyl)amino]-6-[2-((S)-6-methyl-2-oxo-morpholine-4-yl)-ethoxy]-7-methoxy-quinazoline 4-[(3-Chlor-4-fluorphenyl)amino]-6-({4-[N-(2-methoxy-ethyl)-N-methyl-amino]-1-oxo-2-butene-1-yl}amino)-7-cyclopropylmethoxy-quinazoline 4-[(3-Chlor-4-fluorphenyl)amino]-6-{[4-(N,N-dimethylamino)-1-oxo-2-butene-1-yl]amino}-7-cyclopentyloxy-quinazoline 4-[(R)-(1-Phenyl-ethyl)amino]-6-{[4-(N,N-bis-(2-methoxy-ethyl)-amino)-1-oxo-2-butene-1-yl]amino}-7-cyclopropylmethoxy-quinazoline 4-[(R)-(1-Phenyl-ethyl)amino]-6-({4-[N-(2-methoxy-ethyl)-N-ethyl-amino]-1-oxo-2-butene-1-yl}amino)-7-cyclopropylmethoxy-quinazoline 4-[(R)-(1-Phenyl-ethyl)amino]-6-({4-[N-(2-methoxy-ethyl)-N-methyl-amino]-1-oxo-2-butene-1-yl}amino)-7-cyclopropylmethoxy-quinazoline 4-[(R)-(1-Phenyl-ethyl)amino]-6-({4-[N-(tetrahydropyran-4-yl)-N-methyl-amino]-1-oxo-2-butene-1-yl}amino)-7-cyclopropylmethoxy-quinazoline 4-[(3-Chlor-4-fluorphenyl)amino]-6-{[4-(N,N-dimethylamino)-1-oxo-2-butene-1-yl]amino}-7-((R)-tetrahydrofuran-3-yloxy)-quinazoline 4-[(3-Chlor-4-fluorphenyl)amino]-6-{[4-(N,N-dimethylamino)-1-oxo-2-butene-1-yl]amino}-7-((S)-tetrahydrofuran-3-yloxy)-quinazoline 4-[(3-Chlor-4-fluorphenyl)amino]-6-({4-[N-(2-methoxy-ethyl)-N-methyl-amino]-1-oxo-2-butene-1-yl}amino)-7-cyclopentyloxy-quinazoline 4-[(3-Chlor-4-fluorphenyl)amino]-6-{[4-(N-cyclopropyl-N-methyl-amino)-1-oxo-2-butene-1-yl]amino}-7-cyclopentyloxy-quinazoline 4-[(3-Chlor-4-fluorphenyl)amino]-6-{[4-(N,N-dimethylamino)-1-oxo-2-butene-1-yl]amino}-7-[(R)-(tetrahydrofuran-2-yl)methoxy]-quinazoline 4-[(3-Chlor-4-fluorphenyl)amino]-6-{[4-(N,N-dimethylamino)-1-oxo-2-butene-1-yl]amino}-7-[(S)-(tetrahydrofuran-2-yl)methoxy]-quinazoline 4-[(3-Ethinyl-phenyl)amino]-6,7-bis-(2-methoxy-ethoxy)-quinazoline 4-[(3-Chlor-4-fluorphenyl)amino]-7-[3-(morpholine-4-yl)-propyloxy]-6-[(vinylcarbonyl)amino]-quinazoline 4-[(R)-(1-Phenyl-ethyl)amino]-6-(4-hydroxy-phenyl)-7H-pyrrolo[2,3-d]pyrimidine 3-Cyano-4-[(3-chlor-4-fluorphenyl)amino]-6-{[4-(N,N-dimethylamino)-1-oxo-2-butene-1-yl]amino}-7-ethoxy-quinoline 4-{[3-Chlor-4-(3-fluor-benzyloxy)-phenyl]amino}-6-(5-{[(2-methansulfonylethyl)amino]methyl}-furan-2-yl)quinazoline 4-[(R)-(1-Phenyl-ethyl)amino]-6-{[4-((R)-6-methyl-2-oxo-morpholine-4-yl)-1-oxo-2-butene-1-yl]amino}-7-methoxy-quinazoline 4-[(3-Chlor-4-fluorphenyl)amino]-6-{[4-(morpholine-4-yl)-1-oxo-2-butene-1-yl]amino}-7-[(tetrahydrofuran-2-yl)methoxy]-quinazoline 4-[(3-Chlor-4-fluorphenyl)amino]-6-({4-[N,N-bis-(2-methoxy-ethyl)-amino]-1-oxo-2-butene-1-yl}amino)-7-[(tetrahydrofuran-2-yl)methoxy]-quinazoline 4-[(3-Ethinyl-phenyl)amino]-6-{[4-(5,5-dimethyl-2-oxo-morpholine-4-yl)-1-oxo-2-butene-1-yl]amino}-quinazoline 4-[(3-Chlor-4-fluor-phenyl)amino]-6-[2-(2,2-dimethyl-6-oxo-morpholine-4-yl)-ethoxy]-7-methoxy-quinazoline 4-[(3-Chlor-4-fluor-phenyl)amino]-6-[2-(2,2-dimethyl-6-oxo-morpholine-4-yl)-ethoxy]-7-[(R)-(tetrahydrofuran-2-yl)methoxy]-quinazoline 4-[(3-Chlor-4-fluor-phenyl)amino]-7-[2-(2,2-dimethyl-6-oxo-morpholine-4-yl)-ethoxy]-6-[(S)-(tetrahydrofuran-2-yl)methoxy]-quinazoline 4-[(3-Chlor-4-fluor-phenyl)amino]-6-{2-[4-(2-oxo-morpholine-4-yl)-piperidin-1-yl]-ethoxy}-7-methoxy-quinazoline 4-[(3-Chlor-4-fluor-phenyl)amino]-6-[1-(tert.-butyloxycarbonyl)-piperidine-4-yloxy]-7-methoxy-quinazoline 4-[(3-Chlor-4-fluor-phenyl)amino]-6-(trans-4-amino-cyclohexane-1-yloxy)-7-methoxyquinazoline 4-[(3-Chlor-4-fluor-phenyl)amino]-6-(trans-4-methansulfonylamino-cyclohexane-1-yloxy)-7-methoxy-quinazoline 4-[(3-Chlor-4-fluor-phenyl)amino]-6-(tetrahydropyran-3-yloxy)-7-methoxy-quinazoline 4-[(3-Chlor-4-fluor-phenyl)amino]-6-(1-methyl-piperidine-4-yloxy)-7-methoxy-quinazoline 4-[(3-Chlor-4-fluor-phenyl)amino]-6-{1-[(morpholine-4-yl)carbonyl]-piperidine-4-yloxy}-7-methoxy-quinazoline 4-[(3-Chlor-4-fluor-phenyl)amino]-6-{1-[(methoxymethyl)carbonyl]-piperidine-4-yloxy}-7-methoxy-quinazoline 4-[(3-Chlor-4-fluor-phenyl)amino]-6-(piperidine-3-yloxy)-7-methoxy-quinazoline 4-[(3-Chlor-4-fluor-phenyl)amino]-6-[1-(2-acetylamino-ethyl)-piperidine-4-yloxy]-7-methoxy-quinazoline 4-[(3-Chlor-4-fluor-phenyl)amino]-6-(tetrahydropyran-4-yloxy)-7-ethoxy-quinazoline 4-[(3-Chlor-4-fluor-phenyl)amino]-6-((S)-tetrahydrofuran-3-yloxy)-7-hydroxy-quinazoline 4-[(3-Chlor-4-fluor-phenyl)amino]-6-(tetrahydropyran-4-yloxy)-7-(2-methoxy-ethoxy)-quinazoline 4-[(3-Chlor-4-fluor-phenyl)amino]-6-{trans-4-[(dimethylamino)sulfonylamino]cyclohexane-1-yloxy}-7-methoxy-quinazoline 4-[(3-Chlor-4-fluor-phenyl)amino]-6-{trans-4-[(morpholine-4-yl)carbonylamino]-cyclohexane-1-yloxy}-7-methoxy-quinazoline 4-[(3-Chlor-4-fluor-phenyl)amino]-6-{trans-4-[(morpholine-4-yl)sulfonylamino]-cyclohexane-1-yloxy}-7-methoxy-quinazoline 4-[(3-Chlor-4-fluor-phenyl)amino]-6-(tetrahydropyran-4-yloxy)-7-(2-acetylamino-ethoxy)-quinazoline 4-[(3-Chlor-4-fluor-phenyl)amino]-6-(tetrahydropyran-4-yloxy)-7-(2-methansulfonylamino-ethoxy)-quinazoline 4-[(3-Chlor-4-fluor-phenyl)amino]-6-{1-[(piperidine-1-yl)carbonyl]-piperidine-4-yloxy}-7-methoxy-quinazoline 4-[(3-Chlor-4-fluor-phenyl)amino]-6-(1-aminocarbonylmethyl-piperidine-4-yloxy)-7-methoxy-quinazoline 4-[(3-Chlor-4-fluor-phenyl)amino]-6-(cis-4-{N-[(tetrahydropyran-4-yl)carbonyl]-N-methyl-amino}-cyclohexane-1-yloxy)-7-methoxy quinazoline 4-[(3-Chlor-4-fluor-phenyl)amino]-6-(cis-4-{N-[(morpholine-4-yl)carbonyl]-N-methyl-amino}-cyclohexane-1-yloxy)-7-methoxy-quinazoline 4-[(3-Chlor-4-fluor-phenyl)amino]-6-(cis-4-{N-[(morpholine-4-yl)sulfonyl]-N-methyl-amino}-cyclohexane-1-yloxy)-7-methoxy-quinazoline 4-[(3-Chlor-4-fluor-phenyl)amino]-6-(trans-4-ethansulfonylamino-cyclohexane-1-yloxy)-7-methoxy-quinazoline 4-[(3-Chlor-4-fluor-phenyl)amino]-6-(1-methansulfonyl-piperidine-4-yloxy)-7-ethoxy-quinazoline 4-[(3-Chlor-4-fluor-phenyl)amino]-6-(1-methansulfonyl-piperidine-4-yloxy)-7-(2-methoxy-ethoxy)-quinazoline 4-[(3-Chlor-4-fluor-phenyl)amino]-6-[1-(2-methoxy-acetyl)-piperidine-4-yloxy]-7-(2-methoxy-ethoxy)-quinazoline 4-[(3-Chlor-4-fluor-phenyl)amino]-6-(cis-4-acetylamino-cyclohexane-1-yloxy)-7-methoxy-quinazoline 4-[(3-Ethinyl-phenyl)amino]-6-[1-(tert-butyloxycarbonyl)-piperidine-4-yloxy]-7-methoxy-quinazoline 4-[(3-Ethinyl-phenyl)amino]-6-(tetrahydropyran-4-yloxy]-7-methoxy-quinazoline 4-[(3-Chlor-4-fluor-phenyl)amino]-6-(cis-4-{N-[(piperidine-1-yl)carbonyl]-N-methyl-amino}-cyclohexane-1-yloxy)-7-methoxy-quinazoline 4-[(3-Chlor-4-fluor-phenyl)amino]-6-(cis-4-{N-[(4-methyl-piperazine-1-yl)carbonyl]-N-methyl-amino}-cyclohexane-1-yloxy)-7-methoxy-quinazoline 4-[(3-Chlor-4-fluor-phenyl)amino]-6-{cis-4-[(morpholine-4-yl)carbonylamino]-cyclohexane-1-yloxy}-7-methoxy-quinazoline 4-[(3-Chlor-4-fluor-phenyl)amino]-6-{1-[2-(2-oxopyrrolidine-1-yl)ethyl]-piperidine-4-yloxy}-7-methoxy-quinazoline 4-[(3-Chlor-4-fluor-phenyl)amino]-6-{1-[(morpholine-4-yl)carbonyl]-piperidine-4-yloxy}-7-(2-methoxy-ethoxy)-quinazoline 4-[(3-Ethinyl-phenyl)amino]-6-(1-acetyl-piperidine-4-yloxy)-7-methoxy-quinazoline 4-[(3-Ethinyl-phenyl)amino]-6-(1-methyl-piperidine-4-yloxy)-7-methoxy-quinazoline 4-[(3-Ethinyl-phenyl)amino]-6-(1-methansulfonyl-piperidine-4-yloxy)-7-methoxy-quinazoline 4-[(3-Chlor-4-fluor-phenyl)amino]-6-(1-methyl-piperidine-4-yloxy)-7(2-methoxy-ethoxy)-quinazoline 4-[(3-Chlor-4-fluor-phenyl)amino]-6-(1-isopropyloxycarbonyl-piperidine-4-yloxy)-7-methoxy-quinazoline 4-[(3-Chlor-4-fluor-phenyl)amino]-6-(cis-4-methylamino-cyclohexane-1-yloxy)-7-methoxy-chinazoline 4-[(3-Chlor-4-fluor-phenyl)amino]-6-{cis-4-[N-(2-methoxy-acetyl)-N-methyl-amino]-cyclohexane-1-yloxy}-7-methoxy-quinazoline 4-[(3-Ethinyl-phenyl)amino]-6-(piperidine-4-yloxy)-7-methoxy-quinazoline 4-[(3-Ethinyl-phenyl)amino]-6-[1-(2-methoxy-acetyl)-piperidine-4-yloxy]-7-methoxy-quinazoline 4-[(3-Ethinyl-phenyl)amino]-6-{1-[(morpholine-4-yl)carbonyl]-piperidine-4-yloxy}-7-methoxy-quinazoline 4-[(3-Chlor-4-fluor-phenyl)amino]-6-{1-[(cis-2,6-dimethyl-morpholine-4-yl)carbonyl]-piperidine-4-yloxy}-7-methoxy-quinazoline 4-[(3-Chlor-4-fluor-phenyl)amino]-6-{1-[(2-methyl-morpholine-4-yl)carbonyl]-piperidine-4-yloxy}-7-methoxy-quinazoline 4-[(3-Chlor-4-fluor-phenyl)amino]-6-{1-[(S,S)-(2-oxa-5-aza-bicyclo[2.2.1]hept-5-yl)carbonyl]-piperidine-4-yloxy}-7-methoxy-quinazoline 4-[(3-Chlor-4-fluor-phenyl)amino]-6-{1-[(N-methyl-N-2-methoxyethyl-amino)carbonyl]-piperidine-4-yloxy}-7-methoxy-quinazoline 4-[(3-Chlor-4-fluor-phenyl)amino]-6-(1-ethyl-piperidine-4-yloxy)-7-methoxy-quinazoline 4-[(3-Chlor-4-fluor-phenyl)amino]-6-{1-[(2-methoxyethyl)carbonyl]-piperidine-4-yloxy}-7-methoxy-quinazoline 4-[(3-Chlor-4-fluor-phenyl)amino]-6-{1-[(3-methoxypropyl-amino)-carbonyl]-piperidine-4-yloxy}-7-methoxy-quinazoline 4-[(3-Chlor-4-fluor-phenyl)amino]-6-[cis-4-(N-methansulfonyl-N-methyl-amino)-cyclohexane-1-yloxy]-7-methoxy-quinazoline 4-[(3-Chlor-4-fluor-phenyl)amino]-6-[cis-4-(N-acetyl-N-methyl-amino)-cyclohexane-1-yloxy]-7-methoxy-quinazoline 4-[(3-Chlor-4-fluor-phenyl)amino]-6-(trans-4-methylamino-cyclohexane-1-yloxy)-7-methoxy-quinazoline 4-[(3-Chlor-4-fluor-phenyl)amino]-6-[trans-4-(N-methansulfonyl-N-methyl-amino)-cyclohexane-1-yloxy]-7-methoxy-quinazoline 4-[(3-Chlor-4-fluor-phenyl)amino]-6-(trans-4-dimethylamino-cyclohexane-1-yloxy)-7-methoxy-quinazoline 4-[(3-Chlor-4-fluor-phenyl)amino]-6-(trans-4-{N-[(morpholine-4-yl)carbonyl]-N-methyl-amino}-cyclohexane-1-yloxy)-7-methoxy-quinazoline 4-[(3-Chlor-4-fluor-phenyl)amino]-6-[2-(2,2-dimethyl-6-oxo-morpholine-4-yl)-ethoxy]-7-[(S)-(tetrahydrofuran-2-yl)methoxy]-quinazoline 4-[(3-Chlor-4-fluor-phenyl)amino]-6-(1-methansulfonyl-piperidine-4-yloxy)-7-methoxy-quinazoline 4-[(3-Chlor-4-fluor-phenyl)amino]-6-(1-cyano-piperidine-4-yloxy)-7-methoxy-quinazoline optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred dopamin antagonists which may be mentioned include Bromocriptine, Cabergoline, Alpha-Dihydroergocryptine, Lisuride, Pergolide, Pramipexole, Roxindole, Ropinirole, Talipexole, Terguride and Viozane, optionally in racemic form, as enantiomers, diastereomeres or as pharmacologically acceptable salts, solvates or hydrates.

Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred antiallergic agents which may be mentioned include Epinastine, Cetirizine, Azelastine, Fexofenadine, Levocabastine, Loratadine, Mizolastine, Ketotifene, Emedastine, Dimetindene, Clemastine, Bamipine, Cexchlorpheniramine, Pheniramine, Doxylamine, Chlorphenoxamine, Dimenhydrinate, Diphenhydramine, Promethazine, Ebastine, Olopatadine, Desloratidine and Meclozine, optionally in racemic form, as enantiomers, diastereomeres or as pharmacologically acceptable salts, solvates or hydrates.

Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred PAF antagonists which may be mentioned include Lexipafante and
4-(2-Chlorphenyl)-9-methyl-2-[3(4-morpholinyl)-3-propanone-1-yl]-6H-thieno-[3,2-f]-[1,2,4]triazolo[4,3-a][1,4]diazepine
6-(2-Chlorphenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepine
optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred MAP kinase inhibitors which may be mentioned include
Bentamapimod (AS-602801)
Doramapimod (BIRB-796),
5-Carbamoylindole (SD-169),
6-[(aminocarbonyl)(2,6-difluorophenyl)amino]-2-(2,4-difluorophenyl)-3-pyridine carboxamide (VX-702),
alpha-[2-[[2-(3-pyridinyl)ethyl]amino]-4-pyrimidinyl]-2-benzothiazole acetonitrile (AS-601245),
9,12-Epoxy-1H-diindolo[1,2,3-fg:3',2',1'-kl]pyrrolo[3,4-i][1,6]benzodiazocine-10-Carboxylic acid (CEP-1347),
4-[3-(4-chlorophenyl)-5-(1-methyl-4-piperidinyl)-1H-pyrazole-4-yl]-pyrimidine (SC-409),
optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred MRP4-Inhibitors which may be mentioned include N-Acetyl-dinitrophenyl-Cysteine, cGMP, Cholate, Diclofenac, Dehydroepiandrosterone 3-glucuronide, Dehydroepiandrosterone 3-sulphate, Dilazep, Dinitrophenyl-5-glutathione, Estradiol 17-beta-glucuronide, Estradiol 3,17-disulphate, Estradiol 3-glucuronide, Estradiol 3-sulphate, Estrone 3-sulphate, Flurbiprofen, Folate, N5-formyl-tetrahydrofolate, Glycocholate, Glycolithocholic acid sulphate, Ibuprofen, Indomethacin, Indoprofen, Ketoprofen, Lithocholic acid sulphate, Methotrexate, (E)-3-[[[3-[2-(7-Chloro-2-quinolinyl)ethenyl]phenyl]-[[3-dimethylamino)-3-oxopropyl]thio]methyl]thio]-propanoic acid alpha-Naphthyl-beta-D-glucuronide, Nitrobenzyl mercaptopurine riboside, Probenecid, Valspodar, Sildenafil, Sulfinpyrazone, Taurochenodeoxycholate, Taurocholate, Taurodeoxycholate, Taurolithocholate, Taurolithocholic acid sulphate, Topotecan, Trequinsin, Zaprinast and Dipyridamol, optionally in racemic form, as enantiomers, diastereomeres or as pharmacologically acceptable salts, solvates or hydrates.

Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred iNOS-Inhibitors which may be mentioned include S-(2-Aminoethyl)isothio-urea, Aminoguanidine, 2-Aminomethylpyridine, 5,6-dihydro-6-methyl-4H-1,3-thiazine-2-amine (AMT), L-Canavanin, 2-Iminopiperidine, S-Isopropylisothiourea, S-Methylisothiourea, S-Ethylisothiourea, S-Methylthiocitrulline, S-Ethylthiocitrulline, L-NA (Nw-Nitro-L-arginin), L-NAME (N$^\omega$-Nitro-L-argininmethylester), L-NMMA (N$^\omega$-Monomethyl-L-arginin), L-NIO (N$^\omega$-Iminoethyl-L-ornithin), L-NIL (N$^\omega$-iminoethyl-lysin), (S)-6-Acetimidoylamino-2-amino-hexanoic acid (1H-tetrazole-5-yl)-amide N-[[3-(aminomethyl)phenyl]methyl]-ethanimidamide, (S)-4-(2-acetimidoylamino-ethylsulfanyl)-2-amino-buturic acid, 2-[2-(4-Methoxy-pyridine-2-yl)-ethyl]-3H-imidazo[4,5-b]pyridine, 2-((R)-3-amino-1-phenyl-propoxy)-4-chlor-5-fluorbenzonitrile, 2-((1R,3S)-3-amino-4-hydroxy-1-thiazole-5-yl-butylsulfanyl)-6-trifluoromethyl-nicotinonitrile, 2-((1R,3S)-3-amino-4-hydroxy-1-thiazole-5-yl-butylsulfanyl)-4-chlor-benzonitrile, 2-((1R,3S)-3-amino-4-hydroxy-1-thiazole-5-yl-butylsulfanyl)-5-chlor-benzonitrile, (2S,4R)-2-amino-4-(2-chlor-5-trifluoromethyl-phenylsulfanyl)-4-thiazole-5-yl-butane-1-ol, 2-((1R,3S)-3-amino-4-hydroxy-1-thiazole-5-yl-butylsulfanyl)-5-chlor-nicotinonitrile, 4-((S)-3-amino-4-hydroxy-1-phenyl-butylsulfanyl)-6-methoxy-nicotinonitrile and substituted 3-phenyl-3,4-dihydro-1-isoquinolinamine as for instance 1S,5S,6R)-7-Chlor-5-methyl-2-aza-bicyclo[4.1.0]hept-2-ene-3-ylamin (4R,5R)-5-Ethyl-4-methyl-thiazolidine-2-ylideneamine, (1S,5S,6R)-7-Chlor-5-methyl-2-aza-bicyclo[4.1.0]hept-2-ene-3-ylamin, (4R,5R)-5-Ethyl-4-methyl-thiazolidine-2-ylideneamine, (4R,5R)-5-Ethyl-4-methyl-selenazolidine-2-ylideneamine, 4-Aminotetrahydrobiopterine, (E)-3-(4-Chlor-phenyl)-N-(1-{2-oxo-2-[4-(6-trifluormethyl-pyrimidine-4-yloxy)-piperidine-1-yl]-ethylcarbamoyl}-2-pyridine-2-yl-ethyl)-acrylamide, 3-(2,4-Difluor-phenyl)-6-[2-(4-imidazole-1-ylmethyl-phenoxy)-ethoxy]-2-phenyl-pyridine, 3-{[(Benzo[1,3]dioxol-5-ylmethyl)-carbamoyl]-methyl}-4-(2-imidazole-1-yl-pyrimidine-4-yl)-piperazine-1-carbon acid methylester, (R)-1-(2-imidazole-1-yl-6-methyl-pyrimidine-4-yl)-pyrrolidine-2-carbon acid (2-benzo[1,3]dioxol-5-yl-ethyl)-amide, optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Further examples of preferred iNOS-Inhibitors which may be mentioned include antisense-Oligonucleotide, especially those antisense-Oligonucleotide binding iNOS-coding nucleinic acids, examples therefore are disclosed in WO 01/52902.

Examples of preferred SYK-inhibitors which may be mentioned include
2-[(2-aminoethyl)amino]-4-[(3-bromophenyl)amino]-5-pyrimidinecarboxamide;
2-[[7-(3,4-dimethoxyphenyl)imidazo[1,2-c]pyrimidine-5-yl]amino]-3-pyridinecarboxamide;
6-[[5-fluoro-2-[3,4,5-trimethoxyphenyl)amino]-4-pyrimidinyl]amino]-2,2-dimethyl-2H-pyrido[3,2-b]-1,4-oxazin-3(4H)-one;
N-[3-bromo-7-(4-methoxyphenyl)-1,6-naphthyridine-5-yl]-1,3-propanediamine;
7-(4-methoxyphenyl)-N-methyl-1,6-naphthyridine-5-amine;
N-[7-(4-methoxyphenyl)-1,6-naphthyridine-5-yl]-1,3-propanediamine;
N-[7-(2-thienyl)-1,6-naphthyridine-5-yl-1,3-propanediamine;
N-[7-[4-(dimethylamino)phenyl]-1,6-naphthyridine-5-yl]-1,2-ethanediamine;
N-[7-(4-methoxyphenyl)-2-(trifluoromethyl)-1,6-naphthyridine-5-yl]-1,3-propanediamine;
N-[7-(4-methoxyphenyl)-3-phenyl-1,6-naphthyridine-5-yl]-1,3-propanediamine;
N-(7-phenyl-1,6-naphthyridine-5-yl)-1,3-propanediamine;
N-[7-(3-fluorophenyl)-1,6-naphthyridine-5-yl]-1,3-propanediamine;
N-[7-(3-chlorophenyl)-1,6-naphthyridine-5-yl]-1,3-propanediamine;
N-[7-[3-(trifluoromethoxy)phenyl]-1,6-naphthyridine-5-yl]-1,3-propanediamine;
N-[7-(4-fluorophenyl)-1,6-naphthyridine-5-yl]-1,3-propanediamine;
N-[7-(4-fluorophenyl)-1,6-naphthyridine-5-yl]-1,3-propanediamine;
N-[7-(4-chlorophenyl)-1,6-naphthyridine-5-yl]-1,3-propanediamine;
N-[7-(4'-methyl[1,1'-biphenyl]-4-yl)-1,6-naphthyridine-1,3-propanediamine;
N-[7-[4-(dimethylamino)phenyl]-1,6-naphthyridine-5-yl]-1,3-propanediamine;
N-[7-[4-(diethylamino)phenyl]-1,6-naphthyridine-5-yl]-1,3-propanediamine;
N-[7-[4-(4-morpholinyl)phenyl]-1,6-naphthyridine-5-yl]-1,3-propanediamine;
N-[7-[4-[[2-(dimethylamino)ethyl]methylamino]phenyl]-1,6-naphthyridine-5-yl]-1,3-propanediamine;
N-[7-(4-bromophenyl)-1,6-naphthyridine-5-yl]-1,3-propanediamine;
N-[7-(4-methylphenyl)-1,6-naphthyridine-5-yl]-1,3-propanediamine;
N-[7-[4-(methylthio)phenyl]-1,6-naphthyridine-5-yl]-1,3-propanediamine;
N-[7-[4-(1-methylethyl)phenyl]-1,6-naphthyridine-5-yl]-1,3-propanediamine;
7-[4-(dimethylamino)phenyl]-N-methyl-1,6-naphthyridine-5-amine;
7-[4-(dimethylamino)phenyl]-N,N-dimethyl-1,6-naphthyridine-5-amine;
N-[7-[4-(dimethylamino)phenyl]-1,6-naphthyridine-5-yl]-1,4-butanediamine;
N-[7-[4-(dimethylamino)phenyl]-1,6-naphthyridine-5-yl]-1,5-pentanediamine;
3-[[7-[4-(dimethylamino)phenyl]-1,6-naphthyridine-5-yl]oxy]-1-propanole;
4-[5-(4-aminobutoxy)-1,6-naphthyridine-7-yl]-N,N-dimethyl-benzenamine;
4-[[7-[4-(dimethylamino)phenyl]-1,6-naphthyridine-5-yl]amino]-1-butanole;
N-[7-[4-(dimethylamino)phenyl]-1,6-naphthyridine-5-yl]-N-methyl-1,3-propanediamine;
N-[7-[4-(dimethylamino)phenyl]-1,6-naphthyridine-5-yl]-N'-methyl-1,3-propanediamine;
N-[7-[4-(dimethylamino)phenyl]-1,6-naphthyridine-5-yl]-N,N'-dimethyl-1,3-propanediamine;
1-amino-3-[[7-[4-(dimethylamino)phenyl]-1,6-naphthyridine-5-yl]amino]-2-propanole;
N-[7-[4-(dimethylamino)phenyl]-1,6-naphthyridine-5-yl]-2,2-dimethyl-1,3-propanediamine;
7-[4-(dimethylamino)phenyl]-N-(3-pyridinylmethyl)-1,6-naphthyridine-5-amine;
N-[(2-aminophenylmethyl]-7-[4-(dimethylamino)phenyl]-1,6-naphthyridine-5-amine;
N-[7-[6-(dimethylamino)[1,1'-biphenyl]-3-yl]-1,6-naphthyridine-5-yl]-1,3-propanediamine;
N-[7-[3-chloro-4-(diethylamino)phenyl]-1,6-naphthyridine-5-yl]-1,3-propanediamine;
N-[7-[4-(dimethylamino)-3-methoxyphenyl]-1,6-naphthyridine-5-yl]-1,3-propanediamine;
N-[7-[4-(diethylamino)phenyl]-3-methyl-1,6-naphthyridine-5-yl]-1,3-propanediamine;
N-[7-(3'-fluoro[1,1'-biphenyl]-3-yl)-1,6-naphthyridine-5-yl]-1,2-ethanediamin,
N-[7-(4-methoxyphenyl)-1,6-naphthyridine-5-yl]-1,6-naphthyridine-1,3-propanediamine;
N,N'-bis(3-aminopropyl)-7-(4-methoxyphenyl)-2,5-diamine;
N-[7-(4-methoxyphenyl)-2-(phenylmethoxy)-1,6-naphthyridine-5-yl]-1,6-naphthyridine-1,3-propanediamine;
N5-(3-aminopropyl)-7-(4-methoxyphenyl)-N2-(phenylmethyl)-2,5-diamine;
N-[7-(2-naphthalenyl)-1,6-naphthyridine-5-yl]-1,3-propanediamine;
N-[7-(2'-fluoro[1,1'-biphenyl]-4-yl)-1,6-naphthyridine-5-yl]-1,3-propanediamine;
N-[7-(3,4,5-trimethoxyphenyl)-1,6-naphthyridine-5-yl]-1,3-propanediamine;
N-[7-(3,4-dimethylphenyl)-1,6-naphthyridine-5-yl]-1,3-propanediamine;
1-amino-3-[[7-(2-naphthalenyl)-1,6-naphthyridine-5-yl]amino]-2-propanole;
1-amino-3-[[7-(2'-fluoro[1,1'-biphenyl]-4-yl)-1,6-naphthyridine-5-yl]amino]-2-propanole;
1-amino-3-[[7-(4'-methoxy[1,1'-biphenyl]-4-yl)-1,6-naphthyridine-5-yl]amino]-2-propanole;
1-amino-3-[[7-(3,4,5-trimethoxyphenyl)-1,6-naphthyridine-5-yl]amino]-2-propanole;
1-amino-3-[[7-(4-bromophenyl)-1,6-naphthyridine-5-yl]amino]-2-propanole;
N-[7-(4'-methoxy[1,1'-biphenyl]-4-yl)-1,6-naphthyridine-5-yl]-2,2-dimethyl-1,3-propanediamine;
1-[[7-[4-(dimethylamino)phenyl]-1,6-naphthyridine-5-yl]amino]-2-propanole;
2-[[2-[[7-[4-(dimethylamino)phenyl]-1,6-naphthyridine-5-yl]amino]ethyl]thio]-ethanole;
7-[4-(dimethylamino)phenyl]-N-(3-methyl-5-isoxazolyl)-1,6-naphthyridine-5-amine;
7-[4-(dimethylamino)phenyl]-N-4-pyrimidinyl-1,6-naphthyridine-5-amine;

N-[7-[4-(dimethylamino)phenyl]-1,6-naphthyridine-5-yl]-1,3-cyclohexane diamine;
N,N-dimethyl-4-[5-(1-piperazinyl)-1,6-naphthyridine-7-yl]-benzenamine;
4-[5-(2-methoxyethoxy)-1,6-naphthyridine-7-yl]-N,N-dimethyl-benzenamine;
1-[7-[4-(dimethylamino)phenyl]-1,6-naphthyridine-5-yl]-4-piperidinole;
1-[7-[4-(dimethylamino)phenyl]-1,6-naphthyridine-5-yl]-3-pyrrolidinole;
7-[4-(dimethylamino)phenyl]N-(2-furanylmethyl)-1,6-naphthyridine-5-amine;
7-[4-(dimethylamino)phenyl]-N-[3-(1H-imidazole-1-yl)propyl]-1,6-naphthyridine-5-amine;
1-[7-[4-(dimethylamino)phenyl]-1,6-naphthyridine-5-yl]-4-piperidine carboxamide;
1-[3-[[7-[4-(dimethylamino)phenyl]-1,6-naphthyridine-5-yl]amino]propyl]-2-pyrrolidinone;
N-[3'-[5-[(3-aminopropyl)amino]-1,6-naphthyridine-7-yl][1,1'-biphenyl]-3-yl]-acetamide;
N-[7-(4'-fluoro[1,1'-biphenyl]-4-yl)-1,6-naphthyridine-5-yl]-1,3-propanediamine;
N-[4'-[5-[(3-aminopropyl)amino]-1,6-naphthyridine-7-yl][1,1'-biphenyl]-3-yl]-acetamide;
N-[7-[4-(1,3-benzodioxol-5-yl)phenyl]-1,6-naphthyridine-5-yl]-1,3-propanediamine;
N-[7-[4-(2-thienyl)phenyl]-1,6-naphthyridine-5-yl]-1,3-propanediamine;
N-[7-[4-fluoro-3-(trifluoromethyl)phenyl]-1,6-naphthyridine-5-yl]-1,3-propanediamine;
N-[7-[4-(3-pyridinyl)phenyl]-1,6-naphthyridine-5-yl]-1,3-propanediamine;
N-[7-(1,3-benzodioxol-5-yl)-1,6-naphthyridine-5-yl]-1,3-propanediamine;
N-[7-(6-methoxy-2-naphthalenyl)-1,6-naphthyridine-5-yl]-1,3-propanediamine;
7-[4-(dimethylamino)phenyl]-N-(4-pyridinylmethyl)-1,6-naphthyridine-5-amine;
3-[[7-[4-(dimethylamino)phenyl]-1,6-naphthyridine-5-yl]methylamino]-propanenitrile;
7-[4-(dimethylamino)phenyl]-N-[1-(phenylmethyl)-4-piperidinyl]-1,6-naphthyridine-5-amine;
N-[7-[4-(dimethylamino)phenyl]-1,6-naphthyridine-5-yl]-1,2-cyclohexanediamin,
N-[7-[4-(dimethylamino)phenyl]-1,6-naphthyridine-5-yl]-1,2-Cyclohexanediamine, (1R,2S)-rel-.
N-[7-[4-(dimethylamino)phenyl]-1,6-naphthyridine-5-yl]-1,2-benzene dimethanamine;
N-[7-[4-(diethylamino)phenyl]-1,6-naphthyridine-5-yl]-1,4-butanediamine;
N-[7-[3',5'-bis(trifluoromethyl)[1,1'-biphenyl]-4-yl]-1,6-naphthyridine-5-yl]-,3-propanediamine;
N-[7-(3'-methoxy[1,1'-biphenyl]-4-yl)-1,6-naphthyridine-5-yl]-1,3-propanediamine;
N-[7-(3'-fluoro[1,1'-biphenyl]-4-yl)-1,6-naphthyridine-5-yl]-1,3-propanediamine;
4-[[7-[4-(dimethylamino)phenyl]-1,6-naphthyridine-5-yl]oxy]-1-butanole;
N-[7-[4-(dimethylamino)phenyl]-1,6-naphthyridine-5-yl]-1,4-cyclohexanediamine;
7-[4-(dimethylamino)phenyl]N-(2,2,6,6-tetramethyl-4-piperidinyl)-1,6-naphthyridine-5-amine;
N-[7-[3-bromo-4-(dimethylamino)phenyl]-1,6-naphthyridine-5-yl]-1,3-propanediamine;
N-[7-(1-methyl-1H-indole-5-yl)-1,6-naphthyridine-5-yl]-1,3-propanediamine;
N-[7-[3-(trifluoromethyl)phenyl]-1,6-naphthyridine-5-yl]-1,3-propanediamine;
N-[7-[4-(trifluoromethyl)phenyl]-1,6-naphthyridine-5-yl]-1,3-propanediamine;
N-[7-(3-bromo-4-methoxyphenyl)-1,6-naphthyridine-5-yl]-1,3-propanediamine;
N-[7-[4-[[3-(dimethylamino)propyl]methylamino]phenyl]-1,6-naphthyridine-5-yl]-1,4-cyclohexanediamine;
N-[7-[4-[[2-(dimethylamino)ethyl]methylamino]phenyl]-1,6-naphthyridine-5-yl]-1,4-cyclohexanediamine;
N-[7-[4-(dimethylamino)-3-methoxyphenyl]-1,6-naphthyridine-5-yl]-1,4-cyclohexanediamine;
N-[7-[4-(4-morpholinyl)phenyl]-1,6-naphthyridine-5-yl]-1,4-cyclohexanediamine;
N-[7-[3-bromo-4-(4-morpholinyl)phenyl]-1,6-naphthyridine-5-yl]-1,4-cyclohexanediamine;
4-[[7-[4-[[2-(dimethylamino)ethyl]methylamino]phenyl]-1,6-naphthyridine-5-yl]oxy]-cyclohexanole;
N-[7-[3-bromo-4-(4-morpholinyl)phenyl]-1,6-naphthyridine-5-yl]-1,3-propanediamine;
N,N-dimethyl-4-[5-(4-methyl-1-piperazinyl)-1,6-naphthyridine-7-yl]-benzenamine;
4-[[7-[4-[[3-(dimethylamino)propyl]methylamino]phenyl]-1,6-naphthyridine-5-yl]oxy]-cyclohexanole;
N-[7-[4-[[2-(dimethylamino)ethyl]methylamino]phenyl]-1,6-naphthyridine-5-yl]-1,4-butanediamin;
[3-[[5-[(3-aminopropyl)amino]-7-(4-methoxyphenyl)-1,6-naphthyridine-2-yl]amino]propyl]-carbamic acid-1,1-dimethylethyl ester, optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred corrections of the cystic fibrosis transmembrane regulator (CFTR) and CFTR potentiators which may be mentioned include, preferably VX-770 and VX-809

12. FORMULATIONS

Suitable forms for administration are for example inhalable powders or aerosols. The content of the pharmaceutically effective compound(s) in each case should be in the range from 0.2 to 50 wt %, preferably 5 to 25 wt. % of the total composition, i.e. in amounts which are sufficient to achieve the dosage range specified hereinafter.

Administered by inhalation the active substance combination may be given as a powder, as an aqueous or aqueous-ethanolic solution or using a propellant gas formulation.

Preferably, therefore, pharmaceutical formulations are characterised in that they contain one or more compounds of (I) according to the preferred embodiments above.

It is also preferred if the compounds of formula (I) are administered by inhalation, particularly preferably if they are administered once or twice a day. For this purpose, the compounds of formula (I) have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also include concentrates or sterile ready-to-use inhalable solutions. The preparations which may be used according to the invention are described in more detail in the next part of the specification.

Inhalable Powders

If the active substances of formula (I) are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain a compound of formula (I) dissolved in the propellant gas or in dispersed form. The is propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula (I) according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a compound according to the invention and one or more combination partners selected from those described above.

The following example illustrates the present invention without restricting its scope:

Capsule for Powder Inhalation 1 capsule contains:

| active substance | 0.5 mg |
|---|---|
| lactose for inhalation | 5.0 mg |
| | 5.5 mg |

Preparation:

The active substance is mixed with lactose for inhalation. The mixture is packed into capsules in a capsule-making machine (weight of the empty capsule approx. 50 mg).

weight of capsule: 55.5 mg size of capsule=3

The invention claimed is:

1. A compound of formula (I), (I)

characterized in that
$R^1$ denotes H or $C_{1-4}$-alkyl,
$R^2$ denotes H or $C_{1-4}$-alkyl,
$R^3$ denotes H or methyl,
$R^4$ denotes H or methyl, or
$R^3$ and $R^4$ together form an ethylene bridge,
$R^5$ denotes
  H, $C_{1-4}$-alkyl-, $C_{1-4}$-alkyl-O—CO—, $C_{1-4}$-alkyl-O—CO—$C_{1-4}$-alkyl-, $C_{1-4}$-alkyl-O—$C_{1-4}$-alkyl-, HO—CO— or HO—CO—$C_{1-4}$-alkyl-,
$R^6$ denotes
  H, halogen, CN, $N_3$, $C_{1-4}$-alkyl- which is optionally substituted by one or more F atoms, HC≡C—, OH, $C_{1-4}$-alkyl-O—, HO—$CH_2$—, $H_2C=CH—CH_2$—O—, HC≡C—$CH_2$—O— or —$NR^{6.1}R^{6.2}$,
  wherein,
  $R^{6.1}$ denotes H, $C_{1-4}$-alkyl-, $C_{1-4}$-alkyl-CO— or $C_{1-4}$-alkyl-$SO_2$—, and
  $R^{6.2}$ denotes H or $C_{1-4}$-alkyl-,
$R^7$ denotes
  H, halogen, CN, $N_3$, $C_{1-4}$-alkyl- which is optionally substituted by one or more F atoms, HC≡C—, OH, $C_{1-4}$-alkyl-O—, HO—$CH_2$—, $H_2C=CH—CH_2$—O—, HC≡C—$CH_2$—O—, —$NR^{7.1}R^{7.2}$,
  $H_2N—C(NH)$—, $H_2N—C(NH)NH$—, $H_2N—C(NH)NH—CH_2$—, —COOH, $C_{1-4}$-alkyl-OCO—, —$C_{1-4}$-alkyl-COOH, —$C_{1-4}$-alkyl-COO—$C_{1-4}$-alkyl, —$OCH_2$—COOH, —$OCH_2$—COO—$C_{1-4}$-alkyl, —$P(O)(OR^{7.3})(OR^{7.4})$, —$CH_2$—$P(O)(OR^{7.3})(OR^{7.4})$ or —$B(OH)_2$,
  wherein,
  $R^{7.1}$ denotes H, $C_{1-4}$-alkyl-, $C_{1-4}$-alkyl-CO— or $C_{1-4}$-alkyl-$SO_2$—,
  $R^{7.2}$ denotes H or $C_{1-4}$-alkyl-,
  $R^{7.3}$ and $R^{7.4}$ independently from each other denote H or $C_{1-4}$-alkyl,
$R^8$ denotes
  H, halogen, CN, $N_3$, $C_{1-4}$-alkyl- which is optionally substituted by one or more F atoms, HC≡C—, OH, $C_{1-4}$-alkyl-O—, HO—$CH_2$—, $H_2C=CH—CH_2$—O—, HC≡C—$CH_2$—O—, —$NR^{8.1}R^{8.2}$,
  $H_2N—C(NH)$—, $H_2N—C(NH)NH$—, $H_2N—C(NH)NH—CH_2$—, —COOH, $C_{1-4}$-alkyl-OCO—, —$C_{1-4}$-alkyl-COOH, —$C_{1-4}$-alkyl-COO—$C_{1-4}$-alkyl, —$OCH_2$—COOH, —$OCH_2$—COO—$C_{1-4}$-alkyl, —$P(O)(OR^{8.3})(OR^{8.4})$, —$CH_2$—$P(O)(OR^{8.3})(OR^{8.4})$ or —$B(OH)_2$,
  or
$R^8$ denotes -$L^2$-yl-$L^3$-$Y^2$-$L^4$-$R^{8.5}$
  wherein,
  $R^{8.1}$ denotes H, $C_{1-4}$-alkyl, $C_{1-4}$-alkyl-CO— or $C_{1-4}$-alkyl-$SO_2$—,
  $R^{8.2}$ denotes H or $C_{1-4}$-alkyl,
  or
  $R^{8.1}$ and $R^{8.2}$ together with the nitrogen atom they are attached to form a heterocycle $Y^3$,
  $R^{8.3}$ and $R^{8.4}$ independently from each other denote H or $C_{1-4}$-alkyl,
  $R^{10}$ and $R^{8.5}$ independently from each other are selected from the group consisting of
    H, halogen, CN, $N_3$, $C_{1-4}$-alkyl, HC≡C—, OH, $C_{1-4}$-alkyl-O—, HO—$CH_2$—, $H_2C=CH—CH_2$—O—, HC≡C—$CH_2$—O—, —$NR^{8.5.1}R^{8.5.2}$
    $B(OH)_2$, $BF_3^-$, —$S(O)_2OH$, —O—$C(C_6H_6)_3$, —$C(CH_2OH)_3$, —$CH(CH_2OH)_2$, —$CH(OH)CH_2OH$ and —$N^+(R^{8.5.3})_3$,
  $R^{8.5.1}$ denotes H, $C_{1-4}$-alkyl, $C_{1-4}$-alkyl-CO— or $C_{1-4}$-alkyl-$SO_2$—,
  $R^{8.5.2}$ denotes H or $C_{1-4}$-alkyl,
  or
  $R^{8.5.1}$ and $R^{8.5.2}$ together with the nitrogen atom they are attached to form a heterocycle $Y^3$,
  $R^{8.5.3}$ denotes methyl or ethyl,
$R^9$ denotes H or methyl,
m and n independently from each other denote 0, 1 or 2, with the proviso that the sum of m and n is less than 4,
X denotes halogen,
$L^1$ denotes a bond or is selected from the group consisting of
  —$CH_2$—, —$CH_2$—$CH_2$—, —$CH_2O$—, —CO—, —S—, —SO—, —$SO_2$—, —S—$CH_2$—, SO—$CH_2$— and —$SO_2$—$CH_2$—,
$L^2$ denotes a bond or is selected from the group consisting of —O—, —$CH_2$—, —$CH_2$—$CH_2$—, —$CH_2$—O—, —O—$CH_2$—, —CO—, —$CH_2$—CO—, —CO—$CH_2$—, —S—, —SO—, —$SO_2$— and —O—CO—,
$L^3$, $L^4$ and $L^5$ independently from each other denote a bond or a linear chain of formula (m)

$$—(CH_2)_i—[O—(CH_2)_{g1}]_{p1}—[NH—(CH_2)_{g2}]_{p2}—[O—(CH_2)_{g3}]_{p3}—$$ (m), wherein
i denotes 0, 1, 2, 3 or 4,
g1, g2 and g3 independently from each other denote 2, 3 or 4,
p1 and p3 independently from each other denote 0, 1, 2, 3 or 4,
p2 denotes 0 or 1,
with the provisio that the linear chain is consisting of 1 to 15 moieties selected from the group consisting of —$CH_2$—, —O— and —NH— and with the proviso that the nitrogen atom of formula (m) is not directly linked to another nitrogen atom,
$Y^1$ denotes a bond, $Y^{1.1}$ or —$NR^{Y1.1}$—,
wherein,
$R^{Y1.1}$ denotes $L^3$-H or $L^3$-$NR^{Y1.1.1}R^{Y1.1.2}$,
  wherein
  $R^{Y1.1.1}$ denotes
    H, $C_{1-4}$-alkyl-, $C_{1-4}$-alkyl-CO— or $C_{1-4}$-alkyl-$SO_2$—,
  $R^{Y1.1.2}$ denotes H or $C_{1-4}$-alkyl-,
  or
  $R^{Y1.1.1}$ and $R^{Y1.1.2}$ together with the nitrogen atom they are attached to form a heterocycle $Y^3$,
$Y^2$ denotes a bond or
is selected from a group consisting of
  $Y^{2.1}$, —CO—, —$NR^{Y2.1}$—CO—, —CO—$NR^{Y2.1}$—, —$Y^{2.1}$—$CONR^{Y2.1}$—, —$Y^{2.1}$—CO— and —$NR^{Y2}$—CO—$Y^{2.1}$—, with the proviso that carbonyl moieties are not directly attached to nitrogen atoms of aromatic heterocycles, wherein $R^{Y2.1}$ denotes -$L^3$-H or -$L^3$-$NR^{Y2.1.1}R^{Y2.1.2}$, $R^{Y2.1.1}$ denotes H, $C_{1-4}$-alkyl-, $C_{1-4}$-alkyl-CO— or $C_{1-4}$-alkyl-$SO_2$—, $R^{Y2.1.2}$ denotes H or $C_{1-4}$-alkyl-, or $R^{Y2.1.1}$ and $R^{Y2.1.2}$ together with the nitrogen atom they are attached to form a heterocycle $Y^3$, $Y^{1.1}$ and $Y^{2.1}$ independently from each other denote a bond or are selected from the group consisting of

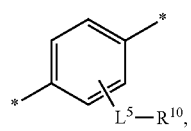 (a)

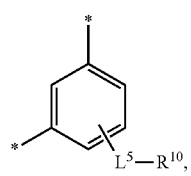 (b)

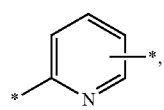 (c)

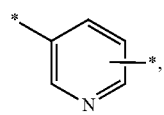 (d)

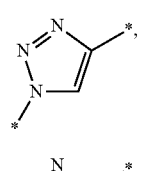 (e)

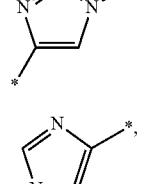 (f)

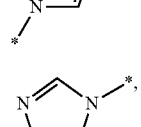 (g)

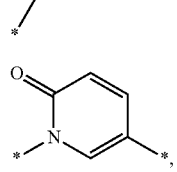 (h)

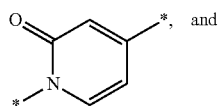 (i)

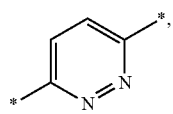 (j), and (k)

$Y^3$ denotes pyrrolidine or piperidine, each optionally substituted by up to two substituents independently selected from hydroxy or $C_{1-3}$-alkoxy, or $Y^3$ denotes morpholine, piperazine, 4-methyl-piperazine, 4-ethyl-piperazine, 4-acetyl-piperazine or 4-propionyl-piperazine, and tautomers and the pharmacologically acceptable acid addition salts thereof.

2. The compound of formula (I) according to claim 1, characterized in that

X denotes Cl or Br.

3. The compound of formula (I) according to claim 1, characterized in that $R^1$, $R^2$, $R^3$, $R^4$ and $R^5$ denote H, $R^9$ denotes H, X denotes Cl, $L^1$ denotes a bond, —$CH_2$—, —$CH_2O$— or —CO—, and m and n independently from each other denote 0, 1 or 2, with the proviso that the sum of m and n is greater than 0 and less than 4, $Y^3$ denotes morpholine, 4-acetyl-piperazine or 4-propionyl-piperazine.

4. The compound of formula (I) according to claim 1, characterized in that $R^7$ denotes

—COOH, —$CH_2$COOH, —$(CH_2)_2$COOH, —$OCH_2$—COOH, —$P(O)(OR^{7.3})(OR^{7.4})$,

—$CH_2$—$P(O)(OR^{7.3})(OR^{7.4})$ or —$B(OH)_2$, wherein $R^{7.3}$ denotes H, $R^8$ denotes $C_{1-4}$-alkyl-O—, HO—$CH_2$—, $H_2C$=CH—$CH_2$—O—, HC≡C—$CH_2$—O— or —$NR^{8.1}R^{8.2}$, wherein $R^{8.1}$ denotes H, $C_{1-4}$-alkyl-CO— or $C_{1-4}$-alkyl-$SO_2$—, $R^{8.2}$ denotes H or $C_{1-4}$-alkyl-, or $R^{8.1}$ and $R^{8.2}$ together with the nitrogen atom they are attached to form a heterocycle $Y^3$.

5. The compound of formula (I) according to claim 1, characterized in that $R^7$ denotes $C_{1-4}$-alkyl-OCO—, —$C_{1-2}$-alkyl-COO—$C_{1-4}$-alkyl, —$OCH_2$—COO—$C_{1-4}$-alkyl, —$P(O)(OR^{7.3})(OR^{7.4})$ or $CH_2$—$P(O)(OR^{7.3})(OR^{7.4})$, wherein $R^{7.3}$ and $R^{7.4}$ independently from each other denote methyl, ethyl, or 2-propyl, $R^8$ denotes H, halogen, CN, $C_{1-4}$-alkyl-, HC≡C—, OH, $C_{1-4}$-alkyl-O—, HO—$CH_2$—, $H_2C$=CH—$CH_2$—O—, HC≡C—$CH_2$—O— or —$NR^{8.1}R^{8.2}$, wherein $R^{8.1}$ denotes H, $C_{1-4}$-alkyl-, $C_{1-4}$-alkyl-CO— or $C_{1-4}$-alkyl-$SO_2$—, $R^{8.2}$ denotes H or $C_{1-4}$-alkyl-,
or
$R^{8.1}$ and $R^{8.2}$ together with the nitrogen atom they are attached to form a heterocycle $Y^3$.

6. The compound of formula (I) according to claim 1, characterized in that
L$^3$ and L$^4$ independently from each other denote a bond, —CH$_2$— or —CH$_2$—CH$_2$—,
$R^8$ denotes -L$^2$-Y$^1$-L$^3$-Y$^2$-L$^4$-R$^{8.5}$,
wherein
$R^{8.5}$ denotes —NH$_2$ or —N$^+$(R$^{8.5.3}$)$_3$,
$R^{8.5.3}$ denotes methyl or ethyl,
$R^{10}$ denotes H,
with the proviso that if Y$^2$ denotes a bond, then L$^2$ denotes —CO— and Y$^1$ denotes —NR$^{Y1.1}$.

7. The compound of formula (I) according to claim 1, characterized in that
L$^2$ denotes —CH$_2$—CH$_2$—,
Y$^1$ denotes Y$^{1.1}$,
wherein
Y$^{1.1}$ is selected from a group consisting of linkers of formula (c), (d), (e), (f) and (k)

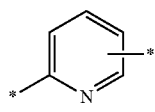

(c)

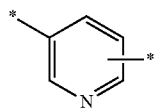

(d)

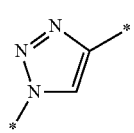

(e)

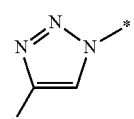

(f)

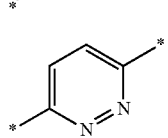

(k)

with the proviso that L$^3$ is not a bond.

8. A compound of formula (I) according to claim 1, characterized in that
R$^7$ denotes
H, halogen, CN, OH, C$_{1-4}$-alkyl-O— or HO—CH$_2$—,
R$^{8.5}$ denotes H, OH, C$_{1-4}$-alkyl-O—, —C(CH$_2$OH)$_3$, —CH(CH$_2$OH)$_2$ or —CH(OH)CH$_2$OH,
L$^2$ denotes a bond, —CH$_2$—CH$_2$— or —O—CH$_2$—,
L$^3$ denotes a bond,
L$^4$ denotes a linear chain of formula (m.1):

—(CH$_2$)$_i$—[O—(CH$_2$)$_{g1}$]$_{p1}$— (m.1), wherein
i denotes 0, 1, 2, or 3,
g1 denotes 2, or 3,
p1 denotes 0, 1 or 2, with the proviso that if R$^{8.5}$ denotes OH, or C$_{1-4}$-alkyl-O—,
then the sum of i and p1 is greater than 0
and with the proviso that if R$^{8.5}$ denotes H, then p1 is greater than 0,
and with the provisio that the linear chain or formula (m.1) consists of no more than 8 moieties selected from the group consisting of —CH$_2$— and —O—,
Y$^1$ denotes a bond,
Y$^2$ denotes —CO—NH— or Y$^{2.1}$
wherein
Y$^{2.1}$ is selected from a group consisting of linkers of formula (c), (d), (e), (f) and (k)

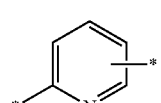

(c)

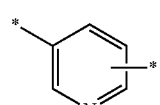

(d)

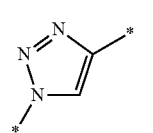

(e)

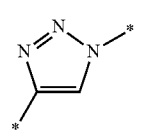

(f)

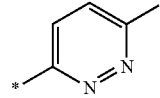

(k)

9. The compound of formula (I) according to claim 1, characterized in that
L$^2$ denotes a bond,
L$^3$ and L$^4$ independently from each other denote a bond or a linear chain of formula (m)

—(CH$_2$)$_i$—[O—(CH$_2$)$_{g1}$]$_{p1}$—[NH—(CH$_2$)$_{g2}$]$_{p2}$—[O—(CH$_2$)$_{g3}$]$_{p3}$— (m), wherein
i denotes 0, 1, 2 or 3,
g1 denotes 2, 3 or 4,
g2 denotes 0,
g3 denotes 2 or 3,
p1 denotes 0 or 1,
p3 denotes 2, 3 or 4,
p2 denotes 0,
with the provisio that the linear chain consists of 5 to 12 moieties selected from the group consisting of —CH$_2$— or —O—,
with the proviso that L$^3$ and L$^4$ together consist of at least eight —CH$_2$— moieties and of at least four —O— moieties,
Y$^1$ denotes Y$^{1.1}$,
wherein
Y$^{1.1}$ denotes a linker of formula (e) or (f)

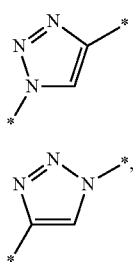
(e)
(f)
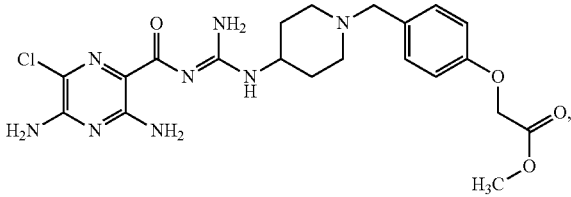 [SMILES: COC(=O)COc1ccc(CN2CCC(N/C(N)=N/C(=O)c3nc(Cl)c(N)nc3N)CC2)cc1]
e)
Y² denotes a bond or
is selected from a group consisting of $Y^{2.1}$, $-Y^{2.1}-CONR^{Y2.1}-$ and $-NR^{Y2.1}-CO-Y^{2.1}-$,
and
$R^{8.5}$ denotes H, OH and $OCH_3$.
10. A compound of formula (I) according to claim 1, characterized in that
the compound is selected from the group consisting of:
a)
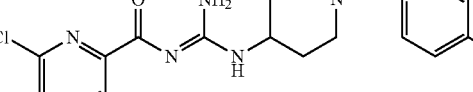
f)
b)
c)
g)
d)
h)

i)
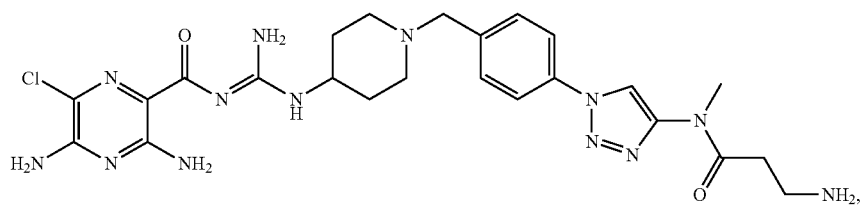 [SMILES: CN(C(=O)CCN)c1cn(-c2ccc(CN3CCC(N/C(N)=N/C(=O)c4nc(Cl)c(N)nc4N)CC3)cc2)nn1]
j)
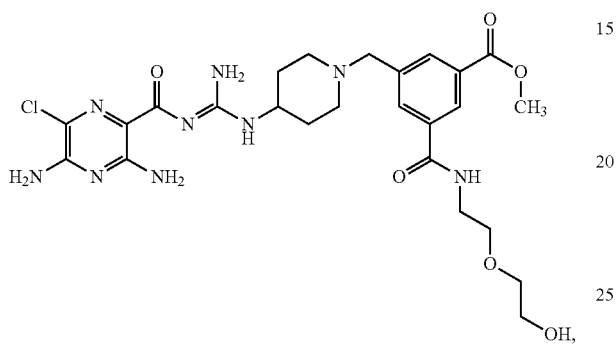
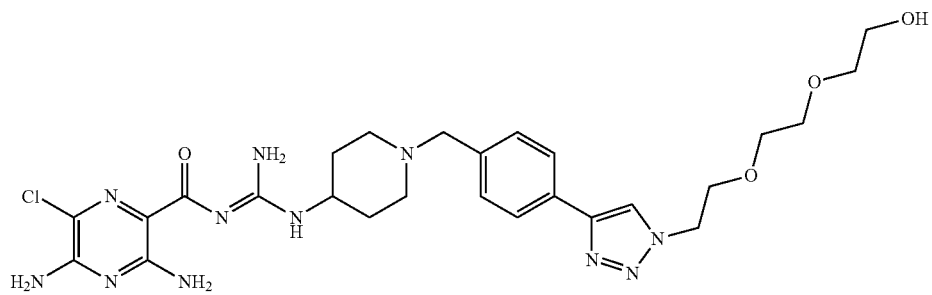 [SMILES: N/C(=N\C(=O)c1nc(Cl)c(N)nc1N)NC1CCN(Cc2ccc(-c3cn(CCOCCOCCO)nn3)cc2)CC1]
and
k)
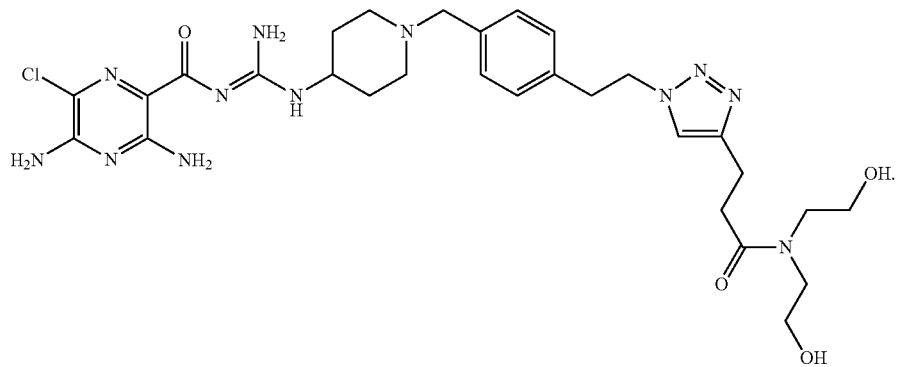 [SMILES: N/C(=N\C(=O)c1nc(Cl)c(N)nc1N)NC1CCN(Cc2ccc(CCn3cc(CCC(=O)N(CCO)CCO)nn3)cc2)CC1]
11. A pharmaceutical composition comprising a compound according to claim 1 or a pharmaceutically acceptable salt thereof and a pharmaceutically acceptable carrier.
* * * * *

UNITED STATES PATENT AND TRADEMARK OFFICE
CERTIFICATE OF CORRECTION

Page 1 of 1

PATENT NO.         : 8,859,559 B2
APPLICATION NO.    : 13/717848
DATED              : October 14, 2014
INVENTOR(S)        : Armin Heckel et al.

It is certified that error appears in the above-identified patent and that said Letters Patent is hereby corrected as shown below:

On the title page of the Patent in column 1, between Item (54) and Item (72), delete Item (71) in its entirety and replace it as follows:

(71) Applicant:  Armin Heckel, Biberach an der Riss (DE); Andreas Blum, Warthausen (DE); Dieter Hamprecht, Pozzolengo (IT); Joerg Kley, Mittelbiberach (DE)

Signed and Sealed this
Eighteenth Day of November, 2014

Michelle K. Lee
*Deputy Director of the United States Patent and Trademark Office*